(12) United States Patent
Shiota et al.

(10) Patent No.: US 12,702,393 B2
(45) Date of Patent: Aug. 11, 2026

(54) ENDOSCOPIC TREATMENT TOOL

(71) Applicant: OLYMPUS MEDICAL SYSTEMS CORP., Tokyo (JP)

(72) Inventors: Yusuke Shiota, Machida (JP); Chika Miyajima, Hachioji (JP); Junichi Kogiso, Hachioji (JP); Yuya Hidaka, Hino (JP); Naoki Takizawa, Musashino (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 229 days.

(21) Appl. No.: 18/538,371

(22) Filed: Dec. 13, 2023

(65) Prior Publication Data

US 2024/0197299 A1 Jun. 20, 2024

Related U.S. Application Data

(60) Provisional application No. 63/387,401, filed on Dec. 14, 2022.

(51) Int. Cl.
*A61B 17/00* (2006.01)
*A61B 18/00* (2006.01)
*A61B 18/14* (2006.01)

(52) U.S. Cl.
CPC .... *A61B 17/00234* (2013.01); *A61B 18/1492* (2013.01); *A61B 2017/00269* (2013.01);
(Continued)

(58) Field of Classification Search
None
See application file for complete search history.

(56) References Cited

U.S. PATENT DOCUMENTS 5,968,033 A * 10/1999 Fuller .................... A61B 18/22 606/17
7,220,257 B1 * 5/2007 Lafontaine ............. A61F 7/123 606/21
(Continued)

FOREIGN PATENT DOCUMENTS

CN 108515060 9/2018
JP 06505654 6/1994
(Continued)

OTHER PUBLICATIONS

"Japanese Application No. 2023-209176, Notice of Allowance dated Mar. 25, 2025", w English Translation, (Mar. 25, 2025), 6 pgs.
(Continued)

*Primary Examiner* — Linda C Dvorak
*Assistant Examiner* — Nicholas S Borsch
(74) *Attorney, Agent, or Firm* — Schwegman Lundberg & Woessner, P.A.

(57) ABSTRACT

An endoscopic treatment may include a sheath extending in a longitudinal direction, a distal end member having insulation and the distal end member provided at a distal end of the sheath and having a through-hole penetrating in the longitudinal direction. The treatment tool may further include an electrode having a first conduit extending in the longitudinal direction and the electrode being configured to advance and retract into the through-hole. The electrode including a rod extending in the longitudinal direction and configured to be arranged in at least a part of the first conduit.

18 Claims, 26 Drawing Sheets

(52) U.S. Cl.
CPC ............... *A61B 2018/00601* (2013.01); *A61B 2018/1475* (2013.01)

(56) References Cited

U.S. PATENT DOCUMENTS

| | | | | |
|---|---|---|---|---|
| 2010/0217073 | A1 | 8/2010 | Fischer et al. | |
| 2017/0224411 | A1 | 8/2017 | Onuki et al. | |
| 2018/0271594 | A1* | 9/2018 | Tyson | A61B 18/1206 |
| 2019/0357899 | A1* | 11/2019 | Gilbert | A61B 17/0467 |
| 2021/0113260 | A1* | 4/2021 | Tang | A61M 5/1407 |
| 2022/0096154 | A1 | 3/2022 | Smith et al. | |
| 2022/0151680 | A1 | 5/2022 | Ohata et al. | |

FOREIGN PATENT DOCUMENTS

| | | |
|---|---|---|
| JP | 10024049 | 4/1997 |
| JP | 2006326157 | 12/2006 |
| JP | 2010536515 | 12/2010 |
| JP | 2014054372 | 3/2014 |
| JP | 2023067784 | 5/2023 |
| JP | 2023117390 | 8/2023 |
| WO | 9213494 | 8/1992 |
| WO | 2018182101 | 10/2018 |
| WO | 2021140609 | 7/2021 |

OTHER PUBLICATIONS

"Japanese Application No. 2023-209176, Office Action dated Oct. 22, 2024", w English Translation, (Oct. 22, 2024), 15 pgs.

"Japanese Application No. 2023-209176, Office Action dated Jan. 21, 2025", w English Translation, (Jan. 21, 2025), 9 pgs.

"Indian Application No. 202344084637, Office Action dated Nov. 21, 2025", Nov. 21, 2025, 8 pgs.

* cited by examiner

300F
7
HIGH-FREQUENCY POWER SUPPLY DEVICE
6
SWITCH
71
SWITCH DETECTION UNIT
74
FIRST CONTROL UNIT
72
OUTPUT UNIT
100F
TREATMENT TOOL
73
FIRST COMMUNICATION UNIT
8
LIQUID SUPPLY DEVICE
82
SECOND COMMUNICATION UNIT
84
ABNORMALITY DETECTION UNIT
83
SECOND CONTROL UNIT
81
WATER SUPPLY UNIT

ENDOSCOPIC TREATMENT TOOL

CROSS-REFERENCE TO RELATED APPLICATIONS

The present application claims priority based on U.S. Patent Provisional Application No. 63/387,401 filed in the United States on Dec. 14, 2022, the contents of which are incorporated herein by reference.

TECHNICAL FIELD

The present disclosure relates to an endoscopic treatment tool.

BACKGROUND

In endoscopic therapy such as endoscopic submucosal dissection (ESD), an endoscopic treatment tool for incision, cauterization, peeling, or the like such as a high-frequency knife, and an endoscopic treatment tool for local injection, an endoscopic treatment tool for hemostasis, or the like, may be used.

Endoscopic treatment tools such as those described in United States Patent Application, Publication No. 2021/0113260 (hereinafter referred to as Patent Document 1) and United States Patent Application, Publication No. 2022/0096154 (hereinafter referred to as Patent Document 2) are configured to be able to perform incision, cauterization, or peeling treatments and a hemostatic treatment using a high-frequency knife, and perform a local injection treatment in which a liquid (local injection liquid) is supplied from a distal end of a sheath. Also, Patent Document 1 and Patent Document 2 describe an endoscopic treatment tool (so-called dual knife) capable of supplying water from a water supply port provided at a distal end of the high-frequency knife in addition to supplying water from a water supply port of the sheath formed on a side surface of the high-frequency knife.

SUMMARY

In the endoscopic treatment tools described in Patent Documents 1 and 2, since a distal end of the high-frequency knife is applied to a treatment site during incision, cauterization, or peeling treatments and a hemostasis treatment, tissues may adhere to the distal end of the high-frequency knife or enter a water supply port provided at the distal end to cause clogging thereof. A capacity to supply a fluid to the treatment site may be weakened or water supply may become unstable when an operator performs a local injection treatment. Also, if high-frequency energy is supplied while tissues are attached to the high-frequency knife, the tissues may become burnt deposits that may become fixed to the distal end of the high-frequency knife.

The present disclosure relates to an endoscopic treatment tool in which water supply from a distal end of a high-frequency knife or sheath can be suitably performed.

In an example, an endoscopic treatment tool may include a sheath extending in a longitudinal direction, a distal end member having insulation and the distal end member provided at a distal end of the sheath and having a through-hole penetrating in the longitudinal direction, an electrode having a first conduit extending in the longitudinal direction and the electrode being configured to advance and retract into the through-hole, and a rod extending in the longitudinal direction and configured to be arranged in at least a part of the first conduit.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 25 is a view showing a connection between a lever and a rod of the operation unit.

FIG. 30 is a cross-sectional view of the distal end part of the treatment tool.

FIG. 31 is a cross-sectional view illustrating an insulation tip of a sheath which is a modified example of an insulation tip of a sheath of the treatment tool.

DETAILED DESCRIPTION

First Embodiment

Figure 1:
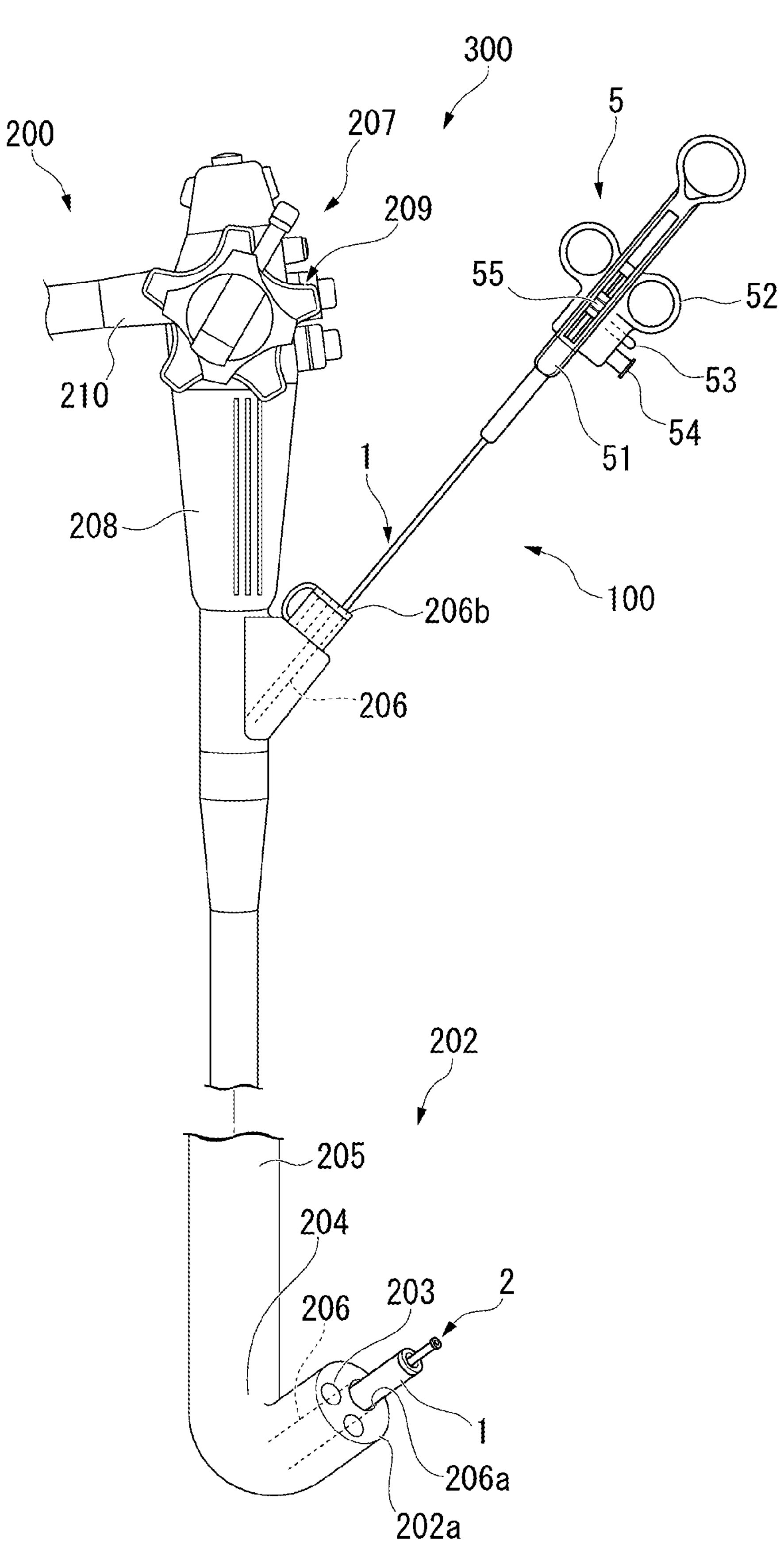
FIG. 1 is a view illustrating an overall configuration of an endoscopic treatment system.

An endoscopic treatment system (treatment system) 300 according to a first example embodiment will be described with reference to FIGS. 1 to 8. FIG. 1 is a view illustrating an overall configuration of the endoscopic treatment system 300 according to the first embodiment.

[Endoscopic Treatment System 300]

The endoscopic treatment system 300 may be used for medical procedures such as surgeries on the digestive tract or the like. As illustrated in FIG. 1, the endoscopic treatment system 300 includes an endoscope 200 and a treatment tool 100 (endoscopic treatment tool). The treatment tool 100 may be used by being inserted into the endoscope 200.

[Endoscope 200]

The endoscope 200 may include a long insertion part 202 that may be inserted into a body from a distal end thereof, and an operation unit 207 provided at a proximal end part of the insertion part 202.

The insertion part 202 may include an imaging unit 203, a curved part 204, and a flexible part 205. The imaging unit 203, the curved part 204, and the flexible part 205 may be disposed in that order from the distal end of the insertion part 202. A treatment tool channel 206 through which the treatment tool 100 may be inserted may be formed in the insertion part 202. A distal end opening **206*a* of the treatment tool channel 206 may be provided at a distal end 202*a* of the insertion part 202. The treatment tool channel 206 may extend from the distal end 202*a* of the insertion part 202 to the operation unit 207**.

The imaging unit 203 may include an imaging element such as, for example, a charge-coupled device (CCD) or a complementary metal oxide semiconductor (CMOS) sensor, or any similar device or sensor capable of imaging a region to be treated. The imaging unit 203 may image a knife 2 of the treatment tool 100 in a state in which the treatment tool 100 protrudes from the distal end opening **206*a* of the channel 206**.

The curved part 204 may curve according to an operation of the operation unit 207 by an operator. The flexible part 205 may be a tubular portion having flexibility.

The operation unit 207 may be connected to the flexible part 205. The operation unit 207 may include a grip 208, an input unit 209, a proximal end opening **206*b* of the channel 206, and/or a universal cord 210. The grip 208 may be a portion that is gripped by the operator. The input unit 209 may receive an operational input to cause a bending motion of the curved part 204. The universal cord 210 may output an image captured by the imaging unit 203 to the outside. The universal cord 210** may be connected to a display device such as a liquid crystal display (LCD) via an image-processing device including a processor or the like.

[Treatment Tool 100]

Figure 2:
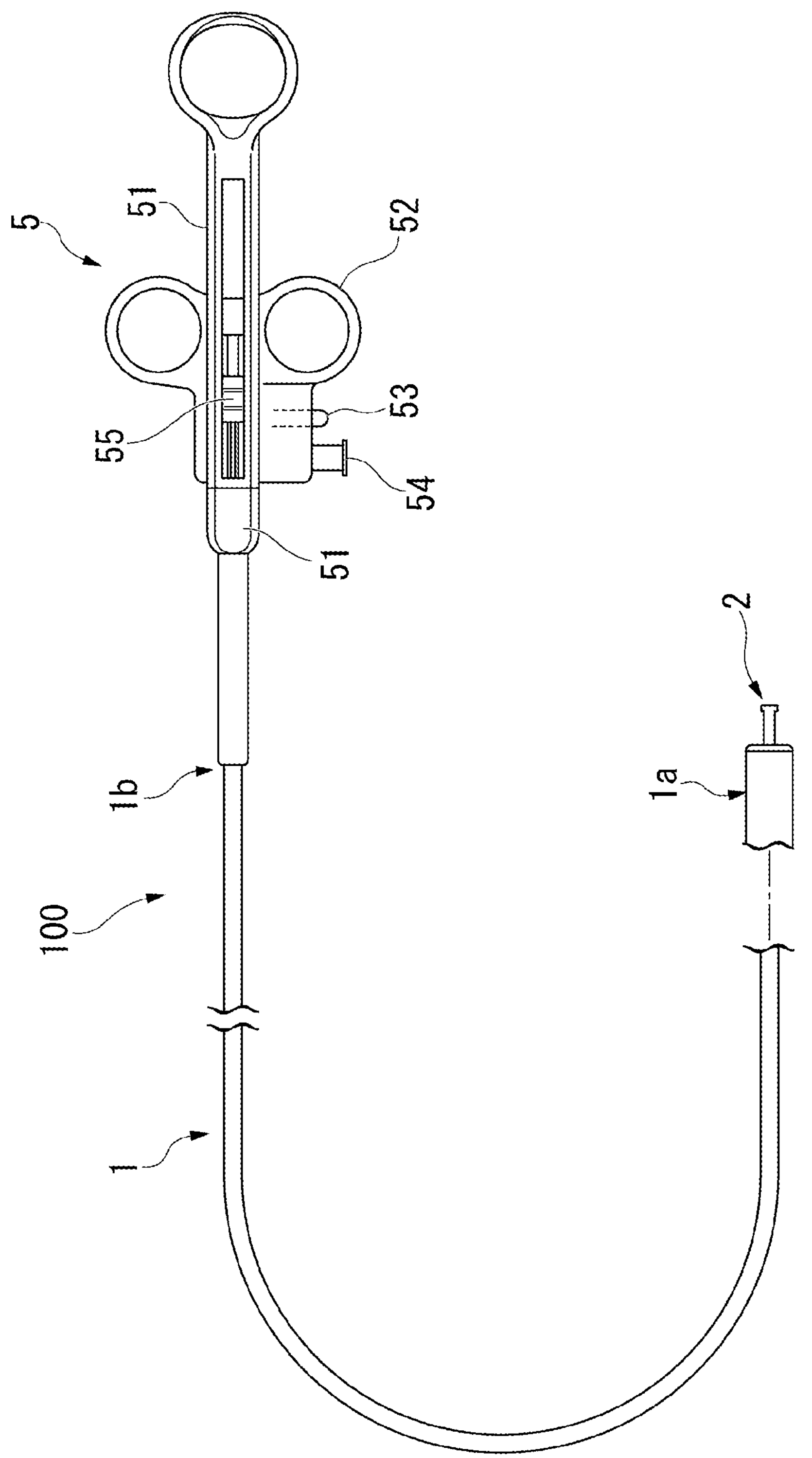
FIG. 2 is an overall view illustrating a treatment tool of the endoscopic treatment system.

FIG. 2 is an overall view illustrating the treatment tool 100.

The treatment tool 100 includes may include a sheath 1, the knife (high-frequency knife, electrode) 2, a rod-shaped member (rod) 3, a connecting insert 23, an operation wire 4 (see FIG. 4), and/or an operation unit 5. In the following description, in a longitudinal direction A of the treatment tool 100, a side inserted into a patient's body will be referred to as a "distal end side A1," and a side of the operation unit 5 will be referred to as a "proximal end side A2". Also, a width direction of the treatment tool 100 (a left-right direction of the treatment tool 100 in a front view) orthogonal to the longitudinal direction A is defined as a "width direction Y (see FIG. 3)".

[Sheath 1]

The sheath 1 may extend in the longitudinal direction A. The sheath 1 may be a long resin member having flexibility and insulating properties and extending from a distal end **1*a* to a proximal end 1*b*. The sheath 1 may include an outer diameter that can be inserted into the channel 206 of the endoscope 200 and may move (e.g., forward and backward) in the channel 206. As illustrated in FIG. 1, in a state in which the sheath 1 is inserted into the channel 206, the distal end Ta of the sheath 1 may protrude from and retract into the distal end opening 206*a* of the channel 206**.

Figure 3:
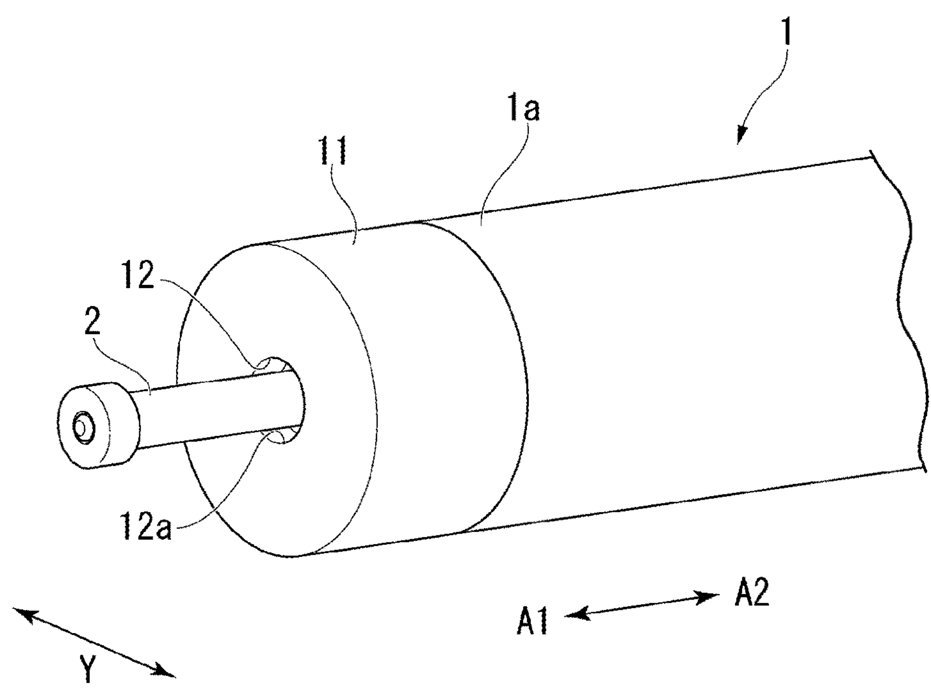
FIG. 3 is a perspective view of a distal end part of the treatment tool.

FIG. 3 is a perspective view of a distal end part of the treatment tool 100.

An insulation tip (distal end member) 11 having insulating properties and having a through-hole 12 penetrating in the longitudinal direction A may be attached to the distal end **1*a* of the sheath 1. The through-hole 12 may include a tip conduit 12*h* (see FIG. 4) extending in the longitudinal direction A. A distal end opening 12*a* may be formed at a distal end of the tip conduit 12*h*. The knife 2 and the rod 3 (e.g., a rod-shaped member) may be inserted into the through-hole 12. The knife 2 and the rod 3 may be configured or located so as to be movable forward and backward in the longitudinal direction A in the tip conduit 12*h***.

[Knife (High-Frequency Knife) 2]

Figure 4:
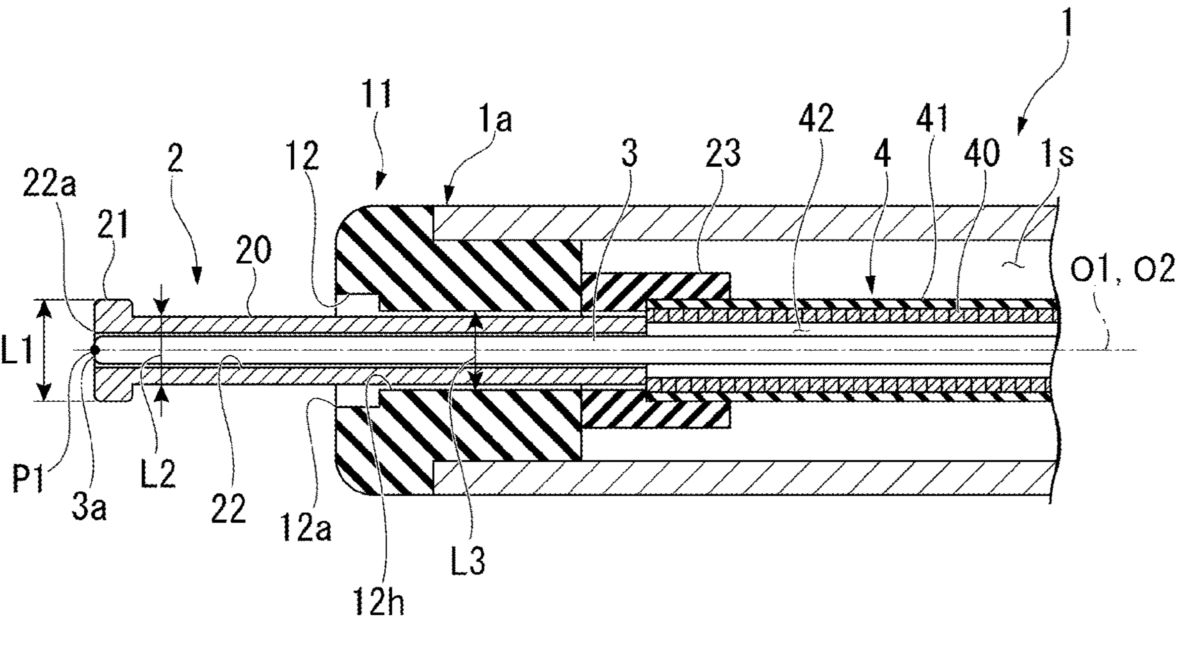
FIG. 4 is a cross-sectional view of the distal end part of the treatment tool.

FIG. 4 is a cross-sectional view of the distal end part of the treatment tool 100.

The knife 2 may be a high-frequency dual knife capable of incision, cauterization, or peeling using, for example, a water supply and a high-frequency current. The knife 2 may be a substantially round rod-shaped member made of a metal that may be inserted into the sheath 1 to move forward and backward in the longitudinal direction A. The knife 2 may be configured or located so as to be able to protrude to the distal end side A1 from the distal end opening 12*a* of the insulation tip 11 of the sheath 1. The knife 2 may be formed of a material such as, for example, stainless steel. The knife 2 has conductivity, and a high-frequency current may be applied thereto. The knife 2 may include a knife main body 20 and a flange 21.

The knife 2 may be movable relative to the rod 3 to be described later. A central axis O2 of the knife 2 in the longitudinal direction A may substantially coincide with a central axis O1 of the sheath 1 in the longitudinal direction A.

The knife main body 20 may be a round rod-shaped member made of a metal. The operation wire 4 may be attached to a proximal end of the knife main body 20. The knife main body 20 may supply a high-frequency current via the operation wire 4 connecting the operation unit 5 of FIG. 2 to the flange 21. When a high-frequency current is supplied from the operation wire 4 to the knife 2, the knife main body 20 and the flange 21 may function as a monopolar electrode that outputs the high-frequency current to biological tissues.

The flange (distal end part) 21 may be an annular plate-shaped conductive member provided at a distal end of the knife main body 20. In a front view in the longitudinal direction A, an outer circumference of the flange 21 may be formed concentrically with an outer circumference of the knife main body 20. As illustrated in FIG. 4, a width L1 of the flange 21 in a radial direction perpendicular to the longitudinal direction A may be larger than a width L2 of the knife main body 20 in the radial direction.

The distal end opening 12*a* of the tip conduit 12*h* may be formed in a size to engage with the flange 21, which is a distal end part of the knife 2. Also, an inner diameter L3 of the tip conduit 12*h* may be smaller than the width L1 of the flange 21 in the radial direction. Therefore, the flange 21 may be locked at the distal end opening 12*a* and may not move from the distal end opening 12*a* to the proximal end side A2.

The knife main body 20 and the flange 21 may include a first water supply conduit 22 (a first conduit) extending in the longitudinal direction A. A liquid may flow through the first water supply conduit 22. The first water supply conduit 22 may communicate with a distal end opening 22*a* (water supply port or first opening) formed in the flange 21. In other words, the first water supply conduit 22 includes the distal end opening 22*a* on the distal end side A1.

[Rod (Rod-Shaped Member) 3]

The rod (rod-shaped member) 3 may be a flexible round rod-shaped member that extends in the longitudinal direction A and may be formed of a resin material, a metal material, or the like. Similarly to the knife 2, the rod 3 includes the central axis O2 as a central axis. The rod 3 may be inserted into the knife 2 and the operation wire 4 in the longitudinal direction A, and may move (e.g., forward and backward) relative to the knife 2 and the operation wire 4. Specifically, the rod 3 may be inserted into the first water supply conduit 22 of the knife 2 and a second water supply conduit 42 (second conduit) of the operation wire 4 to be described below.

At least a distal end 3*a* of the rod 3 on the distal end side A1 may include an outer diameter slightly smaller than an outer diameter of the distal end opening 22*a*. The distal end 3*a* may function as a plug for the first water supply conduit 22 and the second water supply conduit 42 of the operation wire 4, discussed below. In the present example embodiment, the rod 3 may have the same outer diameter at any position in the longitudinal direction A. A proximal end portion of the rod 3 may be connected to a lever 55 of the operation unit 5 as discussed below.

[Connecting Insert 23]

As illustrated in FIG. 4, the connecting insert 23 may be attached to the knife 2. The connecting insert 23 may be attached to the knife 2 in a circumferential direction on the proximal end side A2 and to the operation wire 4 in a circumferential direction on the distal end side A1 to connect a proximal end of the knife 2 and a distal end of the operation wire 4.

[Operation Wire 4]

As illustrated in FIG. 4, the operation wire 4 may be a shaft inserted through an internal space is of the sheath 1, and may include a coil shaft 40 and a tube 41. The distal end of the operation wire 4 may be connected to the knife 2 by the connecting insert 23, and a proximal end of the operation wire 4 may be connected to the operation unit 5. Further, the operation wire 4 may have other forms as long as it is a hollow shaft.

The coil shaft 40 may be a coil wire made of a metal. The coil shaft 40 may be formed of a material such as, for example, stainless steel. The second water supply conduit 42 may be formed inside the coil shaft 40. The second water supply conduit 42 may be connected to, communicative coupled to (or otherwise communicates with) a proximal end of the first water supply conduit 22.

The tube 41 may be a tube provided on an outer circumferential portion of the coil shaft 40 and may be, for example, a heat-shrinkable tube. In such an example, since the outer circumferential portion of the coil shaft 40 is covered with the tube 41, a liquid does not leak out of the second water supply conduit 42.

[Operation Unit 5]

As illustrated in FIGS. 1 and 2, the operation unit 5 may include an operation unit main body 51, a slider 52, a power supply connector 53, a liquid supply port 54, and/or the lever 55 (e.g., a slide lever).

A distal end part of the operation unit main body 51 may be connected to the proximal end 1*b* of the sheath 1. The operation unit main body 51 may include an internal space through which the operation wire 4 can be inserted. The rod 3 and the operation wire 4 may pass through the internal space is of the sheath 1 (as illustrated in FIG. 4) and the internal space of the operation unit main body 51, and may extend to the slider 52.

The slider 52 may be attached to the operation unit main body 51 so as to be movable in the longitudinal direction A. The slider 52 may be attached to the sheath 1 connected to the operation unit main body 51 via an O-ring or the like. The proximal end of the operation wire 4 may in turn be attached to the slider 52. In an example, when the operator moves the slider 52 forward and backward relative to the operation unit main body 51, the operation wire 4 and the knife 2 may move forward and backward.

The power supply connector 53 may be fixed to the slider 52. The power supply connector 53 may be connected to a high-frequency power supply device and may be connected to a proximal end part of the operation wire 4 via a conductive wire or the like. The power supply connector 53 may supply a high-frequency current supplied from a high-frequency power supply device to the knife 2 via the operation wire 4.

The liquid supply port 54 may be provided in the slider 52. The liquid supply port 54 may be connected to a proximal end of the second water supply conduit 42 via a water supply conduit formed in the slider 52. A liquid supply device such as, for example, a pump may be connected to the liquid supply port 54. The pump may supply a liquid (e.g., water) to the liquid supply port 54. The liquid supplied from the liquid supply port 54 may pass through the water supply conduit formed in the slider 52, the second water supply conduit 42, and the first water supply conduit 22 to be discharged from the distal end opening 22*a*.

A proximal end of the rod 3 may attached to the lever 55 and the lever 55 may be attached to the slider 52 so as to be movable in the longitudinal direction A. The operator can thus move the rod 3 forward and backward in the longitudinal direction A by moving the lever 55 in the longitudinal direction A.

Next, a relationship between an operation of the operation unit 5, and the knife 2 and the rod 3 will be described.

As illustrated in FIGS. 3 and 4, when the slider 52 and the lever 55 are moved to the distal end side A1, the knife 2 and the rod 3 protrude from the distal end 1*a* of the sheath 1. A state of the knife 2 and the rod 3 at this time may be defined as a treatment state. In the treatment state, the operator can perform incision, cauterization, or peeling treatments. Also in the treatment state, the distal end 3*a* of the rod 3 is positioned at the distal end opening 22*a* in the longitudinal direction A. In the following description, a position at which the distal end 3*a* is disposed at the distal end opening 22*a* in the longitudinal direction A will be referred to as a first position PT. The distal end 3*a* may overlap the distal end opening 22*a* at the first position P1 when viewed from the width direction Y That is, when the distal end 3*a* is located at the first position P1, the position of the distal end 3*a* in the longitudinal direction A coincides with the position of the distal end of the knife 2. When the distal end 3*a* of the rod 3 is located at the first position P1, the distal end opening 22*a* can be sealed by the distal end 3*a* of the rod 3. The configuration of the rod 3 when the rod 3 seals the distal end opening 22*a* with the distal end 3*a* disposed at the first position P1 is referred to as a first configuration.

Figure 5:
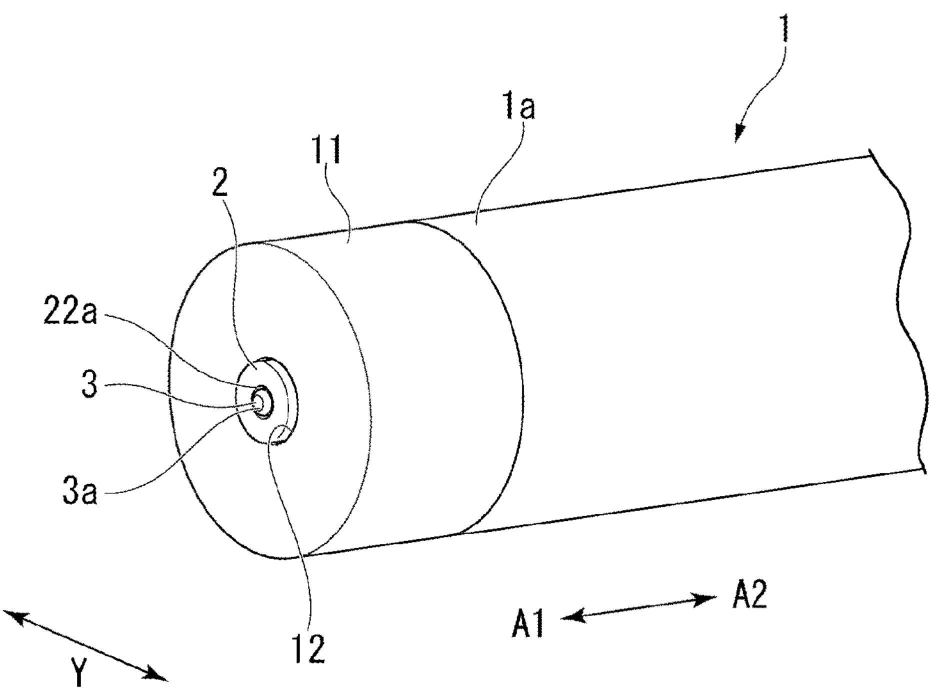
FIG. 5 is a perspective view of the distal end part of the treatment tool in a pre-treatment state.
Figure 6:
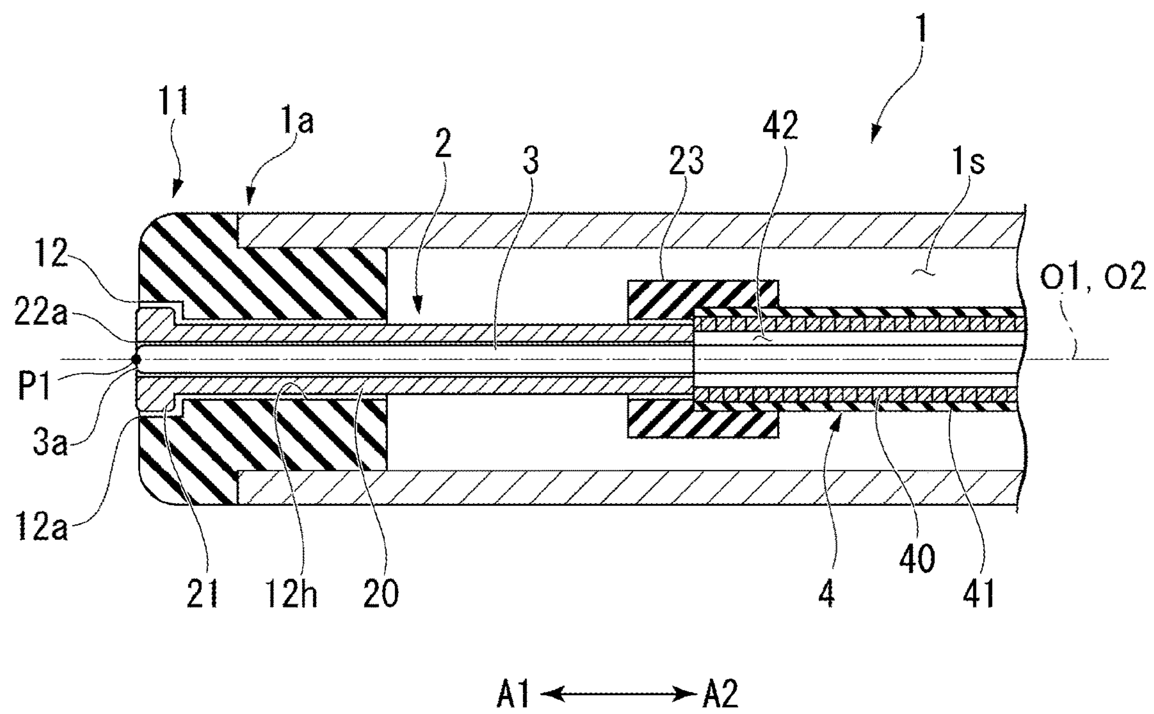
FIG. 6 is a cross-sectional view of the distal end part of the treatment tool in a pre-treatment state.

FIG. 5 is a perspective view illustrating a distal end part of the treatment tool 100 in a pre-treatment state. FIG. 6 is a cross-sectional view illustrating a distal end part of the treatment tool 100 in the pre-treatment state.

As illustrated in FIGS. 5 and 6, when the slider 52 and the lever 55 are moved to the proximal end side A2, the knife 2 and the rod 3 do not protrude from the distal end opening 12*a* of the through-hole 12 of the insulation tip 11 provided at the distal end Ta of the sheath 1. When the knife 2 and the rod 3 move backward, they are housed on the proximal end side A2 from the distal end opening 12*a* of the through-hole 12.

A state of the knife 2 and the rod 3 at this time is defined as a pre-treatment state. Specifically, the pre-treatment state is a state in which the knife 2 is retracted toward the proximal end side A2 and the flange 21 provided at the distal end of the knife main body 20 is arranged near the distal end opening 12*a*. In this state, the flange 21 overlaps the distal end opening 12*a* when viewed from the width direction Y That is, the flange 21 is accommodated in the recess of the insulating tip 11. In a state in which the flange 21 is housed in the recess of the insulation tip 11, the distal end of the knife 2 may slightly protrude from the distal end opening 12*a*. Further, as the knife 2 retreats or retracts, the rod 3 also retreats or retracts toward the proximal end side A2, and the distal end 3*a* of the rod 3 is located in the distal end opening 22*a* of the knife 2 in the longitudinal direction A. That is, the distal end 3*a* is located at the first position P1, and the position of the distal end 3*a* matches the position of the distal end of the knife 2 in the longitudinal direction A. When the position of the distal end of the flange 21 in the longitudinal direction A matches the position of the distal end surface of the insulation tip 11, in the longitudinal direction A, the position of the distal end 3*a* coincides with the position of the distal end surface of the knife 2 and the distal end surface of the insulation tip 11.

Figure 7:
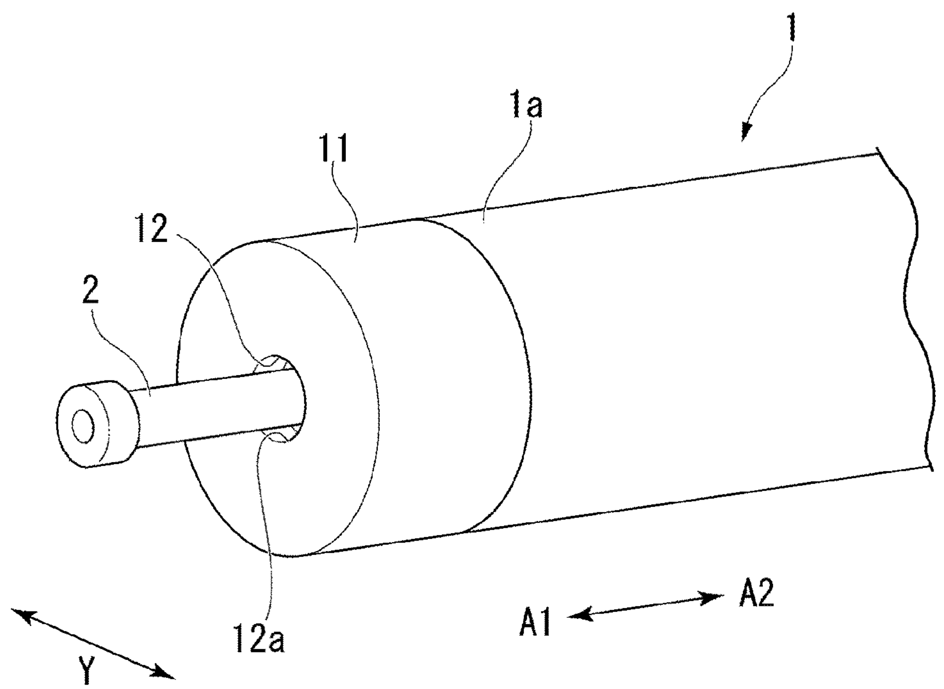
FIG. 7 is a perspective view of the distal end part of the treatment tool in a water supply state.
Figure 8:
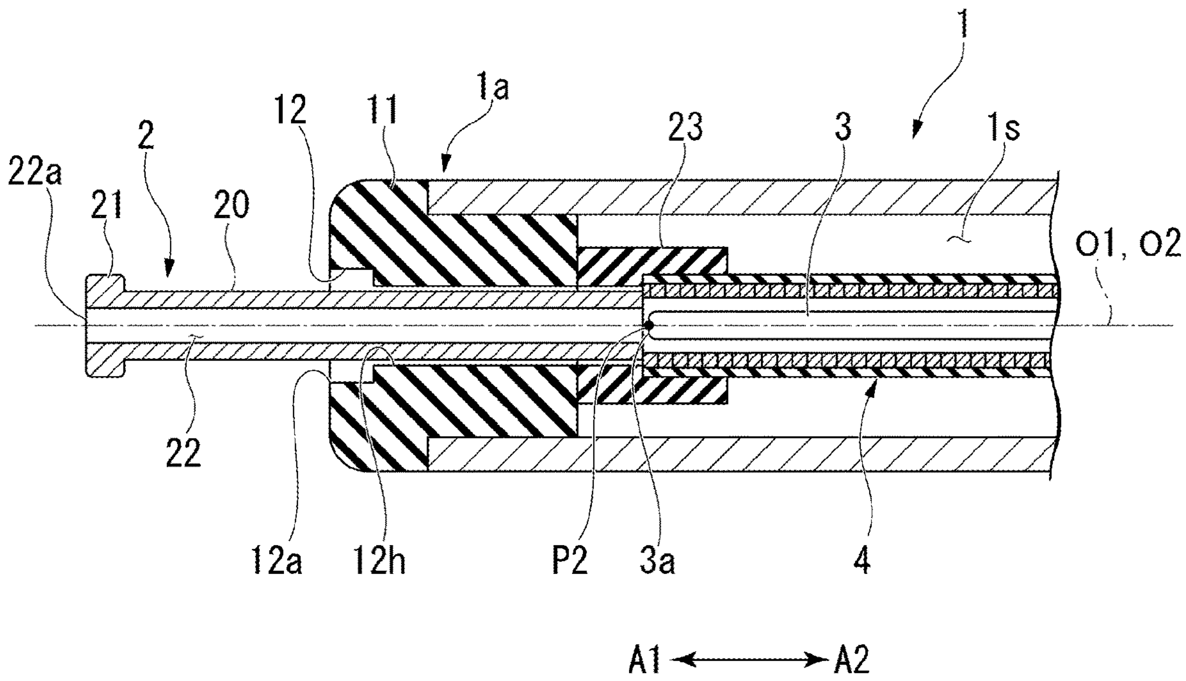
FIG. 8 is a cross-sectional view of the distal end part of the treatment tool in a water supply state.

FIG. 7 is a perspective view illustrating the distal end part of the treatment tool 100 in a water supply state. FIG. 8 is a cross-sectional view illustrating the distal end part of the treatment tool 100 in the water supply state.

As illustrated in FIGS. 7 and 8, when the slider 52 is moved to the distal end side A1, the knife 2 protrudes from the distal end Ta of the sheath 1 (that is, the distal end opening 12*a* of the insulation tip 11). Also, when the lever 55 is further moved to the proximal end side A2, the distal end 3*a* of the rod 3 is disposed at a second position P2 retreated from the first position P1 to the proximal end side A2 and opens the distal end opening 22*a*. A state of the knife 2 and the rod 3 at this time is defined as a water supply state. In the water supply state, the first water supply conduit 22 has a space without insertion of the rod 3, and the first water supply conduit 22 is allowed to supply water. Therefore, in such an example, even when water is supplied, the rod 3 will not interfere, and the distal end 3*a* of the rod 3 does not close the distal end opening 22*a* of the first water supply conduit 22. As a result, the operator can smoothly supply the water and perform a local injection treatment. The form of the rod 3 whose distal end 3*a* is disposed at the second position P2, opens the distal end opening 22*a*, and enables water to be fed through the first conduit 22 is defined as a second configuration.

[Method of Use of Endoscopic Treatment System 300]

Next, a procedure using the endoscopic treatment system 300 (method of use of the endoscopic treatment system 300) of the present embodiment will be described. Specifically, a local injection treatment, incision, cauterization, or peeling treatments, and a hemostasis treatment for a lesion portion (treatment portion) in an endoscopic therapy such as endoscopic submucosal dissection (ESD) will be described.

As preparatory work, the operator identifies a lesion portion using a known method. Specifically, the operator inserts the insertion part 202 of the endoscope 200 into a digestive tract (for, example, esophagus, stomach, duodenum, and large intestine), and identifies a lesion portion while observing an image obtained by the imaging unit 203 of the endoscope.

<Insertion>

The operator may insert the treatment tool 100 into the channel 206 and cause the distal end Ta of the sheath 1 to protrude from the distal end opening 206*a* of the insertion part 202. The operator may cause the slider 52 of the operation unit 5 to move forward relative to the operation unit main body 51 so that the knife 2 and the rod 3 are caused to protrude, thereby becoming the treatment state (see FIGS. 3 and 4).

<Local Injection>

The operator may move the lever 55 to the proximal end side A2 with respect to the slider 52 to move the rod 3 to the proximal end side A2 with respect to the knife 2. Also, the operator may move the slider 52 to the distal end side A1 to cause the knife 2 to protrude from the distal end 1*a* of the sheath 1. As a result, the distal end 3*a* of the rod 3 is disposed at the second position P2 to bring the knife 2 and the rod 3 into the water supply state (see FIGS. 7 and 8). The operator may use the knife 2 to pierce a site of a lesion portion at which a liquid for local injection (local injection liquid) is to be injected and supply water with the distal end opening 22*a* at the distal end of the knife 2 inserted into a submucosal layer (local injection step). In such an example, since the first water supply conduit 22 has a space for a liquid to be supplied, the liquid can flow smoothly inside the first water supply conduit 22 and flows out from the distal end opening 22*a*.

<Incision/Cauterization/Peeling>

The operator may incision, cauterization, or peeling treatments. When the operator moves the lever 55 to the distal end side A1 with respect to the slider 52 while the knife 2 has been moved forward, the rod 3 is caused to protrude from the distal end 1*a* of the sheath 1 to be in the treatment state (see FIGS. 4 and 5). The distal end 3*a* of the rod 3 is positioned at the distal end opening 22*a* in the longitudinal direction A to be disposed at the first position P1. The operator may move the flange 21 to cauterize or incise a mucosa of a lesion portion in a state in which a high-frequency current is applied to the knife 2. Also, the operator may move the knife 2 forward and peel off a submucosal layer of the cauterized or incised lesion portion while lifting the mucosa of the cauterized or incised lesion portion to expose the submucosal layer in a state in which a high-frequency current is applied. At this time, some tissues in the digestive tract can adhere to the distal end of the knife 2. Then, these tissues can become burnt deposits during cauterization and become fixed to the distal end of the knife 2. However, the distal end 3*a* is disposed in the distal end opening 22*a* of the knife 2. Also, the distal end opening 22*a* is covered and closed by the distal end 3*a* of the rod 3 when viewed from the distal end side A1 in the longitudinal direction A. Therefore, the rod 3 can reduce a likelihood that the tissues will adhere to the flange 21 or that the tissues will enter the first water supply conduit 22 from the distal end opening 22*a* to cause clogging thereof. Also, the rod 3 can prevent the tissues adhered during the cauterization treatment from becoming burnt and fixed.

<Removal>

As illustrated in FIGS. 4 and 8, the operator may move the rod 3 forward and backward with respect to the knife 2 by moving the lever 55 forward and backward with respect to the slider 52 to the distal end side A1 and the proximal end side A2. As a result, even if tissues enter the first water supply conduit 22 from the knife main body 20 and the distal end opening 22*a* of the knife 2 due to the above-described incision, cauterization, or peeling treatments, and burnt deposits of tissues become fixed to the distal end opening 22*a* and the knife main body 20, the distal end 3*a* of the rod 3 can peel off and remove the burnt deposits of tissues.

<Additional Local Injection>

The operator may perform an additional local injection treatment as necessary. The operator may move the rod 3 backward to the proximal end side A2 with respect to the knife 2 to bring the rod 3 into the water supply state (see FIGS. 7 and 8). The operator may insert the distal end opening 22*a* at the distal end of the knife 2 into a submucosal layer at a site at which a liquid for local injection (local injection liquid) is to be additionally injected to supply water (additional local injection step). In such an example, the distal end 3*a* of the rod 3 is disposed at the second position P2, and the first water supply conduit 22 has a space for a liquid to be supplied. Therefore, the liquid can flow smoothly inside the first water supply conduit 22 and flows out from the distal end opening 22*a*.

<Hemostasis>

In a case of bleeding during incision, cauterization, or peeling treatments, the operator may perform a hemostasis treatment. The operator may introduce the knife 2 and the rod 3 into the treatment state, and cauterize a bleeding point by applying a high-frequency current while pressing the knife main body 20 and flange 21 to the treatment site to stop the bleeding (hemostasis step).

The operator may continue the above-described operation (treatment) as necessary, and finally excises the lesion portion to end the ESD procedure.

According to the treatment tool 100 of the present embodiment, a plurality of treatments such as local injection treatment, incision, cauterization, or peeling treatments, and a hemostasis treatment can be performed.

The treatment tool 100 according to the present embodiment may further include the rod 3. Therefore, even if burnt deposits of tissues enter the distal end of the knife 2 and the first water supply conduit 22 due to the incision, cauterization, or peeling treatments become fixed, the rod 3 can peel off and remove the burnt deposits of tissues. Further, the rod 3 can physically remove burnt deposits of tissues. Therefore, the operator no longer needs to perform an operation (treatment) of removing burnt deposits of tissues by supplying high-pressure water.

The rod 3 according to the present embodiment may move forward and backward in the longitudinal direction A. Therefore, at the time of a local injection treatment, when the operator may move the lever 55 backward to the proximal end side A2 with respect to the slider 52 and move the rod 3 to the proximal end side A2 to dispose the rod 3 at the second position, a space is provided in the first water supply conduit 22 through which a liquid to be supplied flows, and the liquid can be caused to smoothly flow out from the distal end opening 22*a*.

The rod 3 according to the present embodiment may close the distal end opening 22*a* of the first water supply conduit 22 on the distal end side A1. Therefore, the rod 3 can prevent tissue from entering the first water supply conduit 22 from the distal end opening 22*a* during incision/cauterization/peeling treatments.

Figure 9:
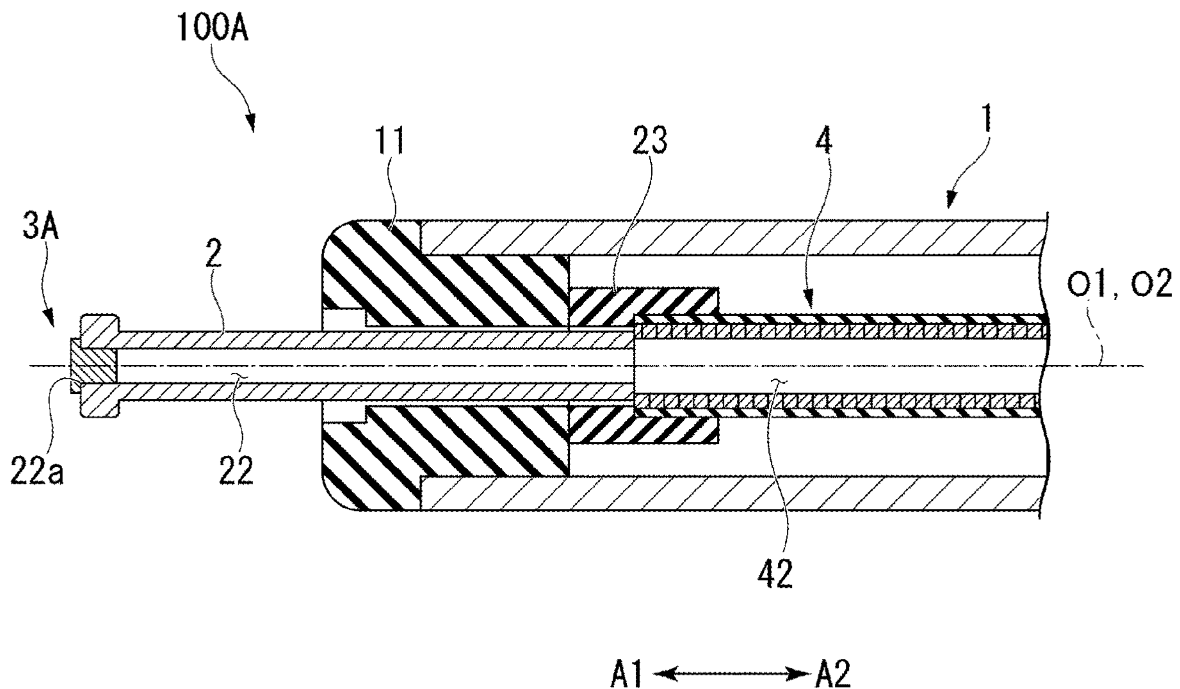
FIG. 9 is a cross-sectional view of a sealing member of a treatment tool which is a modified example of the rod of the treatment tool.

In the above-described embodiment, the rod 3 is inserted through the knife 2 and the operation wire 4. However, an aspect of the rod 3 is not limited thereto. FIG. 9 is a view illustrating a sealing member 3A (e.g., a plug) of a treatment tool 100A which may be a modified example of the rod 3 of the treatment tool 100. The sealing member 3A may have a smaller length in the longitudinal direction A compared to the rod 3 of the first embodiment. Specifically, the length of the sealing member 3A may be smaller than a length of the knife 2 in the longitudinal direction A. In the present embodiment, the sealing member 3A may be a lid having insulating properties that is inserted into the first water supply conduit 22 of the knife 2 to close the distal end opening 22*a* at the distal end of the knife 2 as illustrated in FIG. 9. In an example, the sealing member 3A may be removable.

In such an example, the sealing member 3A can close the distal end opening 22*a* at the distal end of the knife 2.

Therefore, in the incision, cauterization, or peeling step described above, it is possible to prevent tissues or burnt deposits of tissue from adhering to the distal end of the knife 2. As an assumption, even if tissues adhere to the distal end of the knife 2, since the sealing member 3A is removable, the operator can peel off and remove the tissues or burnt deposits of tissues by removing the sealing member 3A from the distal end opening 22*a*.

Further, the sealing member 3A may further have a through-hole penetrating in the longitudinal direction A in the vicinity of a center thereof. With this configuration, the treatment tool 100A can supply a liquid from the through-hole of the sealing member 3A with the sealing member 3A attached to the distal end opening 22*a*. Therefore, the treatment tool 100A can supply water while preventing tissues or burnt deposits of tissues from adhering.

Figure 10:
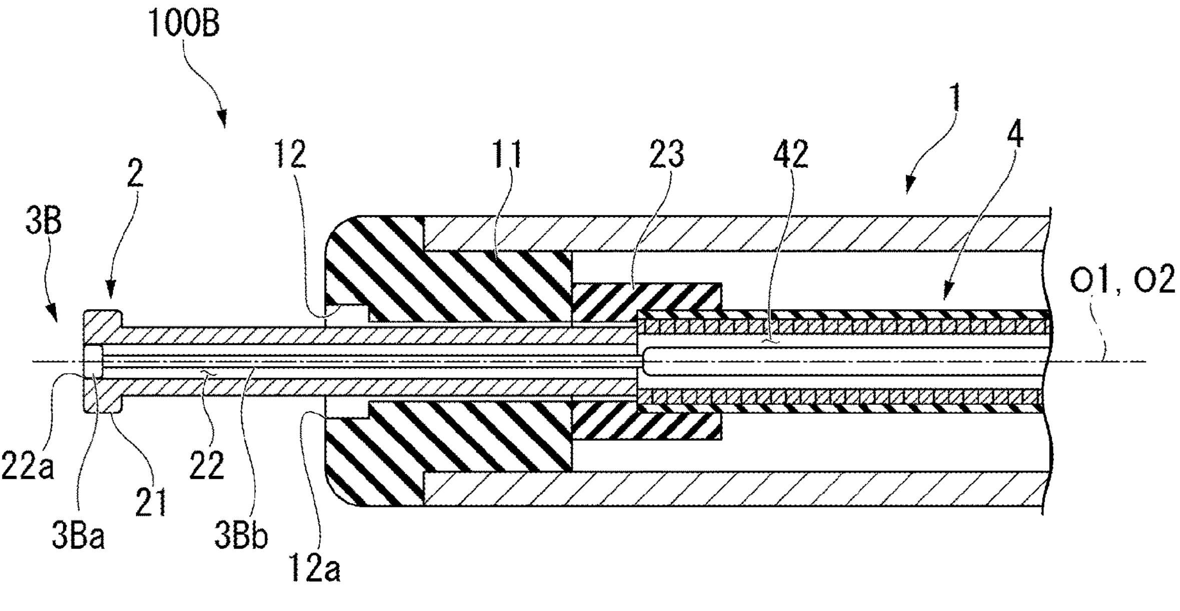
FIG. 10 is a cross-sectional view of a rod of a treatment tool which is a modified example of the rod of the treatment tool.
Figure 11:
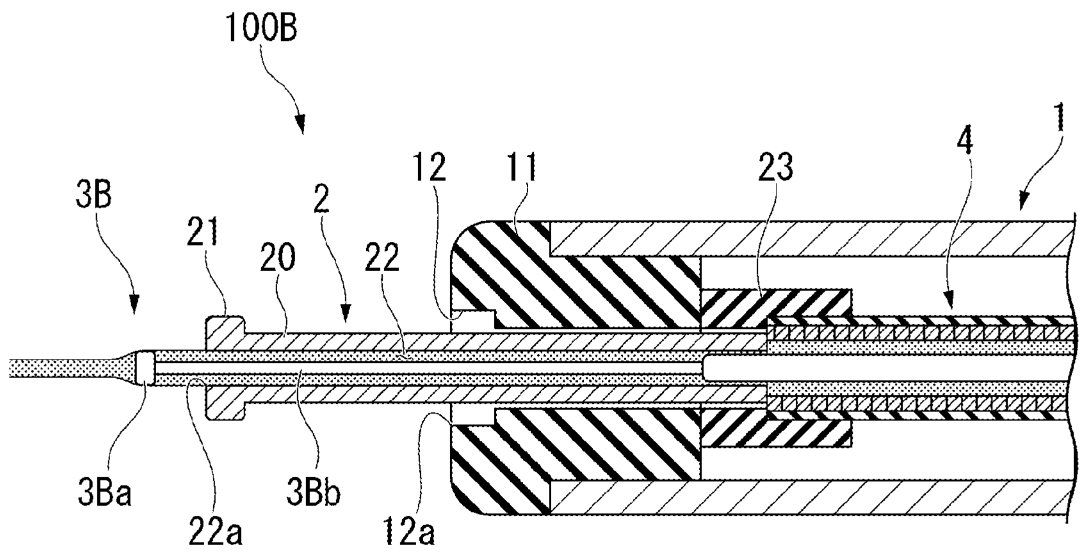
FIG. 11 is a cross-sectional view of a state in which the rod has moved forward.

In the above-described embodiment, the rod 3 is a round rod-shaped member extending in the longitudinal direction A. However, an aspect of the rod 3 is not limited thereto. FIG. 10 is a view illustrating a rod 3B of a treatment tool 100B that is a modified example of the rod 3 of the treatment tool 100. FIG. 11 is a view illustrating a state in which the rod 3B has moved forward.

As illustrated in FIG. 10, the rod 3B includes a support column part 3Bb extending in the longitudinal direction A with the central axis O2 as a central axis, and a distal end part (sealing member) 3Ba provided on the distal end side A1 of the support column part 3Bb and having an outer diameter larger than that of the support column part 3Bb. The proximal end side A2 of the support column part 3Bb is connected to the lever 55 of the operation unit 5 to be described later. An outer diameter of the distal end part 3Ba may be slightly smaller than an inner diameter of the distal end opening 22*a*. The distal end part 3Ba of the rod 3B may cover and close (e.g., seal) the distal end opening 22*a* at the first position P1 disposed at the distal end opening 22*a*. In this state, the operator can perform incision, cauterization, or peeling treatments. Also in this case, since the distal end opening 22*a* may be closed (sealed) by the distal end part 3Ba of the rod 3B, it is possible to prevent tissues from entering the first water supply conduit 22 from the flange 21 or the distal end opening 22*a* and adhering to the knife main body 20, or prevent burnt deposits of tissues from becoming fixed.

Also, as illustrated in FIG. 11, when the operator moves the lever 55 of the operation unit 5 forward, the support column part 3Bb moves forward to the distal end side A1. The distal end part 3Ba moves to the distal end side A1 with respect to the distal end opening 22*a* of the first water supply conduit 22 on the distal end side A1. Then, the distal end opening 22*a*, which has been covered and closed by the distal end part 3Ba of the rod 3B, opens. Therefore, in this state, the operator can smoothly supply a liquid to perform a local injection treatment.

Figure 12:
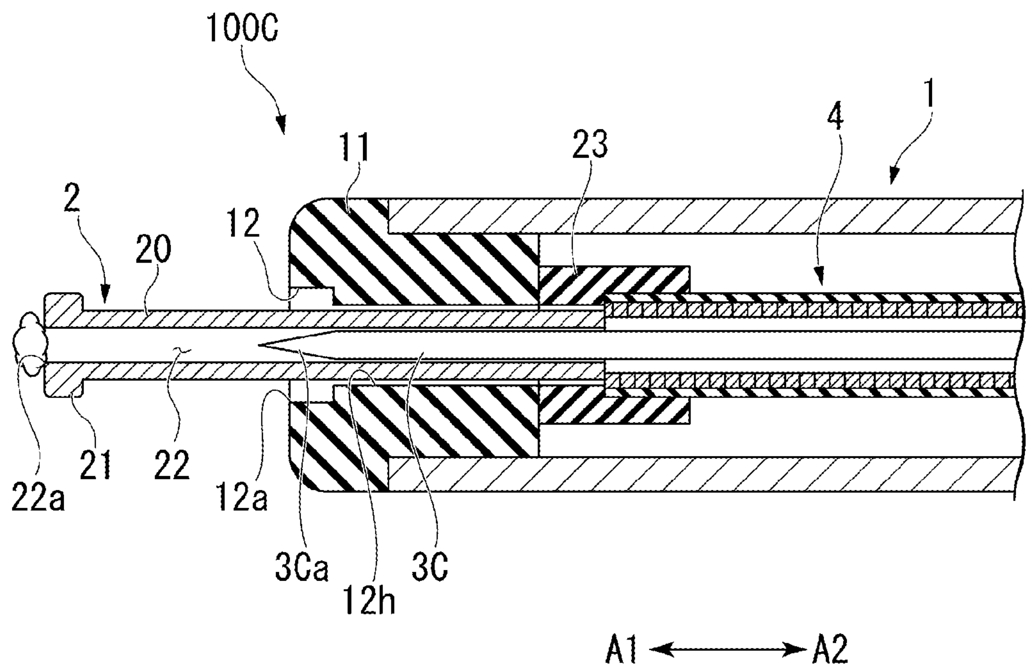
FIG. 12 is a cross-sectional view of a rod of a treatment tool which is a modified example of the rod of the treatment tool.
Figure 13:
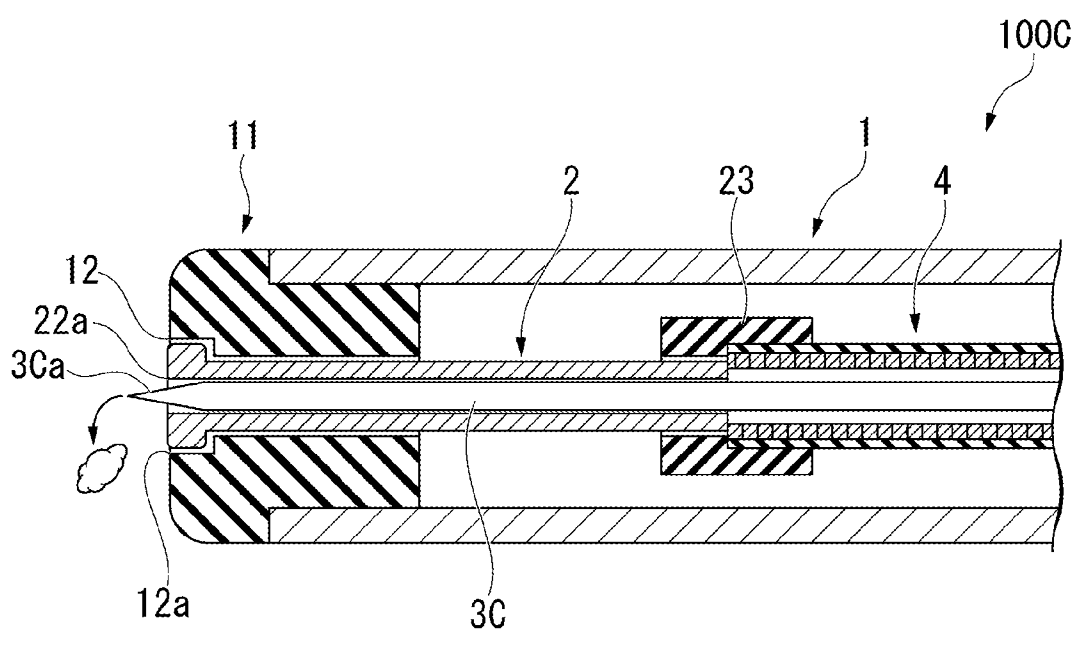
FIG. 13 is a cross-sectional view of a state in which a knife of the treatment tool has been moved.

FIG. 12 is a view illustrating a rod 3C of a treatment tool 100C which is a modified example of the rod 3 of the treatment tool 100. FIG. 13 is a view illustrating a state in which the knife 2 of the treatment tool 100C has been moved.

A distal end 3Ca of the rod 3C may include a tapered surface such that the distal end becomes sharp, and may be formed such that the outer diameter becomes smaller from the proximal end toward the distal end of the tapered surface. As illustrated in FIG. 12, the distal end part 3Ca of the rod 3C may be disposed to slightly protrude toward the distal end side A1 with respect to the distal end opening 12*a* of the tip conduit 12*h*. In such an example, the operation unit 5 may not include the lever 55. The rod 3C does not move forward and backward in the longitudinal direction A, and a proximal end side of the rod 3C is fixed to a part of the operation unit main body 51.

In order to perform incision, cauterization, or peeling treatments, the operator may move the slider 52 to the distal end side A1 to cause the knife 2 to protrude from the distal end opening 12*a* as illustrated in FIG. 12. When the incision, cauterization, or peeling treatments are performed in this state, some tissues in the digestive tract may adhere and become fixed to the distal end of the knife 2. However, as illustrated in FIG. 13, when the operator moves the slider 52 to the proximal end side A2 to move the knife 2 backward to the vicinity of the distal end opening 12*a*, the distal end part 3Ca slightly protruding toward the distal end side A1 from the distal end opening 12*a* may pierce the burnt deposits of the tissues adhered to the distal end of the knife 2, and can be peeled off and removed.

Further, the operation unit 5 may include the lever 55. In this case, the operator may move the lever 55 to the distal end side A1 in the longitudinal direction A to cause the rod 3 to protrude from the distal end opening 12*a* and the distal end opening 22*a* of the knife 2. In this state, the rod 3 can use the distal end part 3Ca to pierce a site at which a liquid for local injection is to be injected and easily insert the distal end opening 22*a* at the distal end of the knife 2 into the submucosal layer.

The distal end part 3Ca may not be inclined toward the central axis O2. For example, the distal end part 3Ca may be formed in a shape that is inclined toward an axis in the longitudinal direction A passing through one end of a circumferential edge of the rod 3 from the proximal end side A2 to the distal end side A1.

In the above-described embodiment, the slider 52 and the lever 55 are not directly connected in the operation unit 5, but an aspect of the operation unit 5 is not limited thereto. In the operation unit 5, the slider 52 and the lever 55 may be directly connected. In this case, due to the friction between the slider 52 and the lever 55, etc., when the slider 52 is moved forward or backward, the rod 3, the operation wire 4, and the knife 2 can be operated in conjunction with each other.

In the above-described embodiment, the operation unit 5 may further include a removable stopper that locks the lever 55. In such an example, the lever 55 can be locked to the stopper to stop the forward and backward movement, and unintentional movement of the rod 3 forward and backward with respect to the knife 2 can be suppressed, inhibited, or prevented.

Figure 14:
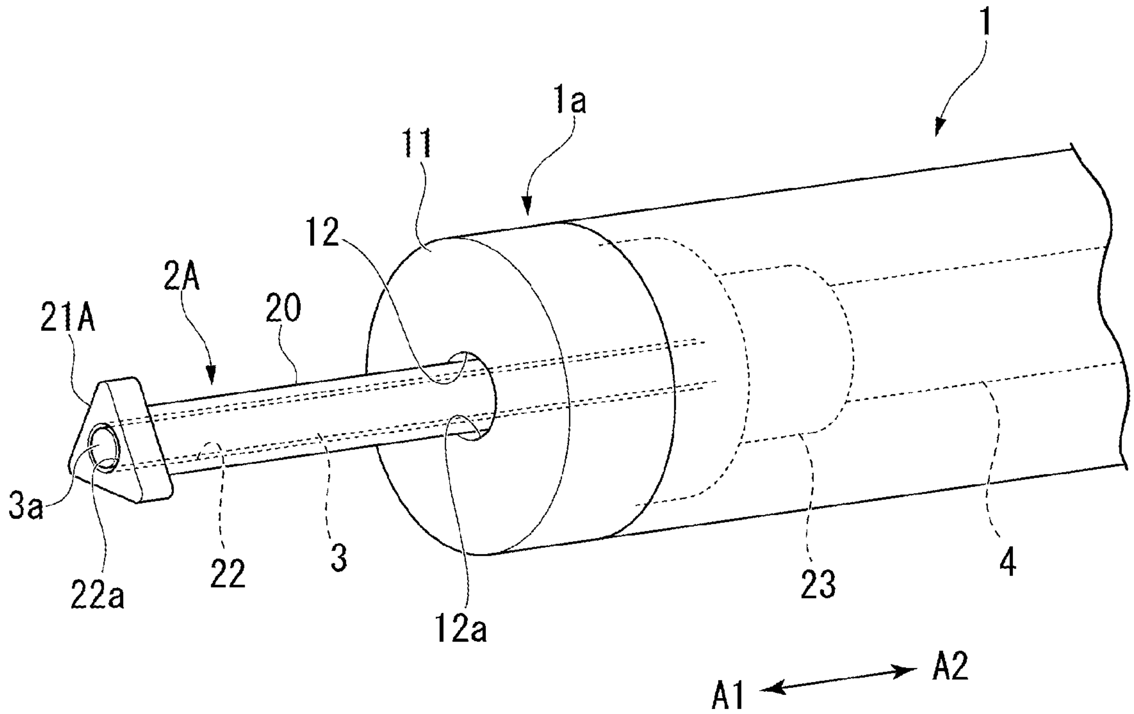
FIG. 14 is a perspective view of a modified example of the knife.

In the above-described embodiment, a disc-shaped flange 21 may be provided at the distal end of the knife 2. However, an aspect of the knife 2 is not limited thereto. FIG. 14 is a view illustrating a knife 2A which is a modified example of the knife 2. A flange 21A of the knife 2A may have a triangular shape in a front view from the distal end side A1. According to this configuration, the operator can incise tissues without slipping by hooking each vertex of the triangular shape without an operation of rotating the knife 2 in a circumferential direction.

Figure 15:
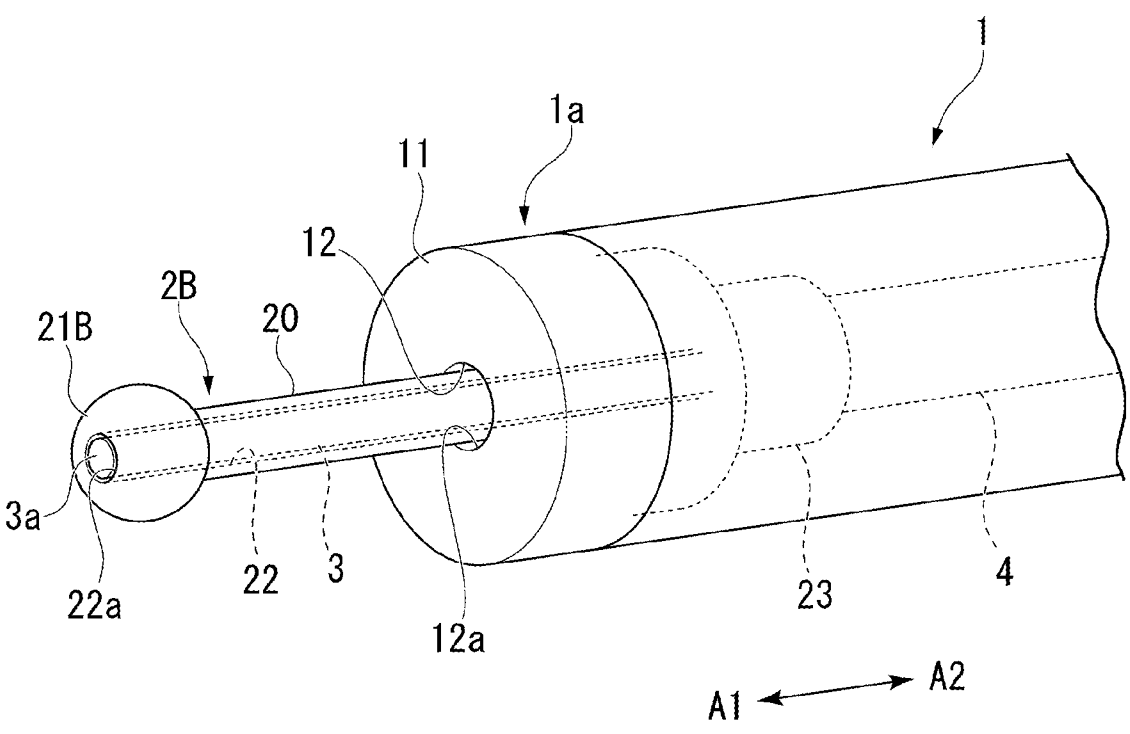
FIG. 15 is a perspective view of a modified example of the knife.

In the above-described embodiment, the flange 21 is provided at the distal end of the knife 2. However, an aspect of the knife 2 is not limited thereto. FIG. 15 is a view illustrating a knife 2B which is a modified example of the knife 2. A distal end part 21B of the knife 2B may have a different shape from the flange 21 and may be formed in a spherical shape. With this configuration, the distal end part 21B of the knife 2B can easily penetrate into the submucosal layer, allowing the operator to perform efficient procedures. Also, the operator can perform mucosal incision operations while minimizing invasion into deep tissues by using the distal end part 21B of the knife 2B.

In the above-described embodiment, the treatment tool 100 includes the distal end opening 22*a* of the knife 2 as a water supply port, but an aspect of the treatment tool 100 is not limited thereto. The treatment tool 100 may further have a through-hole (first conduit) for water supply in the insulation tip 11 of the sheath 1. Also, the treatment tool 100 may further include a water supply tube for water supply in the internal space is of the sheath 1.

In the above embodiment, the operation unit 5 may further include a regulating member (stopper) that regulates the range of movement of the lever 55.

Figure 16:
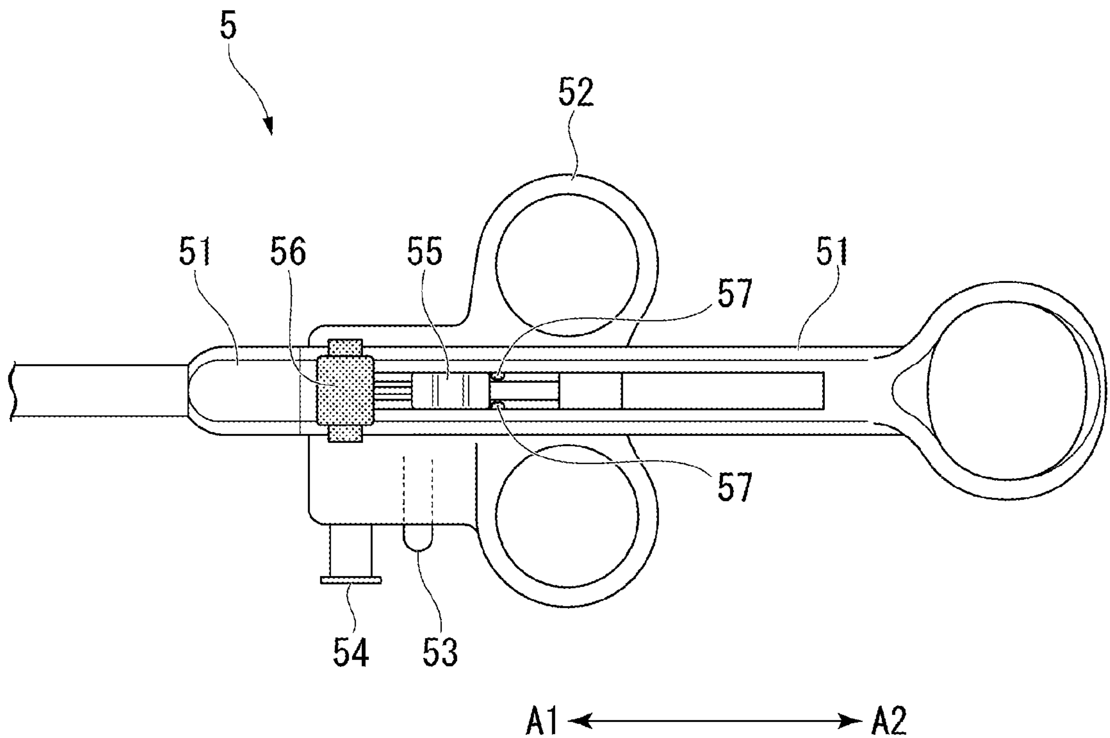
FIG. 16 is a view showing a modified example of the operation unit of the treatment instrument in a closed state.
Figure 17:
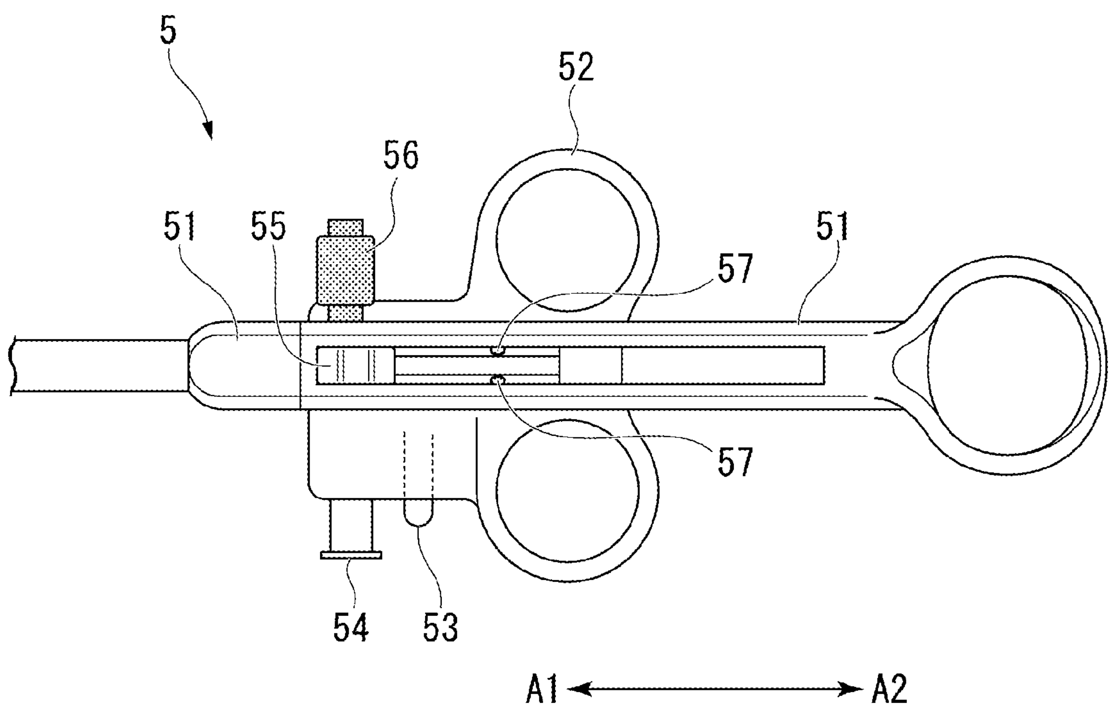
FIG. 17 is a view showing an open state of a modified example of the operation unit of the treatment tool.
Figure 18:
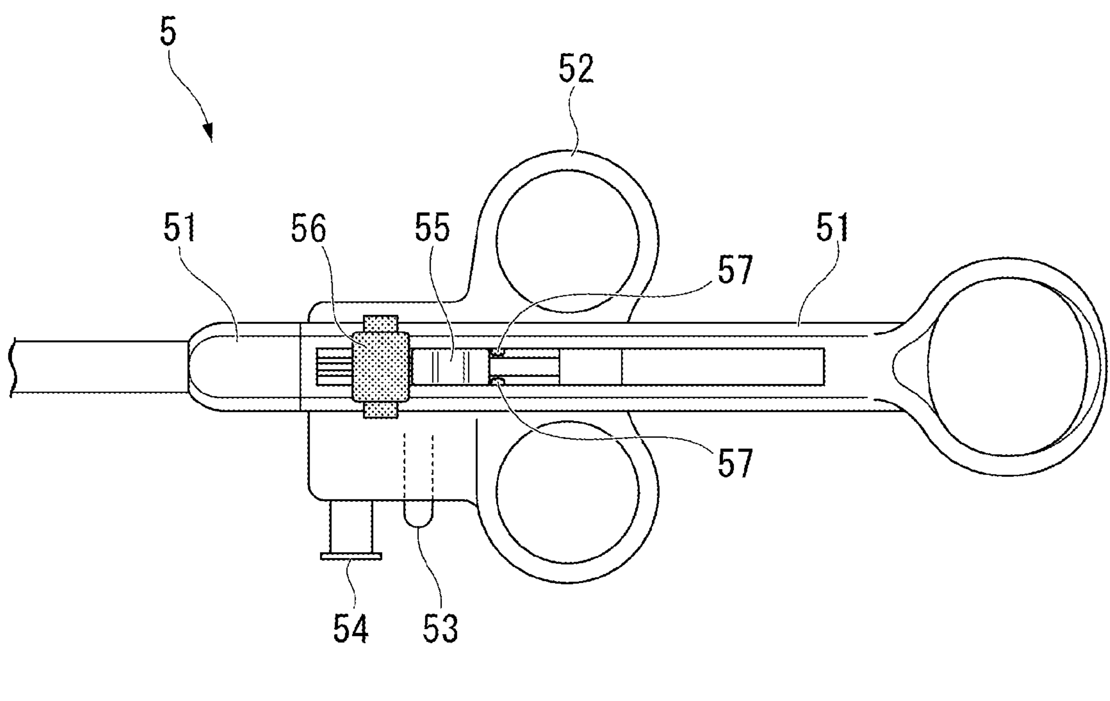
FIG. 18 is a view showing a modified example of the operation unit of the treatment tool in a closed state.

FIG. 16 is a diagram showing a modified example of the operation unit 5 including the regulating member 56 in a closed state. FIG. 17 is a diagram showing a modified example of the operation unit 5 including the regulating member 56 in an open state. FIG. 18 is a diagram showing a modified example of the operation unit 5 including the regulating member 56 in a closed state.

The regulating member 56 (stopper) may be removably provided on the operation unit main body 51. Further, the regulating member 56 may be provided on the distal end side A1 of the lever 55 and can regulate the movement of the lever 55 toward the distal end side A1.

The operation unit 5 may further include a regulating protrusion 57 capable of regulating the movement of the lever 55 toward the proximal end side A2. As shown in FIGS. 16, 17, and 18, the regulating protrusion 57 includes a protrusion shape that is provided on the proximal end side A2 of the operation unit main body 51 rather than the lever 55.

As shown in FIG. 16, a state in which the regulating member 56 of the operation unit 5 regulates the movement of the lever 55 toward the distal end side A1 is referred to as a "closed state." In the operation unit 5 in the closed state, movement of the distal end side A1 of the lever 55 may be regulated by a regulating member 56. Further, movement of the proximal end side A2 of the lever 55 is regulated by a regulating protrusion 57. That is, the regulating member 56 and the regulating protrusion 57 are stoppers that may be used or configured to regulate the range of movement of the lever 55.

In the operation unit 5 in the closed state shown in FIG. 16, the lever 55 can move forward and backward in the longitudinal direction A within a predetermined range. The range in which the lever 55 can move forward and backward is the range sandwiched between the regulating member 56 and the regulating protrusion 57 in the longitudinal direction A.

Since the proximal end of the rod 3 is connected to the lever 55, by limiting the range of movement of the lever 55 by the regulating member 56 and the regulation protrusion 57, the range of movement of the rod 3 in the longitudinal direction A is also limited.

When the range of movement of the lever 55 is limited by the regulating member 56 and the regulation protrusion 57, the range of movement of the lever 55 in the longitudinal direction A of the distal end 3*a* of the rod 3 is limited to the range from the first position P1 (see FIGS. 4 and 6) where the distal end 3*a* is located in the distal end opening 22*a* to the proximal end of the knife 2 (for example, the second position P2 shown in FIG. 8). Here, the state of the rod 3 in which the range in which the distal end 3*a* can move forward and backward is regulated to the range from the first position P1 to the position of the proximal end of the knife 2 is referred to as a "regulated state."

In an example, the operator can easily move the distal end 3*a* of the rod 3 back and forth between the first position P1 and the second position P2 by moving the lever 55 back and forth within the range from the regulation member 56 to the regulation protrusion 57. Therefore, when tissue enters the first water supply conduit 22 and the burnt deposits of the tissues adhere to the inside of the first water supply conduit 22, the operator may move the lever 55 back and forth within the range from the regulating member 56 to the regulating protrusion 57. By moving the rod 3 back and forth in the range from the first position P1 to the second position P2, the burnt deposits of the tissues can be easily peeled off and removed by the rod 3. The operator can peel off the burnt deposits of the tissues adhered inside the first water pipe 22 by using the distal end 3*a* of the rod 3 in the above embodiment or the distal end 3Ba shown in FIG. 10.

Furthermore, as shown in FIG. 17, by removing the regulating member 56 from the operation unit main body 51, the regulation of movement of the lever 55 by the regulating member 56 can be released. Here, the state of the operation unit 5 in which the movement of the lever 55 toward the distal end side A1 is not regulated by the regulating member 56 is referred to as an "open state."

When the operation unit 5 is in the open state, the lever 55 can move toward the distal end side A1 without being hindered by the regulating member 56, as shown in FIG. 18. Therefore, the operator can move the distal end 3*a* of the rod 3 from the first position P1 to the distal end side A1 by moving the lever 55 of the operation unit 5 forward. Here, the state of the rod 3 in which the distal end 3*a* is protruded from the first position P1 toward the distal end side A1 is referred to as a "protruding state." When the operation unit 5 is in the open state and the rod 3 is in the protruding state, the distal end 3Ba of the rod 3B shown in FIG. 11 can be moved from the distal end opening 22*a* of the distal end side A1 of the first water supply pipe 22 to the distal end side A1, and local injection treatment can be performed.

As shown in FIG. 18, the operation unit 5 may be configured such that the lever 55 cannot be moved forward or backward by the regulating member 56 and the regulating protrusion 57. The lever 55 shown in FIG. 18 may be regulated from moving toward the distal end side A1 by the regulating member 56, and from moving toward the proximal end side A2 by the regulating protrusion 57, and may be provided so as not to move forward or backward in the longitudinal direction A. The regulating member 56 shown in FIG. 18 may be provided closer to the proximal end side A2 than the regulating member 56 shown in FIG. 16.

When the lever 55 is regulated from moving forward or backward by the regulating member 56 and the regulating protrusion 57, the distal end 3*a* of the rod 3 is disposed at the first position P1. That is, since the distal end opening 22*a* of the knife 2 is covered and closed by the distal end 3*a* of the rod 3, tissue can be prevented from entering the first water supply conduit 22 through the distal end opening 22*a* and clogging it.

The state of the rod 3 in which the distal end 3*a* is positioned at the first position P1 by regulating the forward and backward movement of the lever 55 by the regulating member 56 and the regulating protrusion 57 is referred to as a "positioning state". The operator may easily maintain the rod 3 in a positioning state by regulating the forward and backward movement of the lever 55 using the regulating member 56 and the regulating protrusion 57.

The regulating member 56 that is removably attached to the operation unit main body 51 does not have to be separated from the operation unit main body 51 when the operation unit 5 is in the open state. For example, the first end of the regulating member 56 may be rotatably attached to the operation unit main body 51, and the second end of the regulating member 56 may be detachably attached to the operation unit main body 51. In that case, the operation unit 5 may be switched between the open state and the closed state by rotating the regulating member 56 with respect to the operation unit main body 51.

The regulating protrusion 57 that regulates the movement of the lever 55 toward the proximal end side A2 may be removably provided on the operation unit main body 51. Furthermore, in the examples shown in FIGS. 16, 17, and 18, the operation unit 5 may be provided with two regulating protrusions 57. For example, the movement of the lever 55 toward the proximal end side A2 may be regulated by one regulating protrusion 57.

In the above embodiment, the rod 3 may include a protrusion (burnt deposits-removing part) protruding from the outer circumferential surface of the rod 3.

Figure 19:
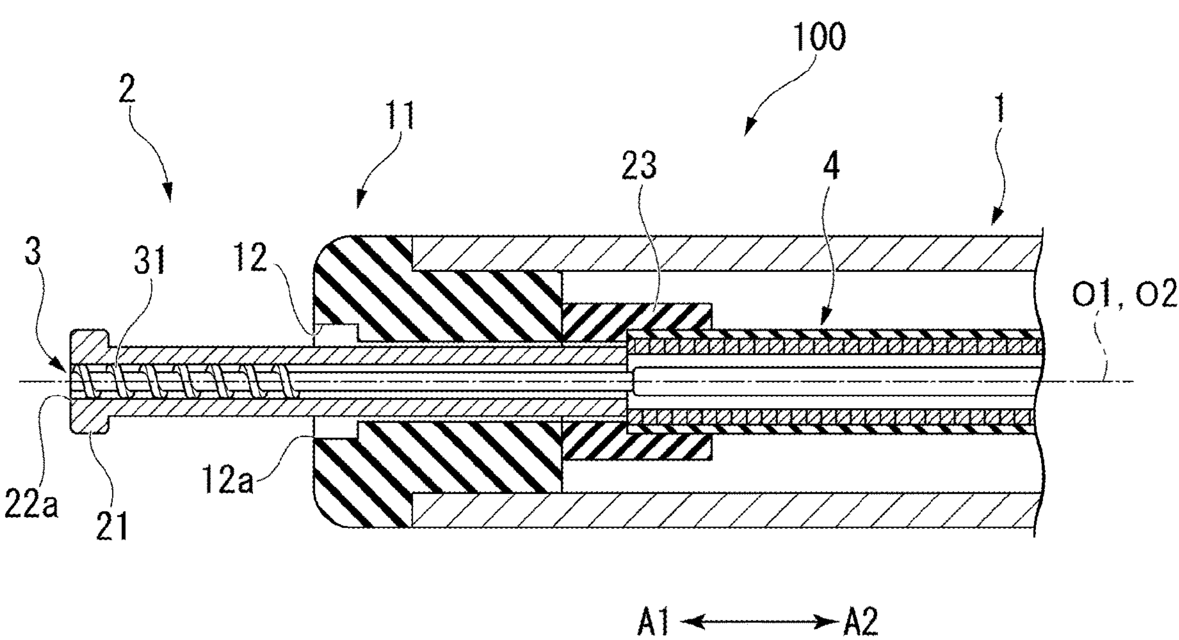
FIG. 19 is a sectional view showing a modification of the rod.

FIG. 19 is a sectional view showing a modified example of the rod 3. The rod 3 shown in FIG. 19 may be provided with a spiral protrusion 31 that may be provided on the outer peripheral surface of the rod 3 and protrudes outward in the radial direction of the rod 3. Here, the outer side in the radial direction of the rod 3 refers to the direction away from the central axis O2 of the rod 3 in the radial direction of the rod 3.

As shown in FIG. 19, the spiral protrusion 31 may be spirally provided in a predetermined range in the longitudinal direction A on the outer peripheral surface of the rod 3. The outer diameter of the spiral protrusion 31 may be slightly smaller than the inner diameter of the distal end opening 22*a*.

The operator can peel off the burnt deposits of the tissues adhered inside the first water supply conduit 22 using the spiral protrusion 31, by moving the lever 55 back and forth and for example, moving the rod 3 back and forth in the range from the first position P1 to the second position P2.

The protrusion is not limited to a spiral shape, but any shape of protrusion, such as a flap or a wing, may be provided on the outer peripheral surface of the rod 3. The outer circumferential surface of the rod 3 may have the function of removing burnt deposits of the tissues.

In the above embodiment, the rod 3 can move forward and backward in the longitudinal direction A by moving the lever 55 forward and backward, but the aspect of the rod 3 is not limited to this.

Figure 20:
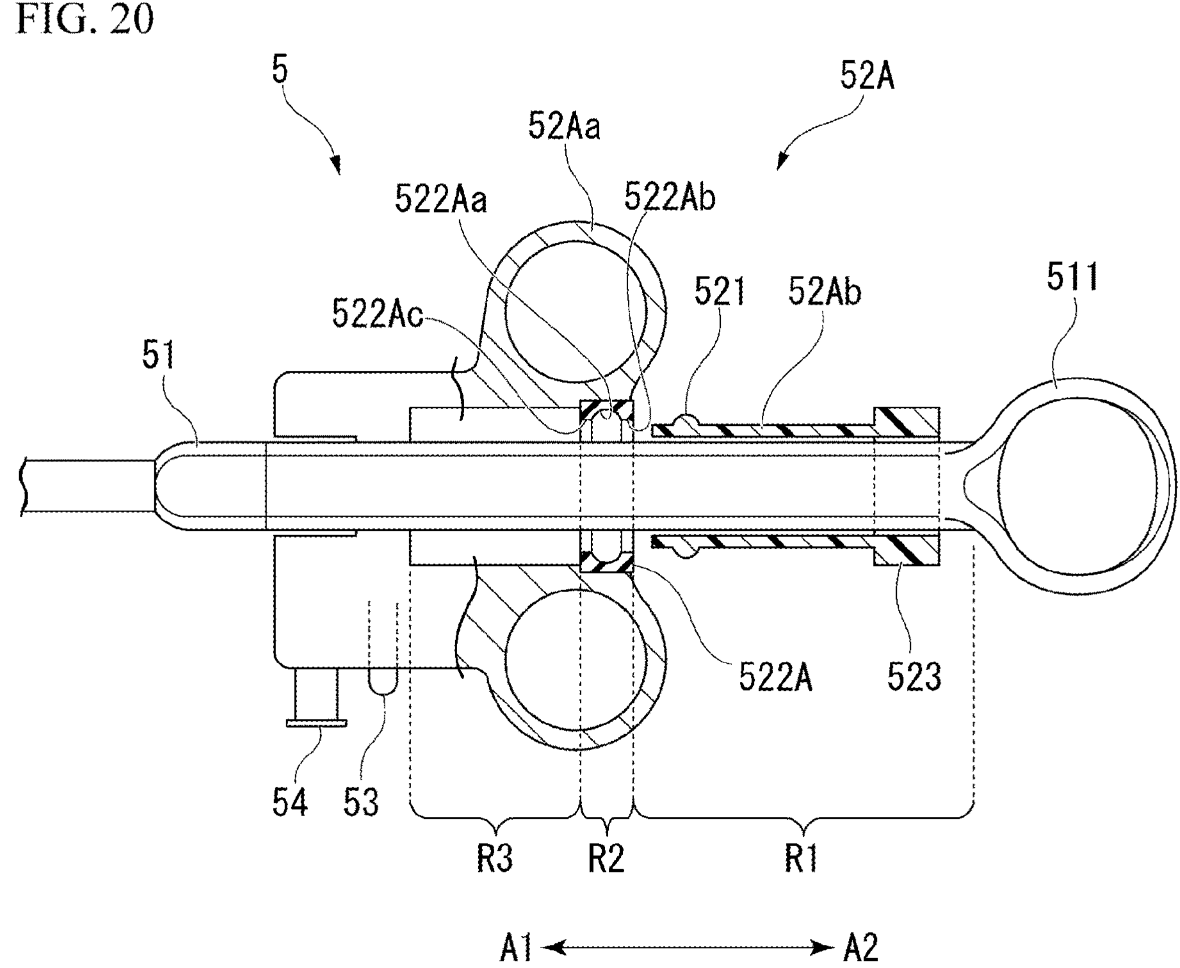
FIG. 20 is a sectional view showing a rod slider located in a first region in a modified example of the operation unit.
Figure 21:
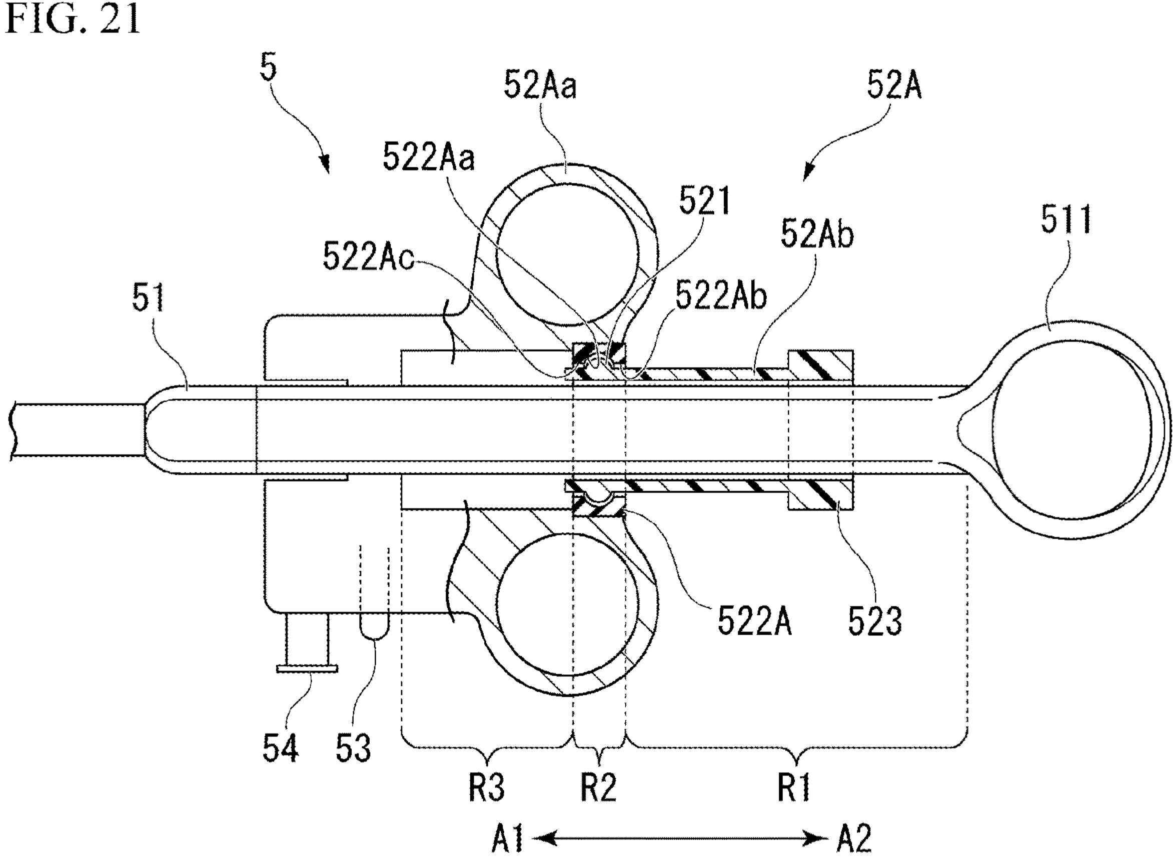
FIG. 21 is a cross-sectional view showing a rod slider located in a second region in a modification of the operation unit.
Figure 22:
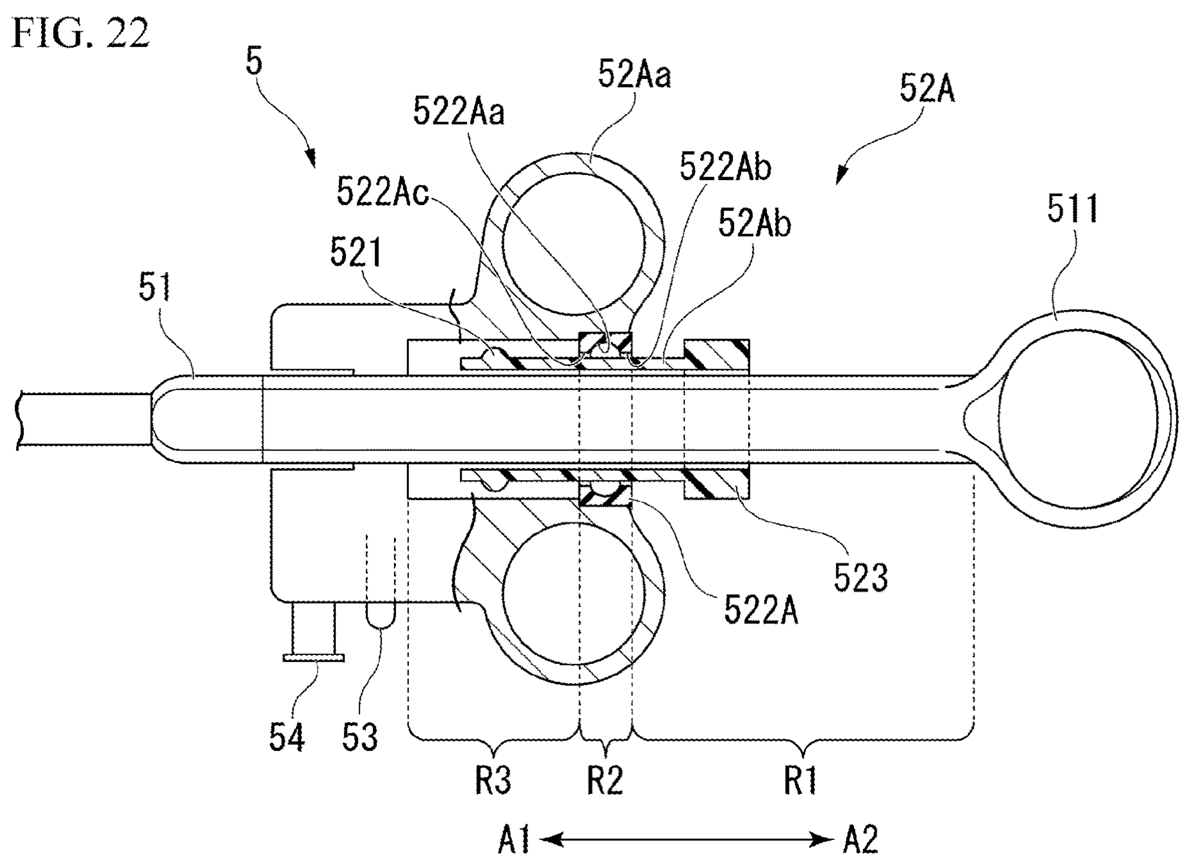
FIG. 22 is a sectional view showing a rod slider located in a third region in a modification of the operation unit.

FIG. 20 is a cross-sectional view showing a rod slider 52Ab located in the first region R1 in a modified example of the operation unit 5. FIG. 21 is a sectional view showing the rod slider 52Ab located in the second region R2. FIG. 22 is a sectional view showing the rod slider 52Ab located in the third region R3.

In the modified example shown in FIGS. 20, 21, and 22, the slider 52A may include a knife slider 52A (a first slider) and a rod slider 52Ab (second slider, slide lever).

Like the slider 52 in the above embodiment, the knife slider 52Aa may be attached to the proximal end of the operating wire 4, and may be configured to be able to move the operating wire 4 and knife 2 forward and backward by moving it forward and backward relative to the operation unit main body 51.

The rod slider 52Ab may be attached to the proximal end of the rod 3, and may be configured to move the rod 3 forward and backward by moving it forward and backward relative to the operation unit main body 51 and the knife slider 52Aa. That is, the operator can advance and retreat the operating wire 4 and knife 2 by advancing and retreating the knife slider 52Aa, and can advance and retreat the rod 3 by advancing and retreating the rod slider 52Ab.

The rod slider 52Ab may be a cylindrical member through which the operation unit main body 51 is inserted. The shape, however, does not necessarily have to be strictly cylindrical. A positioning portion 521 that protrudes outward from the outer peripheral surface is provided at the distal end of the rod slider 52Ab.

The positioning portion 521 may be provided on the entire outer periphery of the rod slider 52Ab or may be provided only on a portion thereof. When the positioning portions 521 are provided only on a portion of the outer periphery of the rod slider 52Ab, the positioning portions 521 may be provided at multiple locations on the outer periphery of the rod slider 52Ab.

Furthermore, as shown in FIG. 20, a cylindrical slider-regulating 522A portion (e.g., a stopper) through which the operation unit main body 51 may be inserted is provided at the proximal end of the knife slider 52Aa.

A slider recess 522Aa whose inner peripheral surface may be more concave than a proximal end 522Ab and a distal end 522Ac of the slider-regulating portion 522A may be provided on the inner periphery of the slider-regulating portion 522A. The slider recess 522Aa is, for example, a portion whose entire circumference is concave in the inner circumference of the slider-regulating portion 522A.

The proximal end side A2 of the slider-regulating portion 522A is referred to as a "first region R1." That is, the rod slider 52Ab shown in FIG. 20 may be located in the first region R1. Further, in the longitudinal direction A, the region where the slider-regulating portion 522A is provided is referred to as a "second region R2." In the rod slider 52Ab shown in FIG. 21, the positioning portion 521 may be located in the second region R2.

When the positioning portion 521 is located in the second region R2, the convex positioning portion 521 and the concave slider recess 522Aa fit together, and movement of the rod slider 52Ab in the longitudinal direction A may be regulated by the slider-regulating portion 522A. The inner diameters of the proximal end 522Ab and the distal end 522Ac of the slider-regulating portion 522A may be smaller than the outer diameter of the positioning portion 521. Therefore, the positioning portion 521 may be "sandwiched" or located between the proximal end 522Ab and the distal end 522Ac of the slider-regulating portion 522A in the longitudinal direction A, and movement of the positioning portion 521 in the longitudinal direction A is regulated.

The area A1 on the distal end side of the slider-regulating portion 522A is referred to as a "third region R3." In the rod slider 52Ab shown in FIG. 22, the positioning portion 521 may be located in the third region R3. In the rod slider 52Ab shown in FIG. 22, the positioning portion 521 may be located in the third region R3, so the positioning portion 521 and the slider recess 522Aa do not fit together. Therefore, the rod slider 52Ab can move forward and backward within the range in which the positioning portion 521 is located in the third region R3.

Here, when the positioning portion 521 of the rod slider 52Ab is located in the first region R1, the distal end 3*a* of the rod 3 is located closer to the proximal side A2 than the distal end opening 22*a* of the first water supply conduit 22. That is, the distal end 3*a* of the rod 3 is located on the proximal side A2 rather than the first position P1.

Therefore, when the positioning portion 521 is located in the first region R1, the operator can move the rod slider 52Ab back and forth within a predetermined range in which the positioning portion 521 is located in the first region R1. At this time, the operator can peel off the burnt deposits of the tissues adhered inside the first water supply conduit 22 using the rod 3. The rod 3 may have a protrusion (burnt deposits-removing part) such as the spiral protrusion 31 shown in FIG. 19, and in that case, the operator can peel off and remove the burnt deposits of the tissues adhered inside of the first water supply conduit 22 using the burnt deposits-removing part.

In the rod slider 52Ab located in the first region R1, movement of the rod slider 52Ab toward the proximal end side A2 may be regulated by the contact between a proximal end 523 of the rod slider 52Ab and a proximal end 511 of the operation unit main body 51 in the longitudinal direction A.

Further, movement of the rod slider 52Ab toward the distal end side A1 may be regulated by the positioning portion 521 and the proximal end 522Ab of the slider-regulating portion 522A coming into contact with each other in the longitudinal direction A. Therefore, the range in which the rod slider 52Ab in which the positioning portion 521 is located in the first region R1 can move back and forth is limited to a predetermined range.

When the positioning portion 521 is located in the first region R1, the rod 3 has a range in which the distal end 3*a* can move forward and backward from the first position P1 located in the distal end opening 22*a* to the proximal end of the knife 2 (for example, the second position P2). Moreover, the range in which the rod slider 52Ab can move forward and backward may be regulated on the proximal end side A2 rather than the slider-regulating portion 522A. Further, the distal end of the rod 3 may be regulated within a range from the first position P1 to the proximal end of the knife 2 (second position P2), and it may be configured as: when the positioning portion 521 is fitted into the slider recess 522Aa, the distal end of the rod 3 is located at the first position P1. When the rod slider 52Ab is retreated to the maximum extent, the distal end of the rod 3 is located at the second position P2. The movement range of the distal end of the rod 3 does not necessarily have to be between the first position P1 and the second position P2, and may be regulated to any range within the first water supply conduit 22 of the knife 2.

When the positioning portion 521 of the rod slider 52Ab is located in the second region R2, the distal end 3*a* of the rod 3 is located at the first position PT. Therefore, since the distal end opening 22*a* of the knife 2 is covered and closed by the distal end 3*a* of the rod 3, it is possible to prevent tissue from entering the first water supply conduit 22 from the distal end opening 22*a* and clogging it.

When the positioning portion 521 is located in the second region R2, the positioning portion 521 and the slider recess 522Aa fit together, and the movement of the rod slider 52Ab in the longitudinal direction A is regulated by the proximal end 522Ab and the distal end 522Ac of the slider-regulating portion 522A. Therefore, the rod 3 may be maintained in a state in which the distal end 3*a* is positioned at the first position P1 (positioning state), that is, in a state where the position of the distal end 3*a* in the longitudinal direction A matches the position of the distal end of the knife 2.

The operator can release the fitting between the positioning portion 521 and the slider recess 522Aa by moving the rod slider 52Ab forward and backward with a predetermined force with respect to the slider 52. With the positioning portion 521 and the slider recess 522Aa disengaged, the operator can move the rod 3 forward and backward relative to the knife 2 by moving the rod slider 52Ab forward and backward relative to the slider 52. When the operator moves the rod slider 52Ab forward with respect to the slider 52, the fitting between the positioning portion 521 and the slider recess 522Aa is released, and the positioning portion 521 may move to the third region R3. When the distal end of the rod 3 is made to protrude from the distal end opening 22*a* of the first conduit 22, the positioning portion 521 and the slider recess 522Aa fit together, thereby generating a resistance force (user feedback) against the lever 55.

When the positioning portion 521 is located in the third region R3, the distal end 3*a* of the rod 3 is in a state (protruding state) in which it protrudes from the distal end opening 22*a* of the knife 2 toward the distal end side A1. When the rod 3 is in the protruding state, the distal end opening 22*a* of the knife 2 is not covered by the distal end 3*a* of the rod 3, so the operator can perform local injection treatment.

The slider-regulating portion 522A may be formed of an elastic member such as rubber. Therefore, when the positioning portion 521 is located in the first region R1, the operator can move the positioning portion 521 to the second region R2 by pushing the rod slider 52Ab toward the distal end side A1 with a predetermined force. Moreover, when the positioning portion 521 is located in the second region R2, the operator can move the positioning portion 521 to the third region R3 by pushing the rod slider 52Ab toward the distal end side A1 with a predetermined force.

The operator may move the rod slider 52Ab forward and backward with a predetermined amount of force, and advance and retreat the positioning portion 521 into the first region R1, the second region R2, and the third region R3, thereby adjusting the regulated state of the rod 3. The positioning state and the protruding state can be easily switched. Since the operator may require a certain amount of force to switch between the regulated state, the positioning state, and the protruding state, the operator can easily understand that the state (position) of the rod 3 is changing and can move the rod 3 to a desired position.

The above-mentioned slider-regulating portion 522A may be configured so that the operator can grasp the position of the rod 3 and does not need to have the slider recess 522Aa, for example. The above-mentioned slider-regulating portion 522A makes it possible to switch the regulating state, positioning state, and protruding state of the rod 3 by switching the position of the positioning portion 521 to the first region R1, the second region R2, and the third region R3. The slider-regulating portion may be configured so that the operator can grasp the switching between the regulating state and the protruding state of the rod 3.

Figure 23:
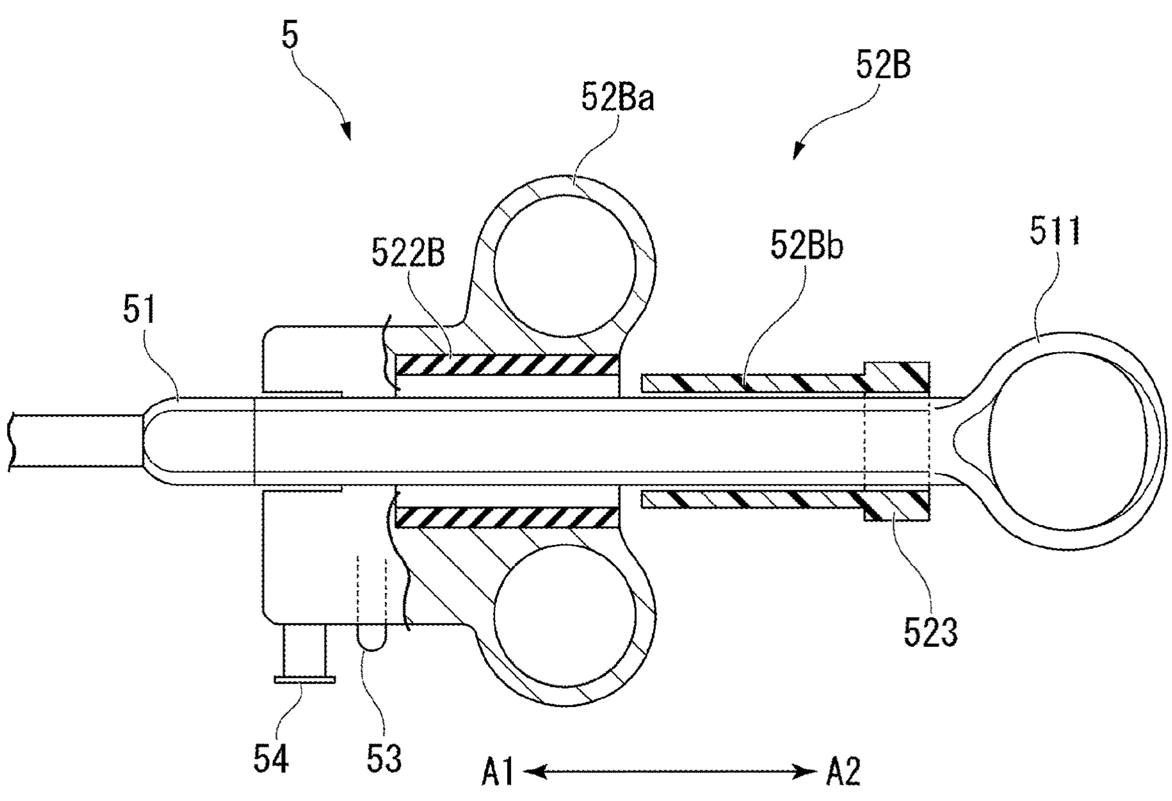
FIG. 23 is a cross-sectional view showing a modification of the operation unit.

FIG. 23 is a cross-sectional view showing a slider 52B in a modified example of the operation unit 5.

The slider 52B includes a knife slider 52Ba (first slider) and a rod slider 52Bb (second slider, slide lever). The knife slider 52Ba may be attached to the proximal end of the knife 2, and may be configured to move the knife 2 back and forth in the longitudinal direction A by moving forward and backward with respect to the operation unit main body 51. Further, the rod slider 52Bb may be attached to the proximal end of the rod 3, and may be configured to move the rod 3 back and forth in the longitudinal direction A by moving it forward and backward with respect to the operation unit main body 51.

As shown in FIG. 23, the knife slider 52Ba may include a cylindrical slider-regulating portion 522B (stopper) through which the operation unit main body 51 may be inserted. The shape, however, does not necessarily have to be strictly cylindrical. The slider-regulating portion 522B may extend toward the distal end side A1 compared to the above-described slider-regulating portion 522A, and does not have the slider recess 522Aa.

As shown in FIG. 23, the rod slider 52Bb may be a cylindrical member into which the operation unit main body 51 is inserted and does not have the positioning portion 521 compared to the rod slider 52Ab described above. Again, the shape does not necessarily have to be strictly cylindrical.

Here, the rod slider 52Bb and the slider-regulating portion 522B may be made of different materials. For example, the rod slider 52Bb may be made of resin (or any suitable or similar material), and the slider-regulating portion 522B may be made of rubber (or any suitable or similar material).

The inner diameter of the slider-regulating portion 522B and the outer diameter of the distal end of the rod slider 52Bb may be equal, or substantially equal to one another. Therefore, in a case where the distal end of the rod slider 52Bb is inserted into the slider-regulating portion 522B, when moving the rod slider 52Bb forward and backward relative to the slider-regulating portion 522B, the movement of the rod slider 52Bb is inhibited to some extent by the frictional force generated between the rod slider 52Bb and the slider-regulating portion 522B. In such an example, since a frictional force is generated between the rod slider 52Bb and the slider-regulating portion 522B, a predetermined amount of force may be added when the operator advances or retreats the rod slider 52Bb inserted into the slider-regulating portion 522B. The inner diameter of the slider-regulating portion 522B and the outer diameter of the distal end of the rod slider 52Bb do not need to be strictly equal.

Therefore, the operator can easily determine whether or not the rod slider 52Bb is inserted into the slider-regulating portion 522B. For example, when the rod slider 52Bb is located closer to the proximal end A2 than the slider-regulating portion 522B and the rod slider 52Bb is not inserted into the slider-regulating portion 522B, the distal end 3*a* of the rod 3 is located at the first position P1 or closer to the proximal end side A2 than the first position P1. That is, the rod 3 is in the above-mentioned regulated state.

When the distal end of the rod slider 52Bb is inserted into the slider-regulating portion 522B, the distal end 3*a* of the rod 3 is located on the distal end side A1 from the first position P1 and protrudes from the distal end opening 22*a* of the knife 2 toward the distal end side A1. By giving the operator a sense of resistance due to the friction between the rod slider 52Bb and the slider-regulating portion 522B, the operator can easily grasp the position of the distal end 3*a* of the rod 3.

On the other hand, when the rod slider 52Bb and the end of the slider-regulating portion 522B come into contact, the distal end of the rod 3 is at the first position P1, that is, the position of the distal end 3*a* in the longitudinal direction A matches the position of the distal end of the knife 2. Further, the proximal end side A2 of the slider-regulating portion 522B can be substantially regulated as a range in which the rod slider 52Bb can move forward and backward. When the distal end of the rod 3 is made to protrude from the distal end opening 22*a* of the first conduit 22, the lever 55 abuts against the end of the slider-regulating portion 522B, thereby generating a resistance force (user feedback) against the rod slider 52Bb. Further, the distal end of the rod 3 can be regulated in the range from the first position P1 to the proximal end of the knife 2 (second position P2), and it may be configured so that when the rod slider 52Bb is brought into contact with the end of the slider-regulating portion 522B, the distal end of the rod 3 is located at the first position PT; and when the rod slider 52Bb is retreated to the maximum extent, the distal end of the rod 3 is located at the second position P2. The movement range of the distal end of the rod 3 does not necessarily have to be between the first position P1 and the second position P2 and may be regulated to any range within the first water supply conduit 22 of the knife 2.

Figure 24:
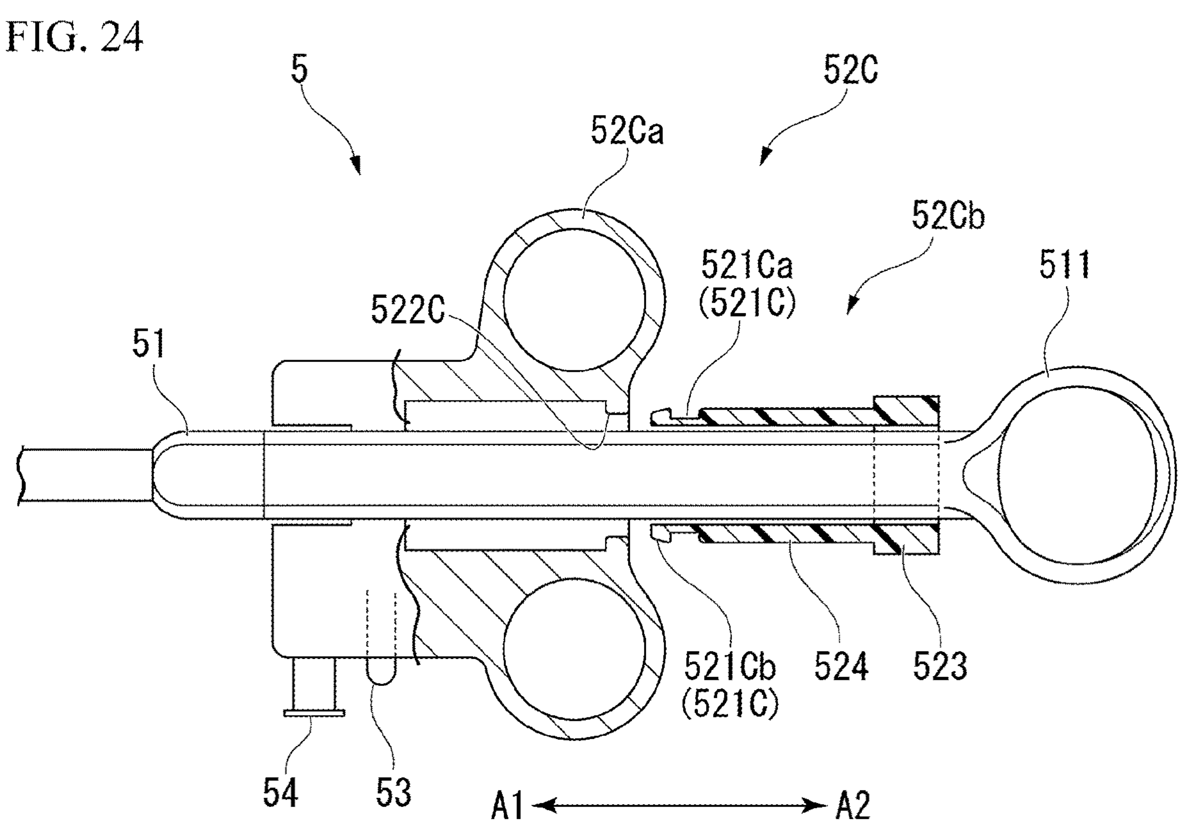
FIG. 24 is a cross-sectional view showing a modification of the operation unit.

FIG. 24 is a cross-sectional view showing a slider 52C in a modified example of the operation unit 5, in which the slider 52C includes a knife slider 52Ca (first slider) and a rod slider 52Cb (second slider, slide lever).

The knife slider 52Ca may be attached to the proximal end of the knife 2, and may be configured to move the knife 2 forward and backward in the longitudinal direction A by moving forward and backward with respect to the operation unit main body 51. Further, the rod slider 52Cb may be attached to the proximal end of the rod 3, and may be configured to move the rod 3 back and forth in the longitudinal direction A by moving it forward and backward with respect to the operation unit main body 51.

The knife slider 52Ca may be a cylindrical member into which the operation unit main body 51 is inserted. The shape does not necessarily have to be strictly cylindrical and may be any suitable or appropriate shape. At the proximal end of the knife slider 52Ca, a slider-regulating portion 522C (stopper) that may be convex toward the operation unit main body 51 may be provided on the inner peripheral surface surrounding the operation unit main body 51. The slider-regulating portion 522C may be provided all or entirely (or substantially so) around the inner peripheral surface of the knife slider 52Ca, or may be provided only on a part of the inner peripheral surface.

The rod slider 52Cb may a cylindrical member into which the operation unit main body 51 may be inserted. The shape does not necessarily have to be strictly cylindrical and can be any suitable or appropriate shape. The rod slider 52Cb may include a second slider main body 524 and a positioning portion 521C provided at the distal end of the second slider main body 524.

The positioning portion 521C may include a small diameter portion 521Ca having a smaller outer diameter than the second slider main body 524, and a large diameter portion 521Cb provided on the distal end side A1 of the small diameter portion 521Ca and having a larger outer diameter than the small diameter portion 521Ca. That is, in the outer peripheral surface of the rod slider 52Cb, the portion where the small diameter portion 521Ca is provided is more concave than the portion where the second slider main body 524 and the large diameter portion 521Cb are provided. The small diameter portion 521Ca may be or may include, for example, a portion of the outer peripheral surface of the rod slider 52Cb that may be concave all around.

The outer diameter of the second slider main body 524 and the large diameter portion 521Cb may be slightly larger than the inner diameter of the slider-regulating portion 522C in the knife slider 52Ca. Further, the outer diameter of the small diameter portion 521Ca may be slightly smaller than the inner diameter of the slider-regulating portion 522C.

Here, when the rod slider 52Cb is located in a region (first region) on the proximal side A2 than the slider-regulating portion 522C, the operator can insert the rod slider 52Cb through the slider-regulating portion 522C by pushing the rod slider 52Cb toward the distal end side A1 with a predetermined force.

In such an example, one or more of the large diameter part 521Cb or the slider-regulating portion 522C elastically deforms, so that the large diameter part 521Cb climbs over the slider-regulating portion 522C, and the convex slider-regulating portion 522C and the concave small diameter part 521Ca are mated.

In the state where the slider-regulating portion 522C and the small diameter portion 521Ca are fitted, the small diameter portion 521Ca may be arranged at a position overlapping the slider-regulating portion 522C in the direction orthogonal to the longitudinal direction A. Further, since the outer diameter of the second slider main body 524 is larger than the inner diameter of the slider-regulating portion 522C, the slider-regulating portion 522C may be sandwiched or otherwise located between the large diameter part 521Cb and the second slider main body 524 in the longitudinal direction A. That is, in a state where the slider-regulating portion 522C and the small diameter portion 521Ca are fitted, the positioning portion 521C is located in the second region.

When the positioning portion 521C is located in the second region, by pushing the rod slider 52Cb toward the distal end side A1 with a predetermined force, the operator can elastically deform the slider-regulating portion 522C and move the positioning portion 521C to a region (third region) on the distal side A1 of the slider-regulating portion 522C. At this time, the slider-regulating portion 522C and the second slider main body 524 maintain a state in which they are in contact with each other.

When the positioning portion 521C of the rod slider 52Cb is located in the first region, the distal end 3*a* of the rod 3 is located on the proximal side A2 of the distal end opening 22*a* of the first water supply conduit 22. That is, the distal end 3*a* of the rod 3 is located on the proximal side A2 rather than the first position P1.

When the positioning portion 521C is located in the first region, the operator can move the rod slider 52Cb forward and backward within a predetermined range in which the positioning portion 521C is located in the first region. At this time, the operator can peel off the burnt deposits of the tissues adhered inside the first water supply conduit 22 by using the rod 3. The rod 3 may have a protrusion (burnt deposits-removing part) such as the spiral protrusion 31 shown in FIG. 19, and the operator can peel off the burnt deposits of the tissues adhered inside the first water supply conduit 22 using the burnt deposits-removing part.

In an example, when the rod slider 52Cb located in the first region, movement of the rod slider 52Cb toward the proximal end side A2 is regulated by the contact between the proximal end 523 of the rod slider 52Cb and the proximal end 511 of the operation unit main body 51 in the longitudinal direction A.

Furthermore, the movement of the rod slider 52Cb toward the distal end side A1 is regulated by contact between the large diameter portion 521Cb of the positioning portion 521C and the slider-regulating portion 522C in the longitudinal direction A. Therefore, the range in which the rod slider 52Cb located in the first region can move back and forth is limited to a predetermined range.

When the positioning portion 521C is located in the first region, the distal end 3*a* of the rod 3 is in a state (regulated state) regulated within a range from a first position P1 located at the distal end opening 22*a* to the proximal end of the knife 2 (for example, a second position P2). Further, the proximal end side A2 of the slider-regulating portion 522C may be regulated as a range in which the rod slider 52Cb can move forward and backward. Further, the distal end of the rod 3 may be regulated in the range from the first position P1 to the proximal end of the knife 2 (second position P2), and it may be configured so that when the positioning portion 521C is fitted into the slider-regulating portion 522C, the distal end of the rod 3 is located at the first position P1. When the rod slider 52Cb is retreated to the maximum extent, the distal end of the rod 3 is located at the second position P2. The movement range of the distal end of the rod 3 does not necessarily have to be between the first position P1 and the second position P2, and may be regulated to any range within the first water supply conduit 22 of the knife 2.

When the positioning portion 521C of the rod slider 52Cb is located in the second region, the distal end 3*a* of the rod 3 is located at the first position P1. Therefore, since the distal end opening 22*a* of the knife 2 is covered and closed by the distal end 3*a* of the rod 3, it is possible to prevent tissue from entering the first water supply conduit 22 from the distal end opening 22*a* and clogging it.

When the positioning portion 521C is located in the second region, the positioning portion 521C and the slider-regulating portion 522C fit together, and the movement of the rod slider 52Cb in the longitudinal direction A is regulated by the slider-regulating portion 522C. Therefore, the rod 3 may be maintained in a state in which the distal end 3*a* is positioned at the first position P1 (positioning state), that is, in a state where the position of the distal end 3*a* in the longitudinal direction A matches the position of the distal end of the knife 2.

The operator can release the fitting between the positioning portion 521C and the slider-regulating portion 522C by moving the rod slider 52Cb forward and backward with respect to the slider 52 with a predetermined force. With the positioning portion 521C and the slider-regulating portion 522C disengaged, the operator can move the rod 3 forward and backward relative to the knife 2 by moving the rod slider 52Cb forward and backward relative to the slider 52. When the operator moves the rod slider 52Cb forward with respect to the slider 52, the fitting between the positioning portion 521C and the slider-regulating portion 522C is released, and the positioning portion 521C moves to the third region. When the distal end of the rod 3 is made to protrude from the distal end opening 22*a* of the first conduit 22, the positioning portion 521C and the slider-regulating portion 522C fit together, thereby generating a resistance force (user feedback) against the lever 55.

When the positioning portion 521C is located in the third region, the distal end 3*a* of the rod 3 is in a state (protruding state) in which it protrudes from the distal end opening 22*a* of the knife 2 toward the distal end side A1. When the rod 3 is in the protruding state, the distal end opening 22*a* of the knife 2 is not covered by the distal end 3*a* of the rod 3, so the operator can perform local injection treatment.

Here, when the positioning portion 521C is located in the third region, the rod slider 52Cb and the slider-regulating portion 522C do not need to be in contact with each other. For example, in the second slider main body 524, by making the outer diameter of the portion closer to the proximal end A2 than the small diameter portion 521Ca smaller than the inner diameter of the slider-regulating portion 522C, the rod slider 52Cb located in the third region can be moved back and forth without bringing the second slider main body 524 into contact with the slider-regulating portion 522C.

In such an example, at the proximal end of the small diameter portion 521Ca, a convex shape may be used or provided (second large diameter portion) that regulates movement of the rod slider 52Cb toward the distal end side A1 in the second region.

In the above embodiment, a structure may be adopted in which the operation unit 5 includes the tubular member 43 and the lever 55 can be positioned with respect to the tubular member 43 connected to the proximal end of the operating wire 4. The proximal end of the tubular member 43 may be connected to the slider 52.

Figure 25:
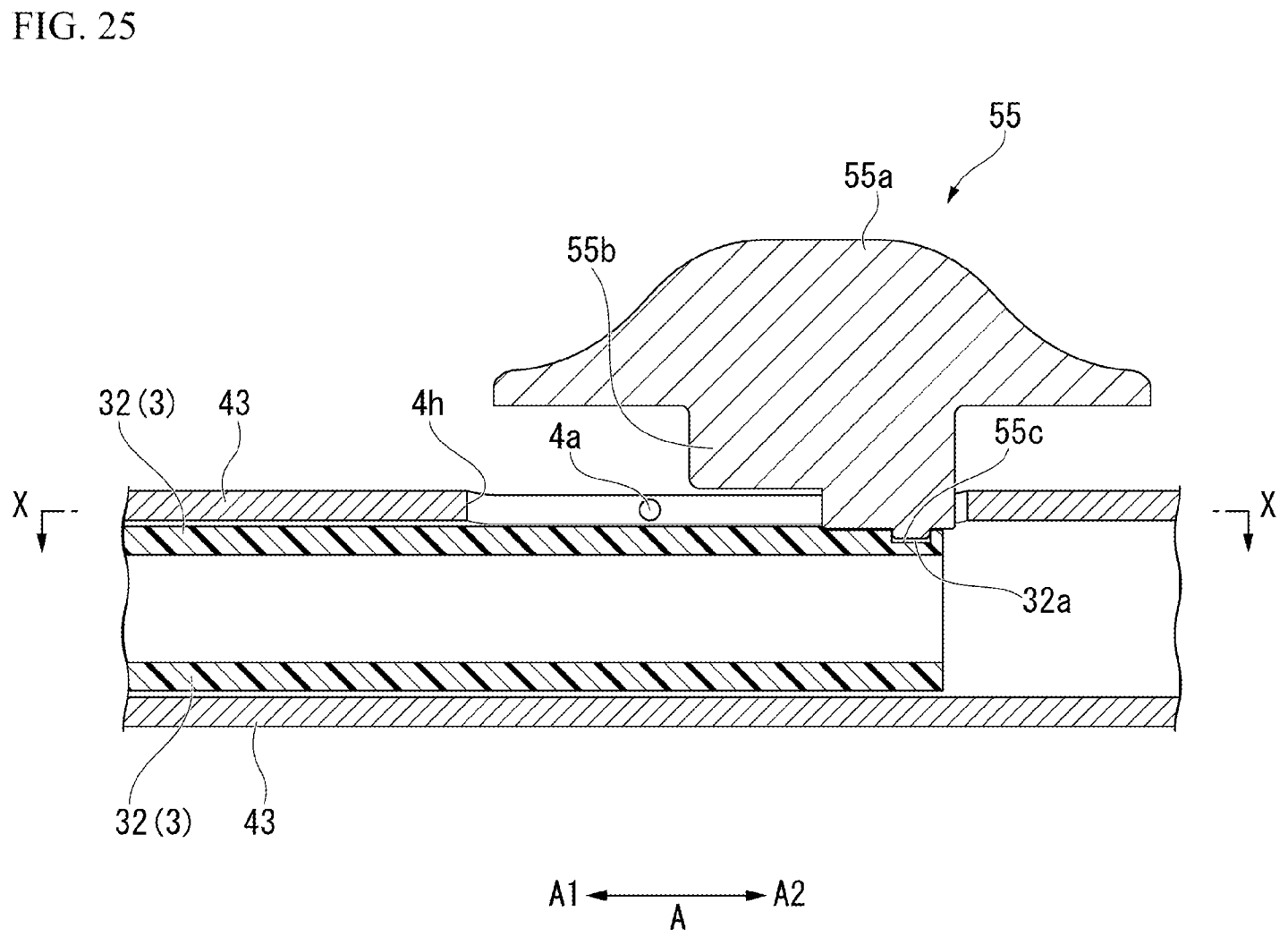

FIG. 25 is a diagram showing the connection between the lever 55 and the rod 3 in the operation unit 5. In FIG. 25, some parts such as the sheath 1 are omitted.

The proximal end 32 of the rod 3 may include a cylindrical shape, for example, as shown in FIG. 25. The shape does not necessarily have to be strictly cylindrical and may be any suitable or appropriate shape. The lever 55 may be attached to an engagement recess 32*a* in the proximal end 32 of the rod 3.

The lever 55 may include a convex handle portion 55*a* that is operated by the operator, and an engaging portion 55*b* that is connected to the rod 3. As shown in FIG. 25, an engaging convex portion 55*c* is provided at the distal end of the engaging portion 55*b*. The engaging convex portion 55*c* of the lever 55 and the engagement recess 32*a* of the rod 3 may engage, and the lever 55 and the rod 3 may connect.

Furthermore, as shown in FIG. 25, a through-hole 4*h* that penetrates in the radial direction and extends in the longitudinal direction A may be formed at the proximal end of the tubular member 43. The engaging portion 55*b* of the lever 55 may be provided in the through-hole 4*h* of the tubular member 43, and may be provided so as to be movable in the longitudinal direction A within the range in which the through-hole 4*h* is formed. When the operator moves the lever 55 forward or backward in the longitudinal direction A with respect to the slider 52, the rod 3 connected to the lever 55 can move forward or backward, but the operating wire 4 does not move forward or backward. That is, when the lever 55 is moved forward or backward with respect to the slider 52, the rod 3 is moved forward or backward relative to the knife 2.

Figure 26:
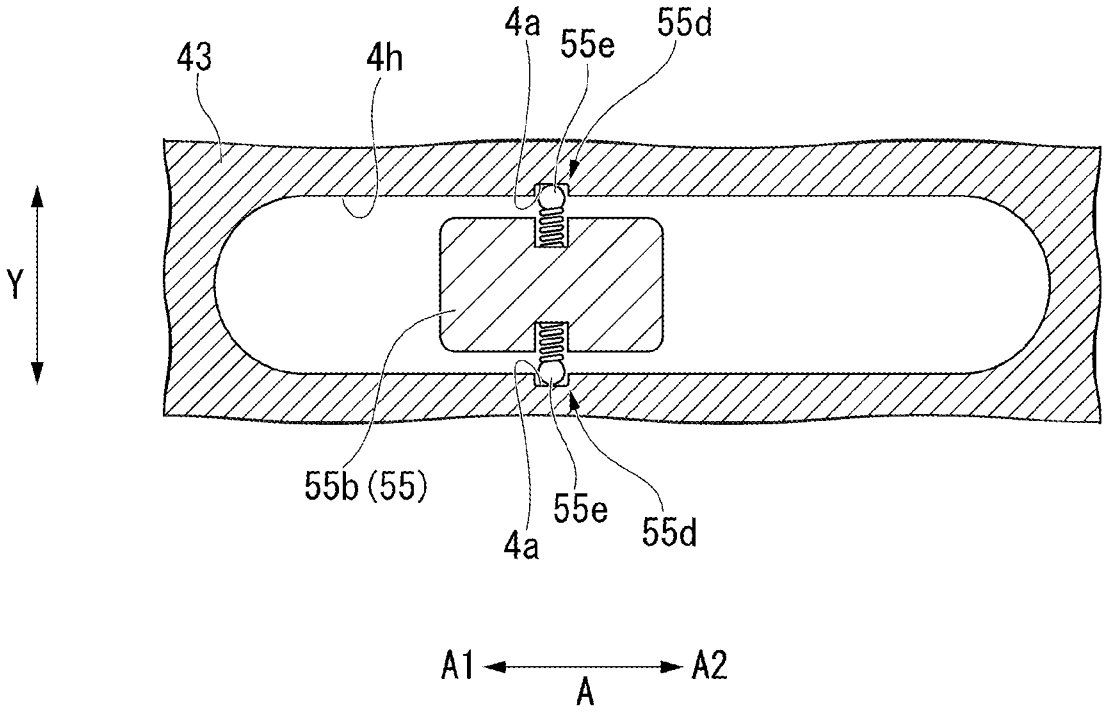
FIG. 26 is a sectional view of the lever and the tubular member taken along the line X-X shown in FIG. 25.

FIG. 26 is a cross-sectional view of the lever 55 and the tubular member 43 taken along the line X-X shown in FIG. 25. As shown in FIGS. 25 and 26, an engagement recess 4*a* (lever positioning portion) recessed in the width direction Y may be formed on the inner peripheral surface of the through-hole 4*h* of the tubular member 43.

Further, the engaging convex portion 55*c* of the lever 55 may be provided with a ball click 55*d* composed of a spring member and a spherical member (spherical member). As shown in FIG. 26, the ball click 55*d* may be provided on both sides in the width direction Y of the engaging portion 55*b* surrounded by the through-hole 4*h* of the tubular member 43.

The ball click 55*d* includes a spring member connected to the engaging portion 55*b* and a spherical member 55*e* connected to the distal end of the spring member. The ball click 55*d* can be expanded and contracted in the width direction Y by the elasticity of the spring member.

When the lever 55 is moved back and forth in the longitudinal direction A, the lever 55 moves back and forth with the spherical member 55*e* provided at the distal end of the ball click 55*d* in contact with the inner peripheral surface of the through-hole 4*h*. When the lever 55 is arranged at a position where the engagement recess 4*a* and the ball click 55*d* overlap in the width direction Y, the spring member of the ball click 55*d* extends in the width direction Y, and the distal end (spherical member 55*e*) of the ball click 55*d* engages with the engagement recess 4*a*.

When the ball click 55*d* and the engagement recess 4*a* are engaged, the distal end 3*a* of the rod 3 is located at the first position P1, that is, the position of the distal end 3*a* in the longitudinal direction A coincides with the position of the distal end of the knife 2. Furthermore, the range in which the lever 55 can move forward and backward may be regulated on the proximal end side A2 of the engagement recess 4*a*. The distal end of the rod 3 may be regulated to a range from the first position P1 to the proximal end of the knife 2 (second position P2), and it may be configured so that when the ball click 55*d* is engaged with the engagement recess 4*a*, the distal end of the rod 3 is located at the first position P1, and when the lever 55 is moved back to the maximum extent, the distal end of the rod 3 is located at the second position P2. The movement range of the distal end of the rod 3 does not necessarily have to be between the first position P1 and the second position P2 and may be regulated to any range within the first water supply conduit 22 of the knife 2.

In addition, when the operator moves the slider 52 forward and backward in a state where the ball click 55*d* and the engagement recess 4*a* are connected to each other, so that the knife 2 connected to the operating wire 4 and the rod 3 connected to the lever 55 can be moved forward and backward while maintaining the state in which the distal end 3*a* of the rod 3 is positioned at the first position P1 (positioning state).

The operator can disengage the ball click 55*d* from the engagement recess 4*a* by moving the lever 55 forward and backward relative to the slider 52 with a predetermined amount of force. With the ball click 55*d* disengaged from the engagement recess 4*a*, the operator can move the rod 3 forward and backward relative to the knife 2 by moving the lever 55 forward and backward relative to the slider 52. When the distal end of the rod 3 protrudes from the distal end opening 22*a* of the first conduit 22, the ball click 55*d* can engage with the engagement recess 4*a*, thereby generating a resistance force (user feedback) against the lever 55.

In the above embodiment, a structure may be adopted in which the operation unit 5 includes the tubular member 43 and the lever 55 can be positioned with respect to the tubular member 43 connected to the proximal end of the operating wire 4. The proximal end of the tubular member 43 may be connected to the slider 52.

Figure 27:
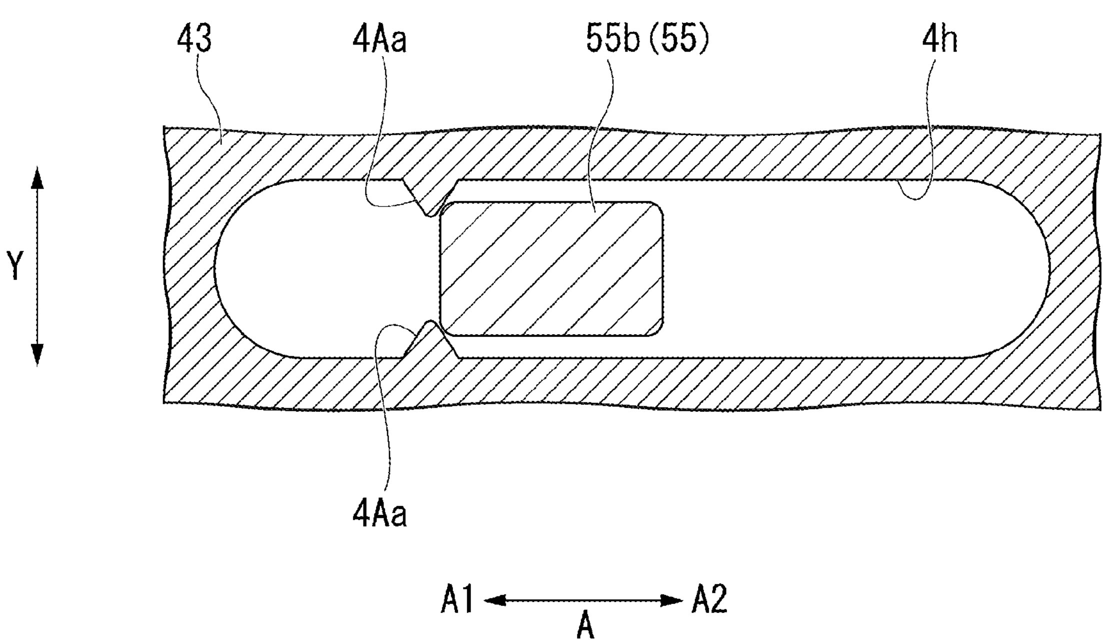
FIG. 27 is a sectional view showing a modification of the lever and the tubular member.

FIG. 27 is a cross-sectional view showing a modified example of the lever 55 and the tubular member 43. The cross section shown in FIG. 27 is a cross-sectional view of the lever 55 and the tubular member 43 taken along the line X-X shown in FIG. 25, similar to FIG. 26.

As shown in FIG. 27, the through-hole 4*h* of the tubular member 43 may be provided with a regulating convex portion (lever positioning portion) 4Aa that is convex in the width direction Y from the inner peripheral surface of the through-hole 4*h*. When the distal end of the lever 55 and the regulating convex portion 4Aa are brought into contact, the distal end of the rod 3 is at the first position P1, that is, the position of the distal end 3*a* in the longitudinal direction A coincides with the position of the distal end of the knife 2. Further, the proximal end side A2 of the regulating convex portion 4Aa can be regulated as a range in which the lever 55 can move forward and backward. Further, the distal end of the rod 3 is regulated in the range from the first position P1 to the proximal end of the knife 2 (second position P2), and it may be configured so that when the lever 55 is brought into contact with the regulating convex portion 4Aa, the distal end of the rod 3 is located at the first position P1, and when the lever 55 is moved back to the maximum extent, the distal end of the rod 3 is located at the second position P2. The movement range of the distal end of the rod 3 does not necessarily have to be between the first position P1 and the second position P2 and may be regulated to any range within the first water supply conduit 22 of the knife 2.

By moving the lever 55 toward the distal end side A1 with a predetermined amount of force, the lever 55 can overcome the regulation protrusion 4Aa and move further than the regulation protrusion 4Aa toward the distal end side A1. When the distal end of the rod 3 is made to protrude from the distal end opening 22*a* of the first conduit 22, the lever 55 abuts against the regulating convex portion 4Aa, thereby generating a resistance force (user feedback) against the lever 55.

In the above embodiment, the tubular member 43 may include a regulating member 4*b* that regulates the movement of the lever 55 to some extent.

Figure 28:
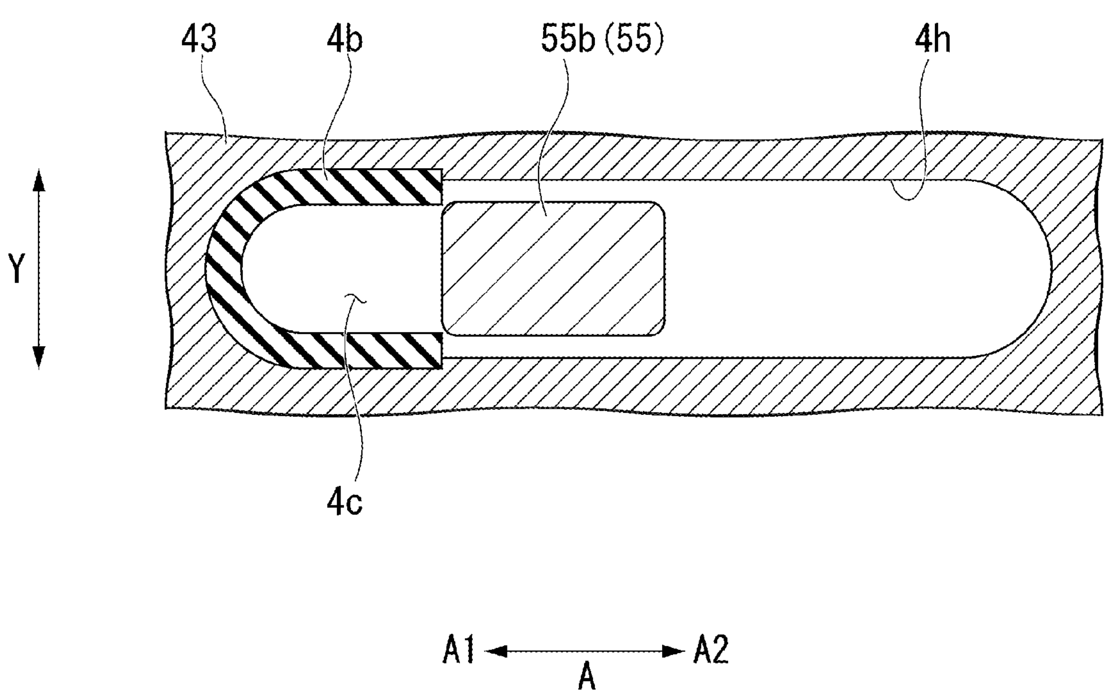
FIG. 28 is a sectional view showing a modification of the lever and tubular member.

FIG. 28 is a cross-sectional view showing a modified example of the lever 55 and the tubular member 43. The cross section shown in FIG. 28 is a cross-sectional view of the lever 55 and the tubular member 43 taken along the line X-X shown in FIG. 25, similar to FIGS. 26 and 27.

As shown in FIG. 28, at the distal end of the through-hole 4*h* of the tubular member 43, the regulating member 4*b* may be provided along the inner peripheral surface of the through-hole 4*h*. In the opening of the through-hole 4*h*, the region (regulating region 4*c*) in which the regulating member 4*b* is provided may have a smaller dimension in the width direction Y than other regions.

When the lever 55 is moved toward the distal end side A1 and at least a portion of the lever 55 is located in the regulating area 4*c*, the engaging portion 55*b* of the lever 55 and the regulating member 4*b* come into contact in the width direction Y The regulating member 4*b* may be made of, for example, a rubber material.

Therefore, when the operator moves the lever 55 toward the distal end side A1 and the lever 55 and the regulating member 4*b* come into contact, the operator feels a sense of resistance due to the friction between the engaging portion 55*b* of the lever 55 and the regulating member 4*b*.

When at least a portion of the engaging portion 55*b* of the lever 55 is located in the regulating region 4*c*, the distal end 3*a* of the rod 3 is in a state (protruding state) in which it can protrude from the distal end opening 22*a* of the knife 2 toward the distal end side A1. Therefore, the operator can easily understand that the rod 3 is in the protruding state by the sense of resistance felt from the lever 55 located in the regulating area 4*c*.

On the other hand, when the engaging portion 55*b* of the lever 55 and the end of the regulating member 4*b* come into contact, the distal end of the rod 3 is at the first position P1, that is, the position of the distal end 3*a* in the longitudinal direction A coincides with the position of the distal end of the knife 2. Further, the proximal end side A2 of the regulating member 4*b* is substantially regulated as a range in which the lever 55 can move forward and backward. When the distal end of the rod 3 is made to protrude from the distal end opening 22*a* of the first conduit 22, the lever 55 abuts against the end of the regulating member 4*b*, thereby generating a resistance force (user feedback) against the lever 55. Further, the distal end of the rod 3 can be regulated within a range from the first position P1 to the proximal end of the knife 2 (second position P2), and it may be configured so that when the lever 55 is brought into contact with the end of the regulating member 4*b*, the distal end of the rod 3 is located at a first position P1, and when the lever 55 is moved back to the maximum extent, the distal end of the rod 3 is located at a second position P2. The movement range of the distal end of the rod 3 does not necessarily have to be between the first position P1 and the second position P2, and may be regulated to any range within the first water supply conduit 22 of the knife 2.

While an example embodiment of the present disclosure has been described in detail above with reference to the drawings, the specific configurations are not limited to the embodiment and may include design changes or the like within a range not departing from the scope of the present disclosure. Also, the components illustrated in the above-described embodiment and modified examples can be configured by appropriately combining them.

Second Embodiment

A treatment tool 100D according to a second embodiment of the present disclosure will be described with reference to FIGS. 29 to 30. In the following description, components that are common to those already described will be denoted by the same reference signs and duplicate description will be omitted.

Figure 29:
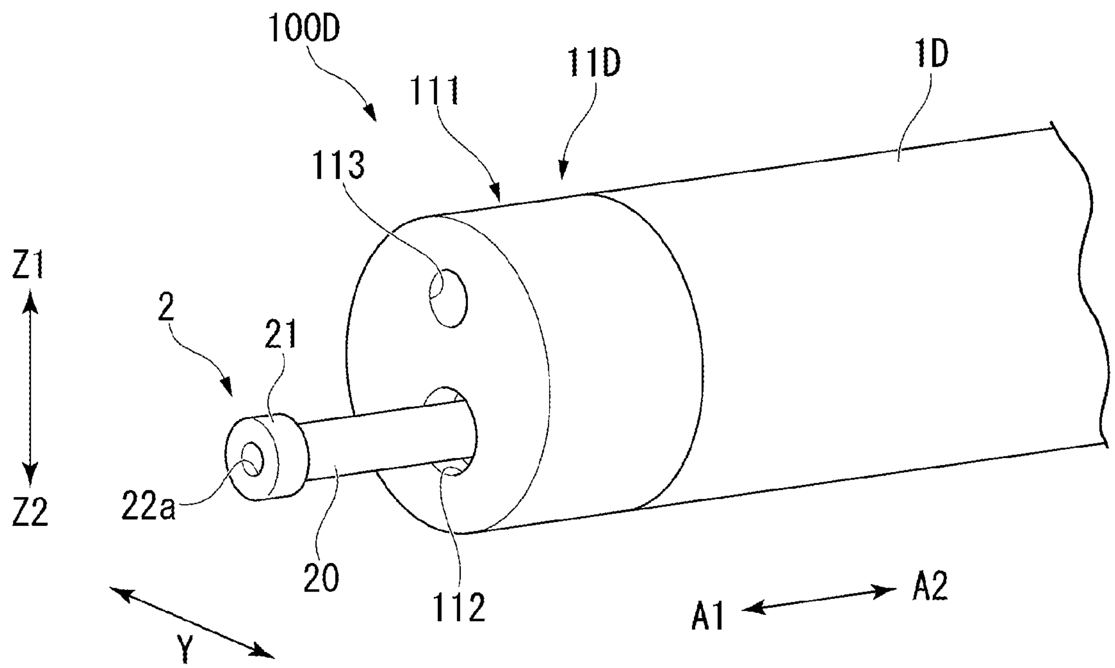
FIG. 29 is a perspective view of a distal end part of a treatment tool according to a second embodiment.

FIG. 29 is a perspective view of a distal end part of the treatment tool 100D according to the second embodiment. FIG. 30 is a cross-sectional view of the distal end part of the treatment tool 100D.

In an example of the second embodiment, the treatment tool 100D does not include the rod 3. As illustrated in FIGS. 29 and 30, the treatment tool 100D includes a sheath 1D, a knife 2, a connecting insert 23, a water supply tube 24, an operation wire 4, and may include an operation unit.

The sheath 1D may include the same configuration as the sheath 1 of the first embodiment except that an insulation tip (distal end member) 11D provided at a distal end 1*a* of the sheath 1D is different.

The insulation tip 11D may include two different through-holes. The insulation tip 11D includes an insulation tip main body (distal end member main body) 111, a first through-hole 121, and a second through-hole 122.

The insulation tip main body 111 may be a main body portion of the insulation tip 11D. The insulation tip main body 111 may include a first opening 112 at a distal end surface 111*a* on a distal end side A1, and a second opening 113 provided at a position different from the first opening 112 and through which a fluid passing through a third water supply conduit (water supply conduit) 24*h* of a water supply tube 24 to be described later flows out.

The first through-hole 121 may be a hole that penetrates the insulation tip main body 111 in a longitudinal direction A. A central axis OB2 of the first through-hole 121 in the longitudinal direction A may be disposed at a position different from a central axis O1 in the longitudinal direction A of the sheath 1D in a height direction Z intersecting the longitudinal direction A and a width direction Y The first through-hole 121 may include a first distal end conduit 121*h* inside. The first distal end conduit 121*h* may communicate or engage with the first opening 112 formed in the distal end surface 111*a*. In other words, the first distal end conduit 121*h* may include the first opening 112 on the distal end side A1. The first opening 112 may be slightly smaller than a flange 21 which may be a distal end part of the knife 2, and may be formed in a size that allows the flange 21 to lock therein. Therefore, the flange 21 may be locked at the first opening 112 and may not move (or be movable) from the first opening 112 to a proximal end side A2.

The second through-hole 122 may penetrate in the longitudinal direction A and may be provided apart from the first through-hole 121 when viewed from the distal end side A1 in the longitudinal direction A. A central axis OB3 of the second through-hole 122 in the longitudinal direction A may be disposed at a different position in the height direction Z from the central axis O1 of the sheath 1D in the longitudinal direction A and the central axis OB2 (off-set position). The second through-hole 122 may include a second distal end conduit 122*h* inside. The second distal end conduit 122*h* may communicate or engage with the second opening 113 formed on the distal end surface 111*a*. In other words, the second distal end conduit 122*h* may include the second opening 113 on the distal end side A1.

Figure 30:
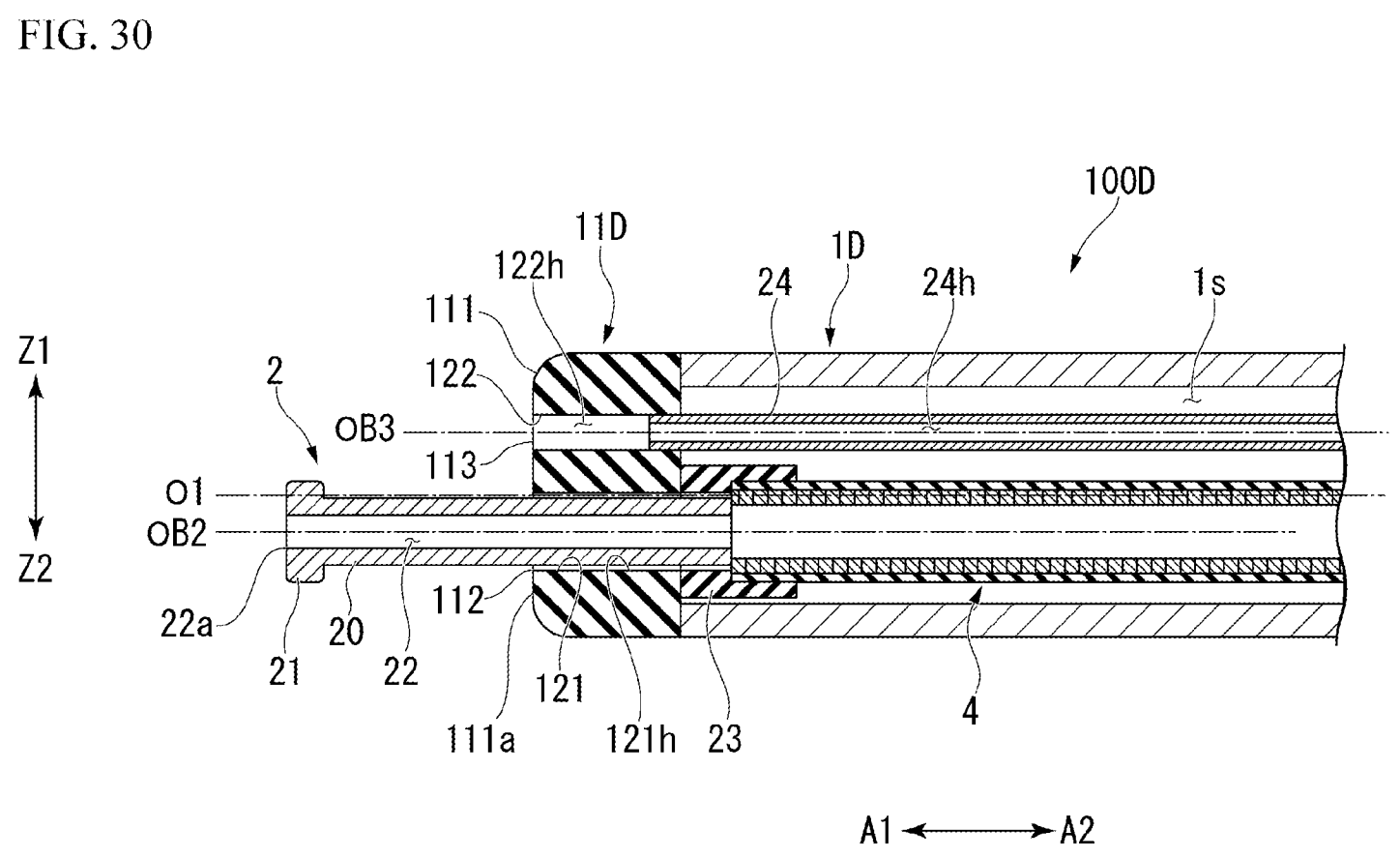

As illustrated in FIG. 30, a direction in which the central axis OB2 is disposed with respect to the central axis O1 is referred to as a lower side Z2 in the height direction Z, and a direction in which the central axis OB3 is disposed with respect to the central axis O1 is referred to as an upper side Z1 in the height direction Z. In the present embodiment, the central axis OB2 may be formed on the lower side Z2 with respect to the central axis OB3. However, the central axis OB2 may be formed on the upper side Z1 with respect to the central axis OB3. Also, the central axis OB2 or the central axis OB3 may be formed on the same axis as the central axis O1.

The knife 2 may be inserted into the sheath 1D. The knife 2 may be provided to be able to protrude to the distal end side A1 from the first opening 112 of the first distal end conduit 121*h* of the insulation tip 11D. A central axis of the knife 2 in the longitudinal direction A can substantially coincide with the central axis OB2 of the first through-hole 121 of the sheath 1D in the longitudinal direction A.

The water supply tube 24 may be a tubular member extending in the longitudinal direction A. The third water supply conduit 24*h* (water supply conduit) for water supply is formed inside the water supply tube 24. The third water supply conduit 24*h* may communicate or engage with the second distal end conduit 122*h* of the second through-hole 122. Therefore, a fluid flowing through the third water supply conduit 24*h* of the water supply tube 24 can pass through the second distal end conduit 122*h* and flow out from the second opening 113. Further, the water supply tube 24 may not an essential component, and thus may be optional or may be omitted. In such an example, an internal space is of the sheath 1D can serve as a water supply conduit of the fluid.

In the present embodiment, compared to the operation unit 5 of the first embodiment, an operation unit does not include the lever 55 and may include two liquid supply ports. One of the two liquid supply ports may be connected to a proximal end of the water supply tube 24. A fluid supplied to the third water supply conduit 24*h* of the water supply tube 24 may be discharged from the second opening 113. The second of the two liquid supply ports may be connected to a proximal end of a second water supply conduit 42 of the operation wire 4 as in the first embodiment, and the supplied fluid may be discharged from a distal end opening 22*a* of a first water supply conduit 22 of the knife 2. A liquid supply device such as a pump may be connected to each of the two liquid supply ports. However, the pump may be controlled to supply a liquid to either of the two liquid supply ports by providing a switching valve or the like. Also, the pump may supply not only a liquid but also a gas.

The opening area of the second opening 113 may be smaller than the opening area of the first opening 112. In such an example, the opening area refers to the area of the opening in a plane view from the longitudinal direction A. By making the opening area of the second opening 113 smaller than the opening area of the first opening 112, it can be possible to maintain both the cutting performance of the knife 2 and the smooth water supply from the second opening 113.

The opening area of the second opening 113 may be larger than the opening area of the tip opening 22*a* of the first water supply conduit 22 and the knife 2 may be rotatable around the longitudinal direction A about the central axis OB2 with respect to the sheath 1D and the insulating tip 11D.

In the present embodiment, the insulation tip 11D of the sheath 1D may include the first opening 112 on the distal end surface 111*a* of the insulation tip main body 111, and the second opening 113 provided at a different position from the first opening 112 and through which the fluid passing through the third water supply conduit 24*h* of the water supply tube 24 flows out. Therefore, even when burnt deposits of tissues become fixed to the distal end of the knife 2 due to incision, cauterization, or peeling treatments clog the distal end opening 22*a*, and the fluid passing through the first water supply conduit 22 is not able to be supplied, the operator can perform water supply by causing the fluid flowing through the third water supply conduit 24*h* of the water supply tube 24 to flow out from the second opening 113 in which tissues are not adhered and water supplying is not hindered.

Additionally, by making the knife 2 rotatable around the longitudinal direction A with respect to the sheath 1D and the insulating tip 11D, the fluid discharged from the second opening 113 can evenly wash away the burnt deposits of tissues adhered to the flange 21 of the knife 2.

Figure 31:
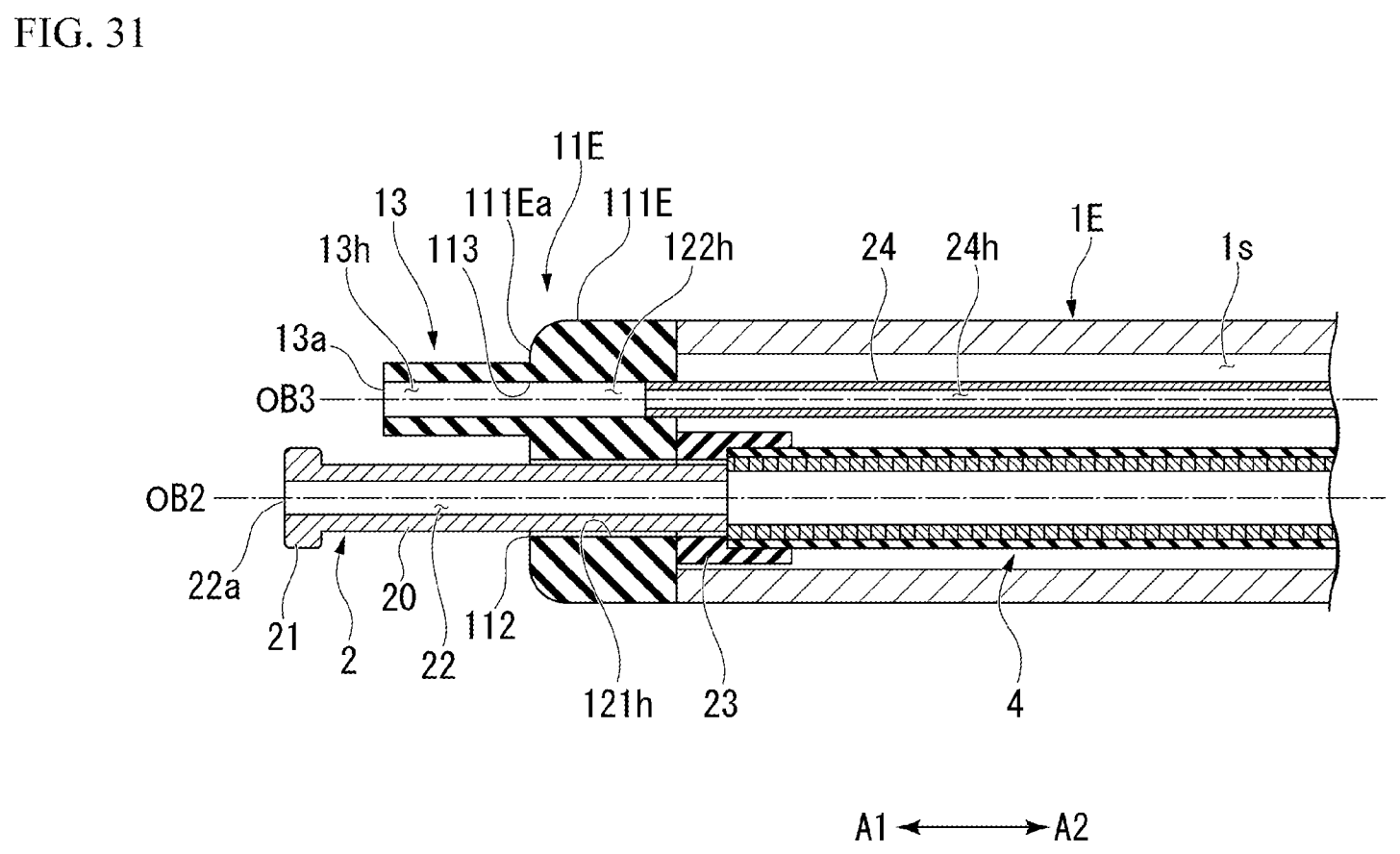

According to the present embodiment, the sheath 1D includes the insulation tip 11D at the distal end, but an aspect of the insulation tip 11D is not limited thereto. FIG. 31 is a cross-sectional view of an insulation tip 11E of a sheath 1E which is a modified example of the insulation tip 11D of the sheath 1D. An insulation tip main body 111E of the insulation tip 11E may include a protruding part 13 that protrudes to the distal end side A1 from a distal end surface 111Ea. The protruding part 13 may be formed in a cylindrical shape extending in the longitudinal direction A with the central axis OB3 as a central axis. The protruding part 13 may include a protruding part conduit 13*h* inside. Also, a proximal end of the protruding part 13 may be attached to the distal end surface 111Ea to cover the second opening 113, and the protruding part conduit 13*h* therein may communicate or engage with the second distal end conduit 122*h*. The protruding part 13 may include a protruding part opening 13*a* at a distal end thereof. A fluid passing through the third water supply conduit 24*h* of the water supply tube 24 can pass through the second distal end conduit 122*h*, flows out from the second opening 113, and then passes through the protruding part conduit 13*h* communicating with the second distal end conduit 122*h* to flow out from the protruding part opening 13*a*.

Figure 32:
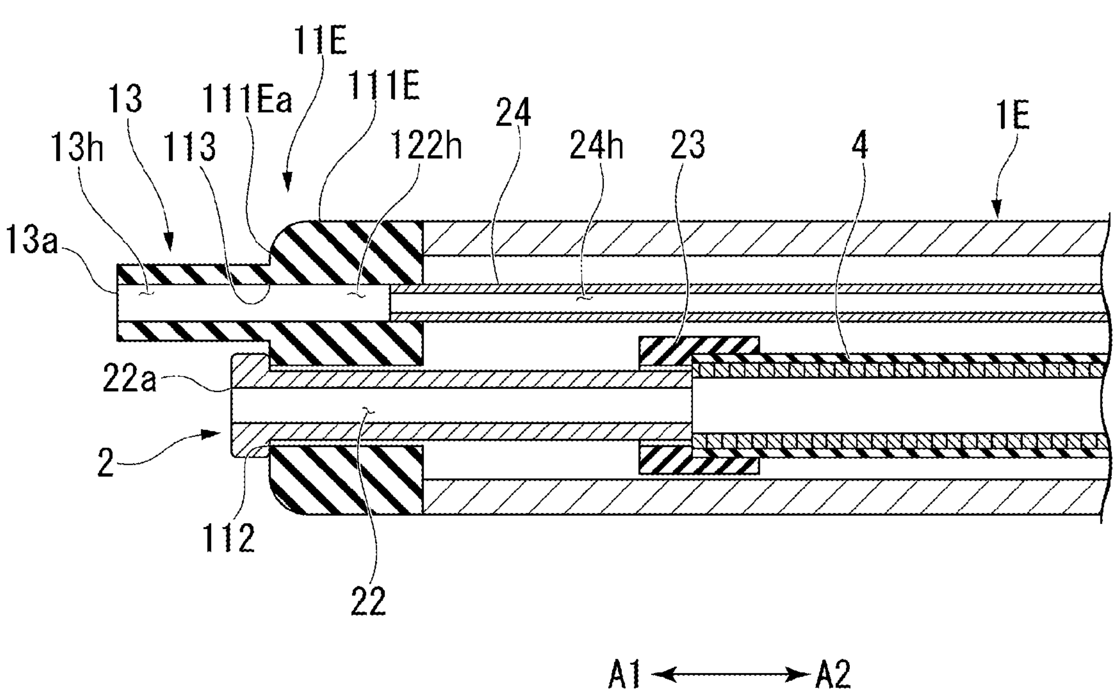
FIG. 32 is a cross-sectional view illustrating the insulation tip in a state in which a knife of the treatment tool has moved backward to a proximal end side.

As illustrated in FIG. 31, the protruding part opening 13*a* of the protruding part 13 may be disposed on the proximal end side A2 with respect to the knife 2 in a state in which the knife 2 has moved forward to the distal end side A1. Also, FIG. 32 is a cross-sectional view of the insulation tip 11E in a state in which the knife 2 has moved backward to the proximal end side A2. As illustrated in FIG. 32, the protruding part opening 13*a* of the protruding part 13 may be disposed on the distal end side A1 with respect to the knife 2 in a state in which the knife 2 has moved backward to the proximal end side A2 (a state in which the flange 21 of the knife 2 is in contact with the distal end surface 111Ea of the insulation tip main body 111E). With this configuration, the operator can easily perform a local injection treatment by disposing the protruding part 13, which is provided in the insulation tip 11E of the sheath 1E and has the protruding part opening 13*a* through which the supplied liquid flows out, in the vicinity of a lesion portion.

Figure 33:
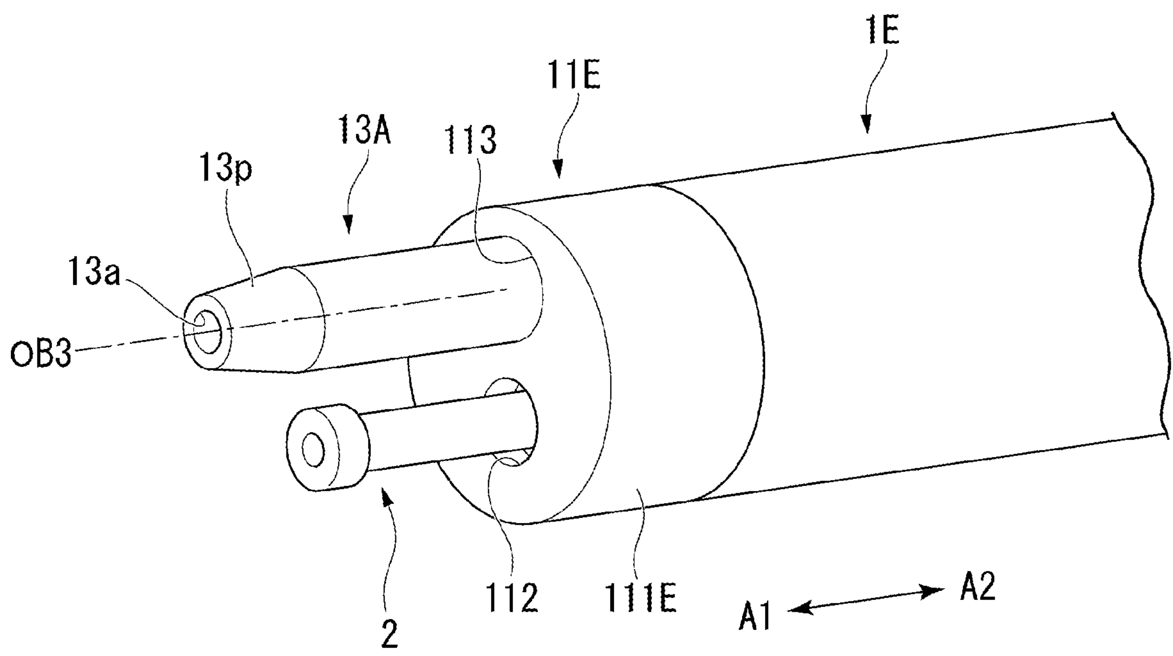
FIG. 33 is a perspective view illustrating a protruding part which is a modified example of a protruding part of the insulation tip.

The protruding part 13 is not limited to the above-described embodiment. FIG. 33 is a perspective view of a protruding part 13A which is a modified example of the protruding part 13. The protruding part 13A may include a tapered surface 13*p* that is inclined toward the central axis OB3 from the proximal end side A2 toward the distal end side A1 at a distal end part thereof. In this case, since the distal end part of the protruding part 13A, which has the protruding part opening 13*a* through which the liquid flows out, has the tapered surface 13*p*, the operator can easily insert the protruding part opening 13*a* of the protruding part 13A into the submucosal layer to perform the local injection treatment.

Figure 34:
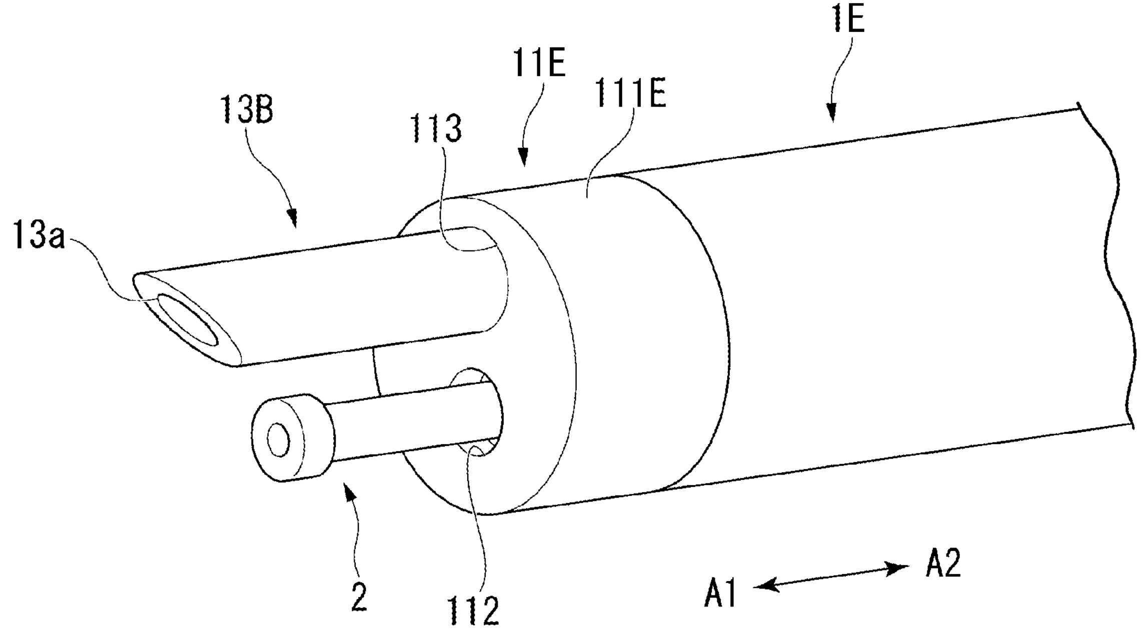
FIG. 34 is a perspective view illustrating a protruding part which is a modified example of the protruding part of the insulation tip.

The protruding part 13 is not limited to the above-described embodiment. FIG. 34 is a perspective view of a protruding part 13B which is a modified example of the protruding part 13 of the insulation tip 11D. A distal end part 13*b* of the protruding part 13B may be inclined toward an axis passing through one end of a circumferential edge of the protruding part 13B in the longitudinal direction A from the proximal end side A2 toward the distal end side A1. With this configuration, the distal end part of the protruding part 13B may include a sharp or pointed shape. Even in this case, the operator can easily insert the protruding part opening 13*a* of the protruding part 13B into the submucosal layer to perform the local injection treatment.

Figure 35:
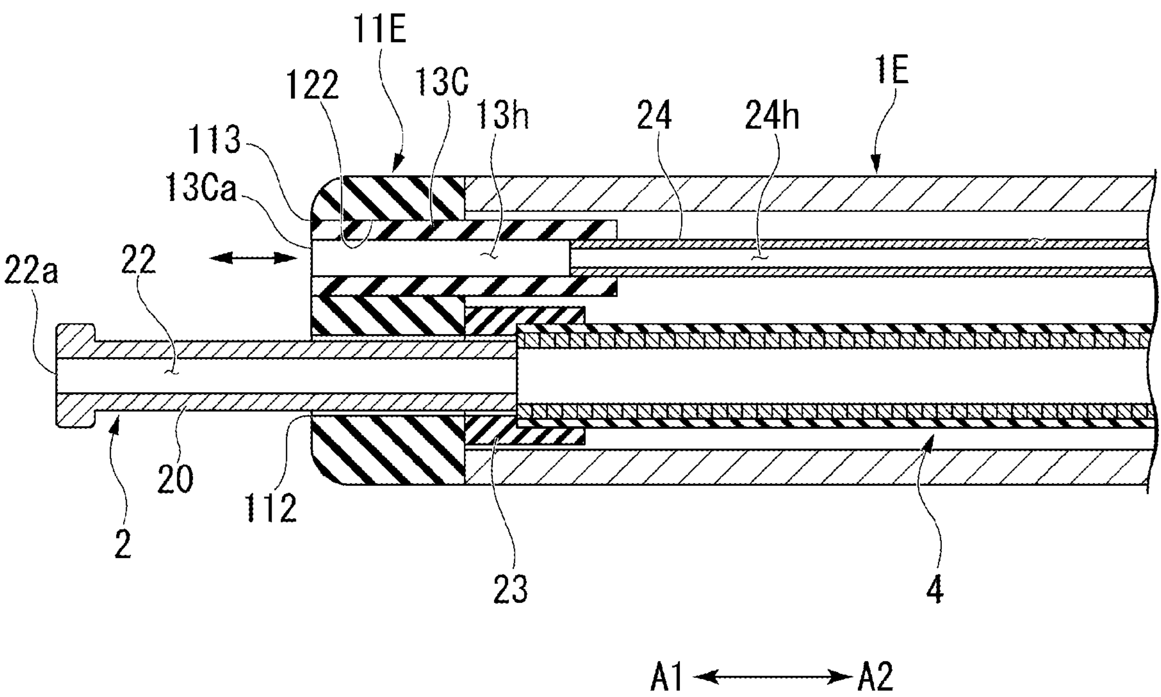
FIG. 35 is a cross-sectional view illustrating a protruding part which is a modified example of the protruding part of the insulation tip.

Also, the protruding part 13 is not limited to the above-described embodiment. FIG. 35 is a cross-sectional view of a protruding part 13C which is a modified example of the protruding part 13. The protruding part 13C may be configured to be movable forward and backward in the longitudinal direction A as illustrated in FIG. 35. Specifically, a proximal end of the protruding part 13C may be fixed to a distal end of the water supply tube 24. An operation unit 5 may include a lever 55, and a proximal end of the water supply tube 24 may be attached to the lever 55. Therefore, when the operator moves the lever 55 forward and backward in the longitudinal direction A, the water supply tube 24 and the protruding part 13C can be moved forward and backward in the longitudinal direction A. As illustrated in FIG. 35, a protruding part opening 13Ca of the protruding part 13C may be disposed not to protrude from the second opening 113 of the insulation tip main body 111 to the distal end side A1. With this configuration, the operator can move the unused protruding part 13C to the proximal end side A2 with respect to the second opening 113 to accommodate it in the second through-hole 122 during incision, cauterization, or peeling treatments and a hemostasis treatment. Further, protruding part 13C and/or the water supply tube 24 may be configured so that it does not move forward and backward, and only the protruding part 13 moves forward and backward in the longitudinal direction A.

Figure 36:
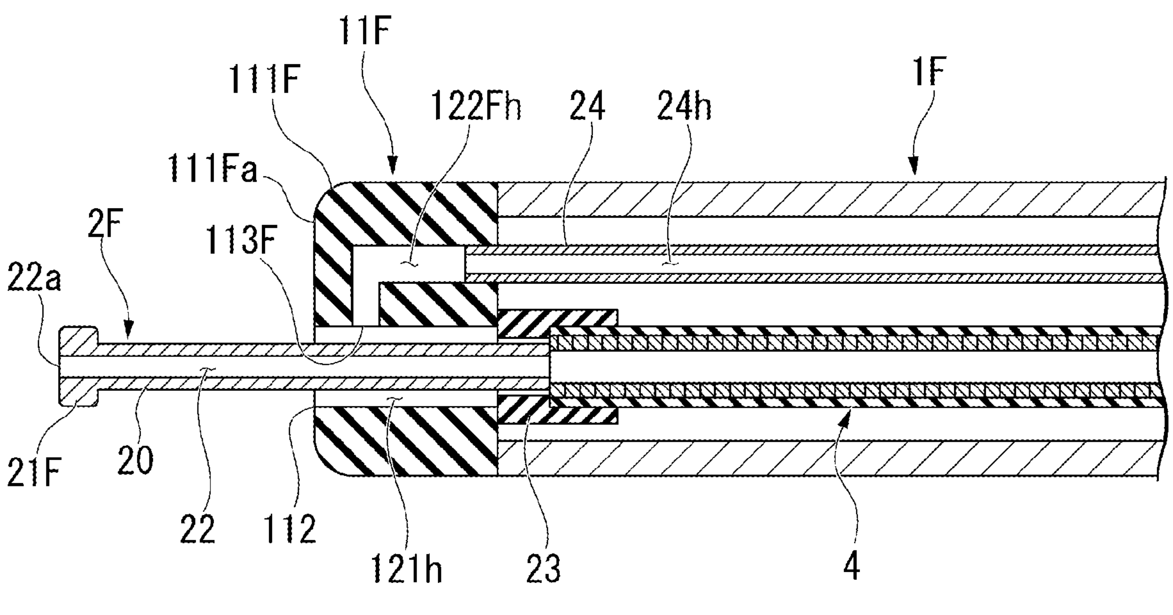
FIG. 36 is a cross-sectional view illustrating an insulation tip of a sheath which is a modified example of the insulation tip of the sheath of the treatment tool.

In the above-described embodiment, the insulation tip 11D of the sheath 1D may include the first opening 112 and the second opening 113 provided at a different position from the first opening 112 on the distal end surface 111*a* of the insulation tip main body 111. However, an aspect of the insulation tip 11D is not limited thereto. FIG. 36 is a cross-sectional view of an insulation tip 11F of a sheath 1F which is a modified example of the insulation tip 11D of the sheath 1D. Also, in the present embodiment, a knife 2F inserted into the sheath 1F may have a smaller width in a radial direction than the knife 2 of the above-described embodiment, and a flange 21F of the knife 2F may be moveable to the proximal end side A2 with respect to the first opening 112.

Compared to the insulation tip 11D of the second embodiment, the insulation tip 11F includes only the first opening 112 on a distal end surface 111Fa of an insulation tip main body 11F. Also, the insulation tip 11F includes a second distal end conduit 122Fh. The second distal end conduit 122Fh can be curved so that a distal end thereof faces the lower side Z2 inside the insulation tip 11F, and an internal insertion opening (second opening) 113F provided at the distal end is formed on a side surface of the first distal end conduit 121*h*. The proximal end side A2 of the second distal end conduit 122Fh may communicate or engage with the third water supply conduit 24*h* of the water supply tube 24.

Figure 37:
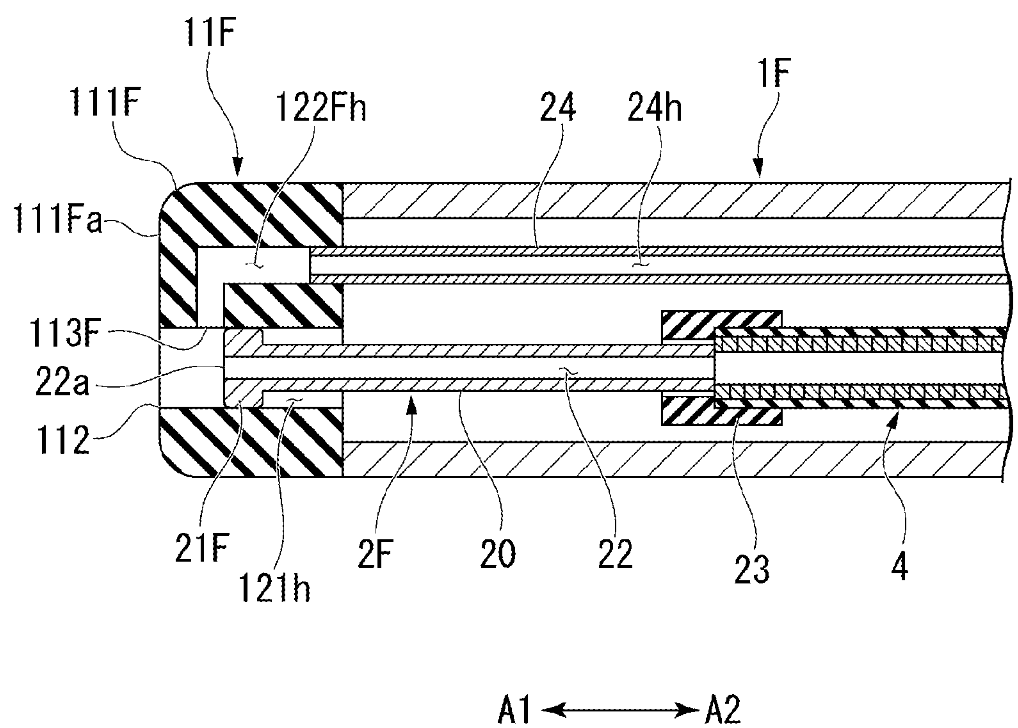
FIG. 37 is a cross-sectional view illustrating a state in which the knife of the treatment tool has been moved.

FIG. 37 is a cross-sectional view of a state in which the knife 2F has been moved. As illustrated in FIG. 37, when the operator moves the slider 52 to the proximal end side A2, the flange 21F of the knife 2F can move to the proximal end side A2 with respect to the internal insertion opening 113F. Then, in the first distal end conduit 121*h*, a space can be provided in which the fluid can flow out from the flange 21F to the distal end side A1. Therefore, the liquid flowing in the third water supply conduit 24*h* of the water supply tube 24 can be supplied into the second distal end conduit 122Fh, and then flows out from the internal insertion opening 113F. The fluid may pass through the first distal end conduit 121*h* and flows out from the first opening 112. In other words, in a state in which the liquid is flowed in from the internal insertion opening 113F, the flange (distal end part) 21F of the knife 2F is disposed on the proximal end side A2 with respect to the internal insertion opening 113F. According to this configuration, the operator can smoothly supply the liquid and perform the local injection treatment. Also, when the flange 21F of the knife 2F is disposed in the vicinity of the internal insertion opening 113F, even when tissues or burnt deposits of tissues adhere to the flange 21F, the fluid that has flowed out from the internal insertion opening 113F can cause the tissues or burnt deposits of tissues to flow and be discharged from the first opening 112.

Figure 38:
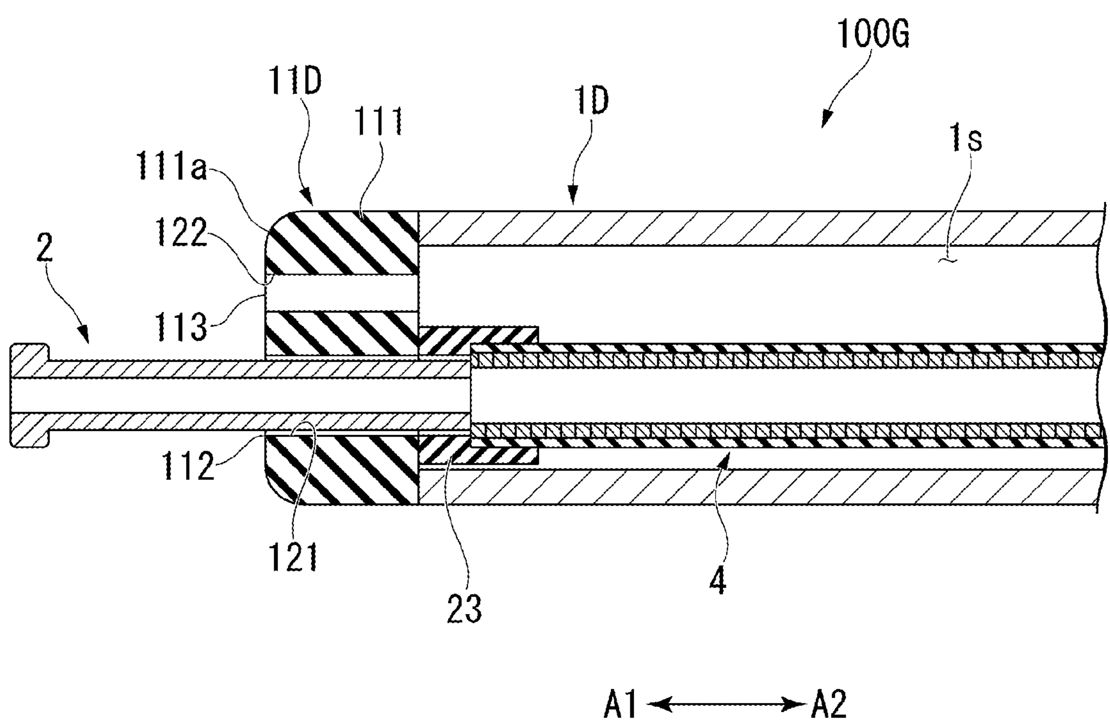
FIG. 38 is a cross-sectional view of a treatment tool which is a modified example of the treatment tool.

In the above-described embodiment, the treatment tool 100D according to the second embodiment includes a water supply tube 24. However, the treatment tool 100D is not limited to the above-described embodiment. FIG. 38 is a cross-sectional view of a treatment tool 100G which is a modified example of the treatment tool 100D. In the example illustrated in FIG. 38, the treatment tool 100G does not include the water supply tube 24. In this case, a water supply conduit of the fluid may be formed in the internal space is of the sheath 1D. Also in the present configuration, the treatment tool 100G can supply the fluid from the first opening 112 provided in the insulation tip main body 111 of the insulation tip 11D.

In the above embodiment, the central axis OB3 in the longitudinal direction A of the second through-hole 122 can extend parallel to the longitudinal direction A, but the aspect of the second through-hole is not limited to this.

Figure 39:
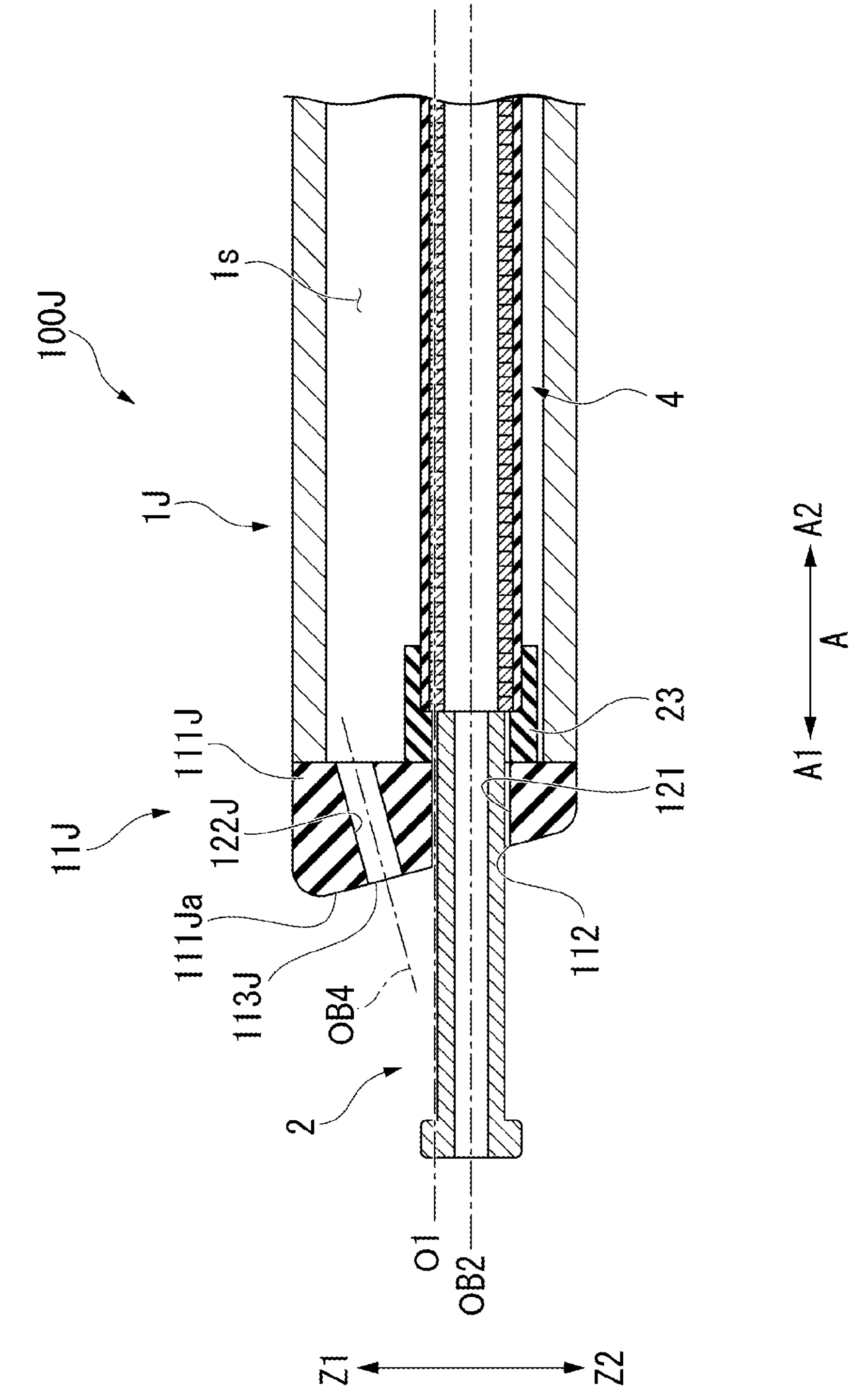
FIG. 39 is a cross-sectional view of a treatment tool which is a modified example of the treatment tool.

FIG. 39 is a sectional view showing a treatment instrument 100J that is a modification of the treatment instrument 100D. The treatment tool 100J may include a sheath 1J, a knife 2, a connecting insert 23, an operating wire 4, and may include an operation unit.

An insulating tip 11J (distal end member) may be provided at a distal end 1*a* of the sheath 1J. The insulating tip 11J may include two different through-holes. The insulating tip 11J may further include an insulating tip body 111J (distal end member body), a first through-hole 121, and a second through-hole 122J.

The insulating tip body 111J may be the main body portion of the insulating tip 11J. The insulating tip body 111J may include a first opening 112 on the distal end surface 111Ja of the distal end side A1, and a second opening 113J, provided at a position different from the first opening 112 and through which the fluid passing through the internal space is of the sheath 1J flows out.

The first through-hole 121 may be a hole that penetrates the insulating tip body 111J in the longitudinal direction A, similarly to the above embodiment.

The second through-hole 122J may be a hole that penetrates the insulating tip body 111J so that the central axis OB4 of the second through-hole 122J intersects the central axis OB2 of the first through-hole 121, as shown in FIG. 39. That is, the second through-hole 122J may be provided so that the central axis OB4 intersects with the central axis of the knife 2.

Therefore, the fluid passing through the internal space is of the sheath 1J can be released toward the knife 2 from the second opening 113J. As a result, the scorched tissue adhered to the knife 2 can be efficiently washed away by the fluid released from the second opening 113J.

While the second embodiment of the present disclosure has been described in detail above with reference to the drawings, the specific configurations are not limited to the embodiment and may include design changes or the like within a range not departing from the scope of the present disclosure. Also, the components illustrated in the above-described embodiment and modified examples can be configured by appropriately combining them.

The present disclosure includes the following technical ideas.

(Additional Statement 1)

An endoscopic treatment tool, including:

a sheath extending in a longitudinal direction and having a water supply conduit for water supply inside;

a high-frequency knife made of a metal inserted into the sheath and moving forward and backward in the longitudinal direction; and a distal end member having insulating properties provided at a distal end of the sheath, in which the distal end member has a first opening through which the high-frequency knife is inserted on the distal end surface, and a second opening provided at a different position from the first opening and through which a fluid passing through the water supply conduit flows out.

(Additional Statement 2)

The endoscopic treatment tool according to additional statement 1, in which a high-frequency current flows through the high-frequency knife.

(Additional Statement 3)

The endoscopic treatment tool according to additional statement 1 or 2, further including:

an operation wire extending in the longitudinal direction and having a distal end connected to the high-frequency knife; and an operation unit provided at a proximal end of the operation wire, in which the high-frequency knife moves forward and backward in the longitudinal direction when the operation unit is operated.

(Additional Statement 4)

The endoscopic treatment tool according to additional statement 1 or 2, further including:

a liquid supply tube inserted into the sheath and having the water supply conduit for water supply inside, in which a fluid flowing through the liquid supply tube flows out from the second opening.

(Additional Statement 5)

An endoscopic treatment tool, including:

a sheath extending in a longitudinal direction and having a water supply conduit for water supply inside;

a high-frequency knife made of a metal inserted into the sheath and moving forward and backward in the longitudinal direction; and a distal end member having insulating properties provided at a distal end of the sheath, in which the distal end member includes a first distal end conduit in which a first opening through which the high-frequency knife is inserted is provided on a distal end surface, and a second distal end conduit having an internal insertion opening on a side surface of the first distal end conduit and to which a fluid is supplied from the water supply conduit, and the fluid supplied to the second distal end conduit is flowed out from the first opening.

(Additional Statement 6)

The endoscopic treatment tool according to additional statement 5, in which a distal end part of the high-frequency knife is disposed on a proximal end side with respect to the internal insertion opening in a state in which a liquid is flowed out from the second opening.

Third Embodiment

A third embodiment of the present disclosure will be described with reference to FIGS. 40 to 42. In the following description, components that are common to those already described will be denoted by the same reference signs and duplicate description will be omitted. Further, the following embodiments are all different from the first embodiment in configuration of an endoscopic treatment system using a treatment tool. Therefore, the following description will be described focusing on differences from the first embodiment.

[Endoscopic Treatment System (Treatment System, High-Frequency Knife System) 300H]

Figure 40:
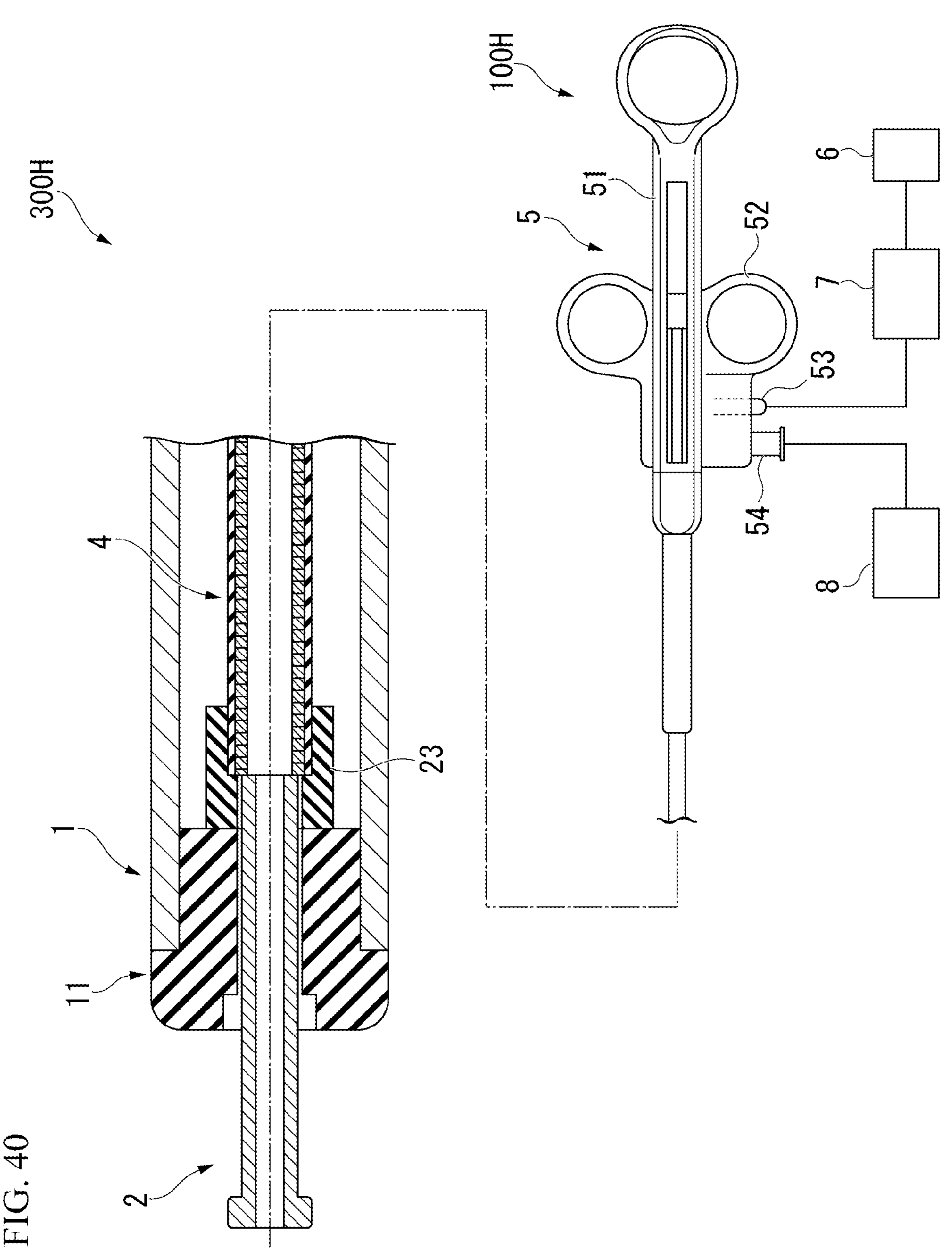
FIG. 40 is a view illustrating an endoscopic treatment system.
Figure 41:
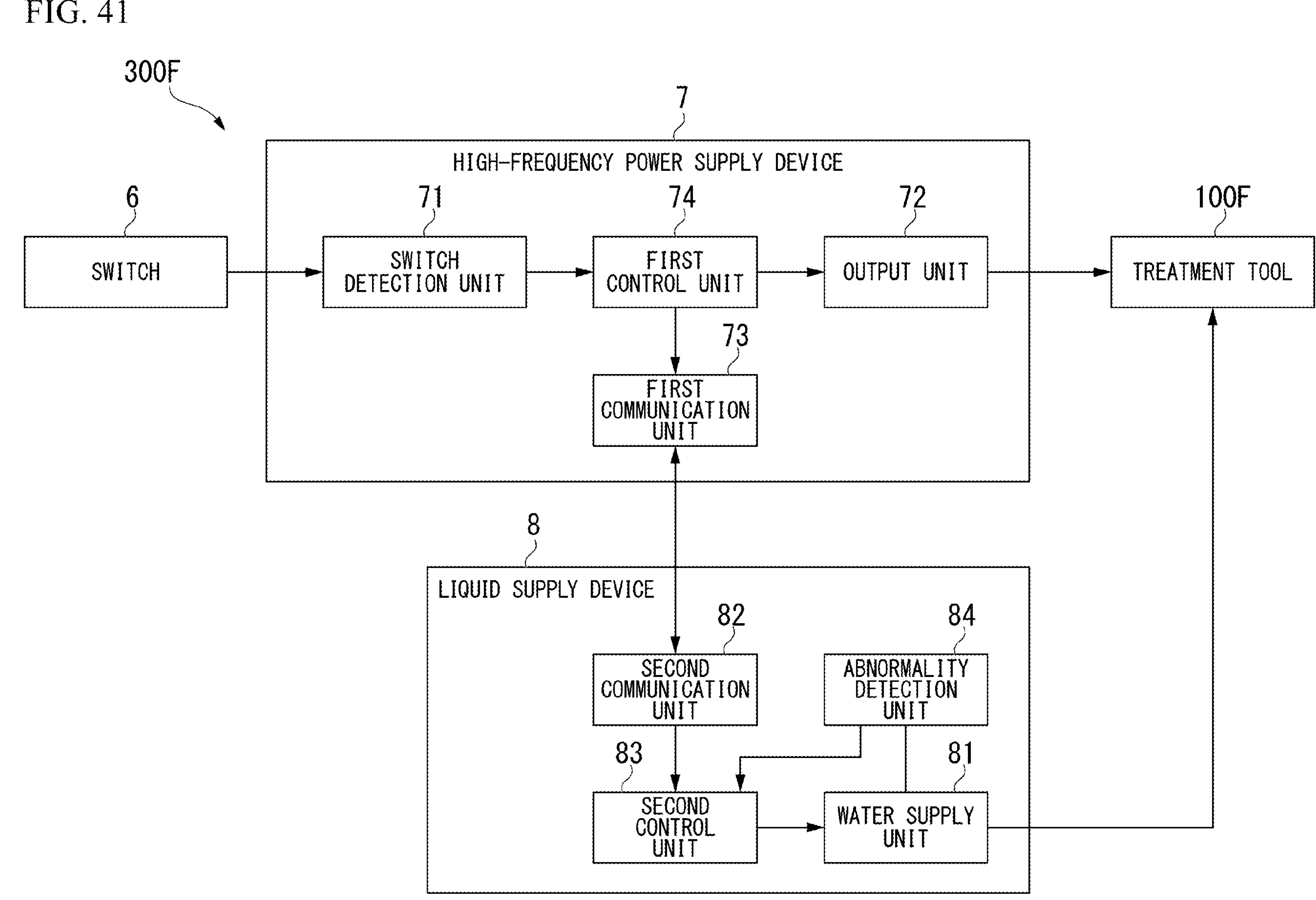
FIG. 41 is a schematic configuration view showing an example of the endoscopic treatment system.

FIG. 40 is a view illustrating an endoscopic treatment system 300H according to the third embodiment. FIG. 41 is a schematic configuration view showing an example of the endoscopic treatment system 300H.

As illustrated in FIG. 40, an endoscopic treatment system 300H (treatment system, high-frequency knife system) using a treatment tool according to the third embodiment of the present disclosure may include an endoscope (not shown), a treatment tool 100H, a switch (a foot switch) 6, a high-frequency power supply device 7, and a liquid supply device 8. The treatment tool 100H may have the same configuration as the treatment tool 100 except that the rod 3 (rod-shaped member) and the lever 55 of the operation unit 5 may not be provided (be omitted or excluded) compared to the first embodiment described above.

The switch 6 may be foot switch or any suitable switch or actuation member. The switch 6 may communicate with (or be coupled to) the high-frequency power supply device 7 by wire or wirelessly. The switch 6 can transmit a power on/off signal to the high-frequency power supply device 7.

The high-frequency power supply device 7 may supply high-frequency energy to the treatment tool 100H. Specifically, the high-frequency power supply device 7 may be electrically connected to a power supply connector 53 provided in an operation unit 5. The high-frequency power supply device 7 can switch whether or not to output the high-frequency energy by receiving the power on/off signal according to an operation of the switch 6 by the operator. The high-frequency power supply device 7 may include a switch detection unit 71, an output unit 72, a first communication unit 73, and a first control unit 74.

The switch detection unit 71 may detect a power on/off signal of the switch 6. When the switch detection unit 71 detects the power on/off signal, it can transmit power on/off detection information to the first control unit 74. In an example, the switch detection unit 71 may include a current detection sensor.

The output unit 72 may acquire an output signal from the first control unit 74 and in response, output the high-frequency energy to the treatment tool 100H. Also, the output unit 72 may acquire an output stop signal from the first control unit 74 and in response stop or cease outputting the high-frequency energy to the treatment tool 100H.

The first communication unit 73 may include a communication interface. The first communication unit 73 may communicate with the liquid supply device 8 or other devices by, for example, a wired cable or via wireless communication. In an example, first communication unit 73 may be a device that communicates with an access point connected to the Internet using a predetermined protocol such as a wireless local area network (LAN).

When the first communication unit 73 acquires the power on/off information from the first control unit 74, the first communication unit 73 may transmit the power on/off information to the liquid supply device 8. When the first communication unit 73 acquires abnormality detection information from the liquid supply device 8, the first communication unit 73 may transmit the information to the first control unit 74.

The first control unit 74 may be a program-executable device (computer) having a central processing unit (CPU), a memory capable of reading a program, a storage unit (not shown), and the like. Functions of the first control unit 74 may be realized or executed by the CPU executing a program provided to the first control unit 74. Further, at least some of the functions of the first control unit 74 may be configured by a dedicated logic circuit or the like. The storage unit may be a nonvolatile recording medium that stores a program or necessary data. The storage unit is configured by, for example, a ROM, a hard disk, or the like. The program recorded in the storage unit may be read into the memory and executed by the CPU.

When the first control unit 74 acquires the power on/off detection information (input state) from the switch detection unit 71, the first control unit 74 may generate an output signal or an output stop signal and may transmit the output signal to the output unit 72. Also, when the first control unit 74 acquires the abnormality detection information from the liquid supply device 8 via the first communication unit 73, the first control unit 74 may generate an output stop signal and transmits the output stop signal to the output unit 72.

Also, when the first control unit 74 acquires the power on/off detection information from the switch detection unit 71, the first control unit 74 may generate power on/off information to transmit an instruction to the first communication unit 73.

Further, the first control unit 74 is not limited to a device included in one piece of hardware. For example, the first control unit 74 may be configured by separating the CPU, memory, and storage unit into pieces of hardware, and then connecting the pieces of hardware to each other via a communication link. Alternatively, the first control unit 74 may realize the first control unit as a cloud system by separating the storage unit and similarly connecting separated parts of the storage unit to each other via a communication link. Further, the first control unit 74 may further include other components necessary for an operation of the first control unit 74 besides the CPU, the memory, and the storage unit.

The liquid supply device 8 may supply a liquid (e.g., water) to the treatment tool 100H. The liquid supply device 8 may be connected to a liquid supply port 54 provided in the operation unit 5. The liquid supply device 8 can supply the liquid to the treatment tool 100H by acquiring the power on/off information from the high-frequency power supply device 7 when power on/off of the high-frequency power supply device is operated by the switch 6. The liquid supply device 8 may include a water supply unit 81, a second communication unit 82, a second control unit 83, and/or an abnormality detection unit 84. In an example, the liquid supply device 8 may include a pressure pump for liquid supply.

The water supply unit 81 can acquire or receive a water supply signal from the second control unit 83, and in response to receiving the water supply signal start supplying supply by supplying the liquid to the treatment tool 100H. Also, the water supply unit 81 may acquire or receive a water supply stop signal from the second control unit 83 and in response stop or cease the water supply to the treatment tool 100H.

The second communication unit 82 may include a communication interface. The second communication unit 82 may communicate with the high-frequency power supply device 7 or other devices by, for example, a wired cable or via wireless communication. In an example, the second communication unit 82 may be a device that communicates with an access point connected to the Internet using a predetermined protocol such as a wireless local area network (LAN).

The second communication unit 82 may communicate with the first communication unit 73 of the high-frequency power supply device 7. When the second communication unit 82 acquires or receives the power on/off information of the high-frequency power supply device 7 from the first communication unit 73, the second communication unit 82 may transmit the power on/off information to the second control unit 83.

The second control unit 83 may be a program-executable device (computer) having a central processing unit (CPU), a memory capable of reading a program, a storage unit (not shown), and the like. Functions or operations of the second control unit 83 may be realized by the CPU executing a program provided to the second control unit 83. Further, at least some of the functions of the second control unit 83 may be configured by a dedicated logic circuit or the like. The storage unit may be a nonvolatile recording medium that stores a program or necessary data. The storage unit may be configured by, for example, a ROM, a hard disk, or the like. The program recorded in the storage unit is read into the memory and executed by the CPU.

When the second control unit 83 acquires the power on/off information from the second communication unit 82, the second control unit 83 may generate a water supply signal and in response send transmit an instruction to the water supply unit 81.

Further, the second control unit 83 is not limited to a device included in one piece of hardware. For example, the second control unit 83 may be configured by separating the CPU, memory, and storage unit into pieces of hardware, and then connecting the pieces of hardware to each other via a communication link. Alternatively, the second control unit 83 may realize the second control unit 83 as a cloud system by separating the storage unit and similarly connecting separated parts of the storage unit to each other via a communication link. Further, the second control unit 83 may further include other components necessary for an operation of the second control unit 83 besides the CPU, the memory, and the storage unit.

While water or other liquid (e.g., saline) is supplied from the water supply unit 81 to the treatment tool 100H, the abnormality detection unit 84 may detect an abnormality indicating the occurrence of a problem when water is not supplied sufficiently due to, for example, the distal end opening 22*a* being blocked by burnt deposits of tissues becoming fixed or the like, or the treatment tool 100H, which has a water supply conduit through which the fluid flows, being buckled. When the abnormality detection unit 84 detects an abnormality, the abnormality detection unit 84 can transmit abnormality detection information to the second control unit 83.

When the second control unit 83 acquires the abnormality detection information from the abnormality detection unit 84, the second control unit 83 may transmit a water supply stop signal to the water supply unit 81. Also, the second control unit 83 may transmit the abnormality detection information to the high-frequency power supply device 7 via the second communication unit 82.

Here, the endoscopic treatment system 300H may further include a warning output unit. When the warning output unit is included, the abnormality detection unit 84 may transmit the abnormality detection information to the warning output unit when the abnormality detection unit 84 detects an abnormality, and the warning output unit can acquire the abnormality detection information to generate a warning sound or turn on a warning lamp.

[Operation of Endoscopic Treatment System 300H]

Figure 42:
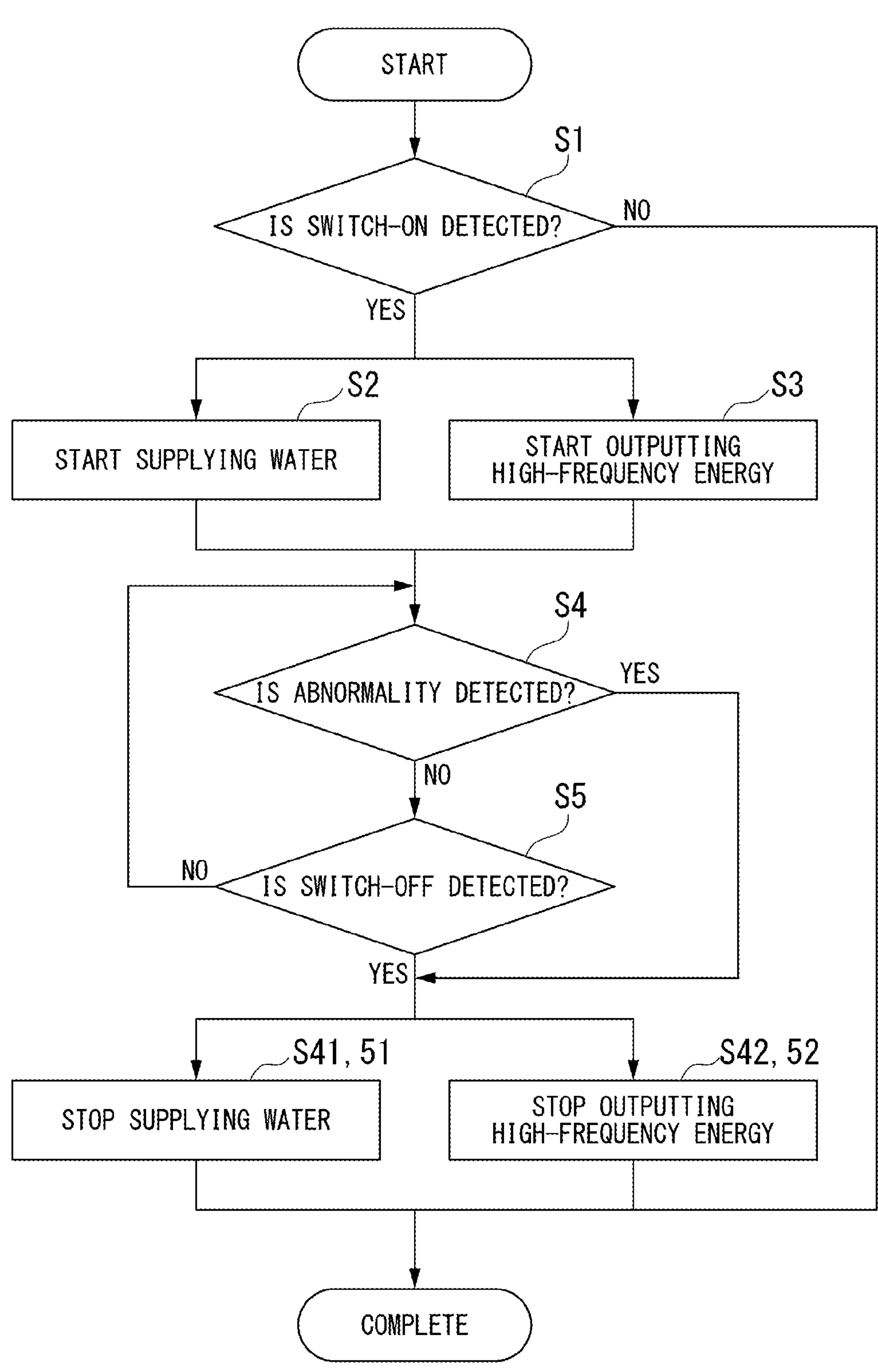
FIG. 42 is a flowchart explaining an operation of the endoscopic treatment system.

FIG. 42 is a flowchart explaining an operation of the endoscopic treatment system 300H.

<Switch-on Detection (First Detection) S1>

First, the operator may operate or engage a foot switch (or similar actuation member). When the switch 6 transmits a power-on signal to the high-frequency power supply device 7, the switch detection unit 71 of the high-frequency power supply device 7 may detect the power-on signal of the switch 6.

<Water Supply Start (First Supply) S2>

The switch detection unit 71 may transmit power-on detection information to the first control unit 74. When the first control unit 74 acquires the power-on detection information from the switch detection unit 71, the first control unit 74 may generate power-on information and transmits an instruction to the first communication unit 73. When the first communication unit 73 acquires the power-on information from the first control unit 74, the first communication unit 73 may transmit the power-on information to the liquid supply device 8. When the second communication unit 82 of the liquid supply device 8 acquires the power-on information, it may transmit the power-on information to the second control unit 83. When the second control unit 83 acquires the power-on information from the second communication unit 82, the second control unit 83 may generate a water supply signal and transmits an instruction to the water supply unit 81. The water supply unit 81 may acquire the water supply signal and starts water supply by supplying the liquid to the treatment tool 100H.

<High-Frequency Energy Output Start (Second Supply) S3>

When the first control unit 74 acquires the power-on detection information from the switch detection unit 71, the first control unit 74 may generate an output signal and may transmit the output signal to the output unit 72. The output unit 72 acquires the output signal from the first control unit 74 and starts outputting high-frequency energy to the treatment tool 100H. That is, when the first control unit 74 acquires the power-on detection information of the switch 6 from the switch detection unit 71, the first control unit 74 may cause the liquid supply device 8 to start supplying the fluid from the water supply unit 81 and causes the output unit 72 to start outputting the high-frequency energy.

The high-frequency power supply device 7 and the liquid supply device 8 may be interlocked so as to be able to simultaneously supply the high-frequency energy and the fluid to the treatment tool 100H. In other words, the high-frequency power supply device 7 and the liquid supply device 8 can communicate with each other, and one controls the other to be interlocked. Further, the high-frequency energy and the fluid can be simultaneously supplied to the treatment tool 100H, but in an example, the fluid may be supplied to the treatment tool 100H before the high-frequency energy is supplied. A timing of supplying the high-frequency energy and the fluid can be arbitrarily adjusted by the first control unit 74 of the high-frequency power supply device 7 and the second control unit 83 of the liquid supply device 8. In this state, the operator can perform the insertion step, the local injection step, the incision/cauterization/peeling step, the removal step, the additional local injection step, and the hemostasis step described above using the treatment tool 100H. Also, the operator can continue the above-described steps as necessary. The interlocking between the high-frequency power supply device 7 and the liquid supply device 8 is not limited to the state in which high-frequency energy or fluid is supplied and includes a state in which the high-frequency power supply device 7 and the liquid supply device 8 are communicating with each other.

<Abnormality Detection S4>

The abnormality detection unit 84 of the liquid supply device 8 may transmit abnormality detection information to the second control unit 83 when an abnormality indicating the occurrence of a problem is detected while the liquid supply device 8 supplies water from the water supply unit 81 to the treatment tool 100H.

<Abnormality Stop S41 and S42>

When the second control unit 83 acquires the abnormality detection information from the abnormality detection unit 84, it may transmit a water supply stop signal to the water supply unit 81. When the water supply unit 81 acquires the water supply stop signal from the second control unit 83, it can stop or cease supplying water to the treatment tool 100H. The second control unit 83 may further transmit the abnormality detection information to the high-frequency power supply device 7 via the second communication unit 82. When the first communication unit 73 of the high-frequency power supply device 7 acquires the abnormality detection information from the liquid supply device 8, the first communication unit 73 may transmit the abnormality detection information to the first control unit 74. When the first control unit 74 acquires the abnormality detection information, it may generate an output stop signal and transmits the output stop signal to the output unit 72, and in response the output unit 72 can stop or cease outputting the high-frequency energy to the treatment tool 100H. Further, if an abnormality is not detected by the abnormality detection unit 84, the high-frequency power supply device 7 and the liquid supply device 8 can continue to supply the high-frequency energy and the fluid to the treatment tool 100H.

<Switch-Off Detection (Second Detection) S5>

As operator operates the switch 6 to transmit a power-off signal to the high-frequency power supply device 7, the switch detection unit 71 of the high-frequency power supply device 7 can the power-off signal from the switch 6.

<Water Supply Stop (First Stop) S51>

The switch detection unit 71 may transmit power-off detection information to the first control unit 74. When the first control unit 74 acquires the power-off detection information from the switch detection unit 71, the first control unit 74 generates power-off information and transmits an instruction to the first communication unit 73. When the first communication unit 73 acquires the power off information from the first control unit 74, the first communication unit 73 transmits the power off information to the liquid supply device 8. When the second communication unit 82 of the liquid supply device 8 acquires the power off information, it can transmit the power off information to the second control unit 83. When the second control unit 83 acquires the power-off information from the second communication unit 82, the second control unit 83 can generate a water supply stop signal and transmits an instruction to the water supply unit 81. The water supply unit 81 can acquire or receive the water supply stop signal and stops supplying water to the treatment tool 100H.

<High-Frequency Energy Output Stop (Second Stop) S52>

When the first control unit 74 acquires the power-off detection information from the switch detection unit 71, the first control unit 74 may generate an output stop signal and transmits it to the output unit 72. The output unit 72 may acquire or receive the output stop signal from the first control unit 74 and may stop outputting the high-frequency energy to the treatment tool 100H. That is, when the first control unit 74 acquires the power-off detection information of the switch 6 from the switch detection unit 71, the first control unit 74 can cause the liquid supply device 8 to stop supplying the fluid from the water supply unit 81 and can cause the output unit 72 to stop outputting the high-frequency energy. The high-frequency power supply device 7 and the liquid supply device 8 can be interlocked to be able to stop the supply of the high-frequency energy and the fluid to the treatment tool 100H. The operator can end or complete the ESD procedure by performing the above-described steps as necessary.

According to the endoscopic treatment system (treatment system) 300H of the present embodiment, the high-frequency power supply device 7 and the liquid supply device 8 may be interlocked to be able to simultaneously supply the high-frequency energy and the fluid to the treatment tool 100H. Thus, the operator can simultaneously perform the incision, cauterization, or peeling treatments, and the hemostasis treatment while supplying the fluid to perform the local injection treatment by operating the switch 6. Therefore, tissues can be prevented from entering the distal end opening (water supply port) 22*a* of the knife 2 of the treatment tool 100H, and the distal end opening 22*a* and as a result causing a clog or the tissues becoming burnt deposits.

The liquid supply device 8 according to the above-described embodiment may supply (feed) air in addition to a fluid.

The switch 6 according to the above-described embodiment may communicate with the high-frequency power supply device 7 by wire or wirelessly, but the present disclosure is not particularly limited. In an example, the switch 6 may communicate with the liquid supply device 8 by wire or wirelessly. In such an example, the above-described endoscopic treatment system 300H can be operated by providing a switch detection unit in the liquid supply device 8. Further, the switch 6 may communicate with both the high-frequency power supply device 7 and the liquid supply device 8 by via a wired connection or wirelessly.

The switch 6 is not limited to the foot switch described above, and can include, for example, a touch panel, various types of switches such as a mouse and a keyboard, and a switch using any of devices capable of performing an operation such as a lever and a remote controller.

In the treatment system 300H according to the embodiment described above, the high-frequency power supply device 7 and the liquid supply device 8 may work together to simultaneously supply high-frequency energy and fluid to the treatment instrument 100H, but the aspect of the treatment system is not limited to such operation. For example, in the treatment system, the switch detection unit 71 of the high-frequency power supply device 7 may detect a power-on signal from the switch 6, and may start outputting high-frequency energy to the treatment instrument 100H. Further, the treatment system may start feeding the liquid to the treatment tool 100H after detecting the stop of the high-frequency energy supply by the high-frequency power supply device 7. In this way, by serially outputting high-frequency energy and fluid, it is possible to wash away the burnt deposits of the tissues adhered to the knife 2 with the fluid after performing the incision, cauterization, and peeling steps.

While the third embodiment of the present disclosure has been described in detail above with reference to the drawings, the specific configurations are not limited to the embodiment and may include design changes or the like within a range not departing from the scope of the present disclosure. Also, the components illustrated in the above-described embodiment and modified examples can be configured by appropriately combining them.

The present disclosure includes the following technical ideas.

(Additional Statement 7)

A high-frequency knife system, including:

an endoscopic treatment tool having a high-frequency knife inserted into a channel of an endoscope and extending in a longitudinal direction to be movable forward and backward, a first conduit extending in the longitudinal direction and through which a liquid flows, and a first opening from which the liquid flows out;

a high-frequency power supply device supplying high-frequency energy to the high-frequency knife;

a switch configured to start or stop supplying the high-frequency energy; and a liquid supply device supplying a fluid to the first conduit, in which the high-frequency power supply device and the liquid supply device are interlocked.

(Additional Statement 8)

The high-frequency knife system according to additional statement 7, in which the high-frequency knife has the first opening at a distal end and the first conduit inside.

(Additional Statement 9)

The high-frequency knife system according to additional statement 7, in which the endoscopic treatment tool further includes a sheath extending in the longitudinal direction and into which the high-frequency knife can be inserted, and a distal end member having insulating properties provided at a distal end of the sheath, and the distal end member includes a first through-hole penetrating in the longitudinal direction and into which the high-frequency knife can be inserted, and a second through-hole having the first opening on a distal end side and penetrating in the longitudinal direction.

(Additional Statement 10)

The high-frequency knife system according to additional statement 7 or 8, in which the liquid supply device supplies air or water.

(Additional Statement 11)

The high-frequency knife system according to additional statement 7 or 8, in which the liquid supply device and the high-frequency power supply device communicate with each other, and at least one controls the other.

(Additional Statement 12)

The high-frequency knife system according to additional statement 7 or 8, in which the liquid supply device supplies the fluid when the high-frequency power supply device supplies the high-frequency energy.

(Additional Statement 13)

The high-frequency knife system according to additional statement 7 or 8, further including:

a detection unit detecting an abnormality in operation of the liquid supply device, in which the high-frequency power supply device stops outputting when the detection unit detects an abnormality in operation of the liquid supply device.

(Additional Statement 14)

A control method of a high-frequency knife, in which supply of high-frequency energy and a fluid is controlled by a switch, the control method including:

a first detection step of detecting the switch being turned on;

a first supply step of starting supply of the fluid;

a second supply step of starting supply of the fluid and starting supply of the high-frequency energy;

a second detection step of detecting the switch being turned off;

a first stop step of stopping supply of the fluid; and a second stop step of stopping supply of the fluid and stopping supply of the high-frequency energy.

(Additional Statement 15)

The control method of a high-frequency knife according to additional statement 14, further including:

an abnormality detection step of detecting an abnormality in supply of the fluid; and an abnormality stop step of stopping supply of the fluid and supply of the high-frequency energy.

In any of the embodiments described above, according to the endoscopic treatment tool, water supply from a distal end of the high-frequency knife or sheath can be suitably performed. All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the embodiments should be determined with reference to the appended claims, along with the full scope of equivalents to which such claims are entitled.

What is claimed is:

1. An endoscopic treatment tool, comprising:

a sheath extending in a longitudinal direction;

a distal end member having insulation and the distal end member provided at a distal end of the sheath and having a through-hole penetrating in the longitudinal direction;

an electrode having a first conduit extending in the longitudinal direction and the electrode being configured to advance and retract into the through-hole;

a hollow operation wire having a second conduit communicating with the first conduit in the longitudinal direction, wherein the hollow operation wire includes a distal end connected to the electrode;

an operation unit configured to advance and retract the hollow operation wire in the longitudinal direction, wherein the operation unit includes:

a slider connected to a proximal end of the hollow operation wire and configured to advance and retract the electrode in the longitudinal direction; and a slide lever configured to advance and retract a rod relative to the electrode in the longitudinal direction; and the rod extending in the longitudinal direction and configured to be arranged in at least a part of the first conduit, wherein, when the slide lever is fully retracted, a distal end of the rod is located proximally relative to a proximal end of the electrode.

2. The endoscopic treatment tool according to claim 1, wherein, when a distal end of the rod is located at a first position, at which a distal end opening of the first conduit is located, in the longitudinal direction, the distal end opening is sealed to prevent biological tissue from entering the first conduit through the distal end opening.

3. The endoscopic treatment tool according to claim 1, wherein, when the slide lever is fully retracted, the distal end of the rod is located within the hollow operation wire.

4. The endoscopic treatment tool according to claim 1, wherein:

when the slide lever is moved in a distal direction along the longitudinal direction, the distal end of the rod is disposed in the longitudinal direction at a first position where a distal end opening of the first conduit is located to seal the distal end opening; and when the slide lever is moved in a proximal direction along the longitudinal direction, the distal end of the rod is disposed in the longitudinal direction at a second position closer to the proximal end than the distal end opening to open the distal end opening and enable water to flow through the first conduit.

5. The endoscopic treatment tool according to claim 1, wherein the rod is configured to extend and is movable forward and backward in the longitudinal direction.

6. The endoscopic treatment tool according to claim 5, wherein the rod includes:

a support column part extending in the longitudinal direction; and a distal end part provided on a distal end side of the support column part and having an outer diameter larger than that of the support column part, wherein the distal end part is configured to move distally relative to a distal end opening of the first conduit.

7. The endoscopic treatment tool according to claim 1, wherein the rod includes a protrusion on an outer surface thereof, and when the slide lever is fully advanced, the protrusion is located inside the electrode.

8. The endoscopic treatment tool according to claim 1, wherein the rod includes a char removal portion configured to remove char adhering to the first conduit by moving the rod back and forth relative to the electrode.

9. An endoscopic treatment tool, comprising:

a sheath extending in a longitudinal direction;

a distal end member having insulation and the distal end member provided at a distal end of the sheath and having a through-hole penetrating in the longitudinal direction;

an electrode having a first conduit extending in the longitudinal direction and the electrode being configured to advance and retract into the through-hole;

a hollow operation wire having a second conduit communicating with the first conduit in the longitudinal direction, wherein the hollow operation wire includes a distal end connected to the electrode;

an operation unit configured to advance and retract the hollow operation wire in the longitudinal direction, wherein the operation unit includes:

a slider connected to a proximal end of the hollow operation wire and configured to advance and retract the electrode in the longitudinal direction; and a slide lever configured to advance and retract a rod relative to the electrode; and the rod extending in the longitudinal direction and arranged in at least a part of the first conduit, wherein the rod includes:

a support column part extending in the longitudinal direction; and a distal end part provided on a distal end side of the support column part and having an outer diameter larger than that of the support column part, wherein the distal end part is configured to move distally relative to a distal end opening of the first conduit, and wherein, when the slide lever is fully retracted, the distal end part of the rod is located proximally relative to a proximal end of the electrode.

10. The endoscopic treatment tool according to claim 9, wherein:

when the slide lever is moved in a distal direction along the longitudinal direction, the distal end of the rod is disposed in the longitudinal direction at a first position where a distal end opening of the first conduit is located to seal the distal end opening; and when the slide lever is moved in a proximal direction along the longitudinal direction, the distal end of the rod is disposed in the longitudinal direction at a second position closer to the proximal end than the distal end opening to open the distal end opening and enable water to flow through the first conduit.

11. The endoscopic treatment tool according to claim 10, wherein the operation unit includes:

a stopper configured to regulate movement of the slide lever so as to limit a position of the distal end of the rod within a range between a distal end opening of the first conduit and the proximal end of the electrode.

12. The endoscopic treatment tool according to claim 11, wherein the distal end part is configured to seal the distal end opening to prevent biological tissue from entering the first conduit through the distal end opening.

13. The endoscopic treatment tool according to claim 12, wherein, when the slide lever is located proximally relative to the stopper, the distal end of the rod is located within the first conduit.

14. An endoscopic treatment tool, comprising:

a sheath extending in a longitudinal direction;

a distal end member having insulation and the distal end member provided at a distal end of the sheath and having a through-hole penetrating in the longitudinal direction;

an electrode having a first conduit extending in the longitudinal direction and the electrode being configured to advance and retract into the through-hole;

a rod extending in the longitudinal direction and configured to be arranged in at least a part of the first conduit, wherein the rod includes a plug that seals a distal end opening of the first conduit;

a hollow operation wire having a second conduit communicating with the first conduit in the longitudinal direction, wherein the hollow operation wire includes a distal end connected to the electrode; and an operation unit configured to advance and retract the hollow operation wire in the longitudinal direction, wherein the operation unit includes:

a slider connected to a proximal end of the hollow operation wire and configured to advance and retract the electrode in the longitudinal direction; and a slide lever configured to advance and retract the rod relative to the electrode in the longitudinal direction, wherein when the slide lever is fully retracted, a distal end of the rod is located proximally relative to a proximal end of the electrode.

15. The endoscopic treatment tool according to claim 14, wherein, the operation unit further includes a stopper configured to regulate advancement and retraction of the slide lever along the longitudinal direction, wherein the distal end of the rod is located within the first conduit when the slide lever is located proximally relative to the stopper, and wherein the slide lever further includes a positioning surface configured to generate a resistance force between the slide lever and the operation unit when the distal end of the rod protrudes from a distal end opening of the first conduit.

16. The endoscopic treatment tool according to claim 14, wherein the plug includes:

a support column part extending in the longitudinal direction;

a distal end part provided on a distal end side of the support column part and having an outer diameter larger than that of the support column part, wherein the distal end part is configured to move distally relative to a distal end opening of the first conduit; and a protrusion configured to remove biological tissue adhered to the first conduit.

17. The endoscopic treatment tool according to claim 16, wherein the distal end part is configured to seal the distal end opening to prevent biological tissue from entering the first conduit through the distal end opening.

18. The endoscopic treatment tool according to claim 15, wherein the stopper is detachably attached to the operation unit and configured to regulate movement of the slide lever so as to limit a position of the distal end of the rod within a range between a distal end opening of the first conduit and the proximal end of the electrode, wherein, when the slide lever is located proximally relative to the stopper, the distal end of the rod is located within the first conduit, wherein when the stopper is attached to the operation unit, the rod is in a regulated state in which a range in which the distal end of the rod advances or retracts is limited to a range located between the distal end opening and the proximal end of the electrode, and wherein when the stopper is detached from the operation unit, the rod is in a protruding state in which the distal end of the rod protrudes distally relative to the distal end opening.

* * * * *